(12) United States Patent
Mann et al.

(10) Patent No.: US 8,871,681 B2
(45) Date of Patent: Oct. 28, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND CERTAIN SULFONYLUREAS

(71) Applicants: Richard K. Mann, Franklin, IN (US); Carla N. Yerkes, Crawfordsville, IN (US); Norbert M. Satchivi, Westfield, IN (US); Paul R. Schmitzer, Indianapolis, IN (US)

(72) Inventors: Richard K. Mann, Franklin, IN (US); Carla N. Yerkes, Crawfordsville, IN (US); Norbert M. Satchivi, Westfield, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/837,990

(22) Filed: Mar. 15, 2013

(65) Prior Publication Data
US 2014/0031218 A1    Jan. 30, 2014

Related U.S. Application Data

(60) Provisional application No. 61/675,117, filed on Jul. 24, 2012.

(51) Int. Cl.
*A01N 25/26* (2006.01)
*A01N 43/40* (2006.01)

(52) U.S. Cl.
USPC .......................................... 504/100; 504/130

(58) Field of Classification Search
None
See application file for complete search history.

(56) References Cited

U.S. PATENT DOCUMENTS

| | | | | |
|---|---|---|---|---|
| 7,314,849 | B2 * | 1/2008 | Balko et al. | 504/244 |
| 7,622,641 | B2 * | 11/2009 | McCutchen et al. | 800/300 |
| 2009/0062121 | A1 | 3/2009 | Satchivi et al. | |
| 2010/0137137 | A1 | 6/2010 | Rosinger et al. | |
| 2011/0082162 | A1 * | 4/2011 | Lorsbach et al. | 514/274 |
| 2011/0207607 | A1 * | 8/2011 | Satchivi et al. | 504/105 |
| 2012/0115727 | A1 | 5/2012 | Satchivi et al. | |
| 2012/0190551 | A1 * | 7/2012 | Yerkes et al. | 504/242 |
| 2013/0109569 | A1 * | 5/2013 | Dave et al. | 504/130 |
| 2013/0310256 | A1 * | 11/2013 | Yerkes et al. | 504/103 |
| 2014/0031210 | A1 * | 1/2014 | Yerkes et al. | 504/103 |
| 2014/0031211 | A1 * | 1/2014 | Yerkes et al. | 504/103 |
| 2014/0031212 | A1 * | 1/2014 | Yerkes et al. | 504/103 |
| 2014/0031213 | A1 * | 1/2014 | Yerkes et al. | 504/103 |
| 2014/0031214 | A1 * | 1/2014 | Yerkes et al. | 504/103 |
| 2014/0031215 | A1 * | 1/2014 | Yerkes et al. | 504/103 |
| 2014/0031216 | A1 * | 1/2014 | Yerkes et al. | 504/103 |
| 2014/0031217 | A1 * | 1/2014 | Yerkes et al. | 504/103 |
| 2014/0031219 | A1 * | 1/2014 | Yerkes et al. | 504/103 |
| 2014/0031220 | A1 * | 1/2014 | Yerkes et al. | 504/103 |
| 2014/0031221 | A1 * | 1/2014 | Yerkes et al. | 504/103 |
| 2014/0031222 | A1 * | 1/2014 | Yerkes et al. | 504/103 |
| 2014/0031227 | A1 * | 1/2014 | Yerkes et al. | 504/128 |
| 2014/0031228 | A1 * | 1/2014 | Mann et al. | 504/130 |
| 2014/0031229 | A1 * | 1/2014 | Mann et al. | 504/136 |

FOREIGN PATENT DOCUMENTS

WO    WO 2007082098    *    7/2007

OTHER PUBLICATIONS

Synthesis of Esters: Esterification Reactions, obtained via google.com in U.S. Appl. No. 13/840,306, obtained online Mar. 8, 2014.*
Steglich Esterification Reactions, Organic Chemistry Portal in U.S. Appl. No. 13/840,306.*
Chui, M.P., Non-Final Office Action in U.S. Appl. No. 13/840,306, Mar. 13, 2014, pp. 1-12, USPTO.*

(Continued)

*Primary Examiner* — Alton Pryor
(74) *Attorney, Agent, or Firm* — Faegre Baker Daniels LLP

(57) ABSTRACT

Provided herein are synergistic herbicidal compositions comprising (a) a compound of formula (I):

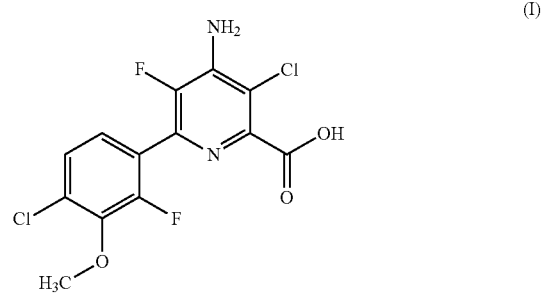

or an agriculturally acceptable salt or ester thereof and (b) a sulfonylurea e.g., amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl or trifloxysulfuron-sodium, or an agriculturally acceptable salt or ester thereof. The compositions and methods provide control of undesirable vegetation, e.g., in crops and other settings, e.g., in direct-seeded, water-seeded and transplanted rice, cereals, wheat, barley, oats, rye, sorghum, corn or maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights-of-way (ROW).

14 Claims, No Drawings

(56) References Cited

OTHER PUBLICATIONS

Pryor, A.N., Notice of Allowance and Fee(s) Due for U.S. Appl. No. 13/832,978, Apr. 9, 2014, pp. 1-13, USPTO.*
Pryor, A.N., Notice of Allowance and Fee(s) Due for U.S. Appl. No. 13/833,315, May 12, 2014, pp. 1-8, USPTO.*
Pryor, A.N., Notice of Allowance and Fee(s) Due for U.S. Appl. No. 13/833,315, Mar. 20, 2014, pp. 1-11, USPTO.*
Pryor, A.N., Notice of Allowance and Fee(s) Due for U.S. Appl. No. 13/833,362, May 29, 2014, pp. 1-8, USPTO.*
Pryor, A.N., Notice of Allowance and Fee(s) Due for U.S. Appl. No. 13/833,372, May 14, 2014, pp. 1-8, USPTO.*
Pryor, A.N., Notice of Allowance and Fee(s) Due for U.S. Appl. No. 13/833,659, Mar. 17, 2014, pp. 1-12, USPTO.*
Pryor, A.N., Notice of Allowance and Fee(s) Due for U.S. Appl. No. 13/833,923, May 2, 2014, pp. 1-9, USPTO.*
Pryor, A.N., Notice of Allowance and Fee(s) Due for U.S. Appl. No. 13/833,965, Apr. 1, 2014, pp. 1-8, USPTO.*
Pryor, A.N., Notice of Allowance and Fee(s) Due for U.S. Appl. No. 13/834,326, May 13, 2014, pp. 1-4, USPTO.*
Pryor, A.N., Notice of Allowance and Fee(s) Due for U.S. Appl. No. 13/834,326, Apr. 2, 2014, pp. 1-9, USPTO.*
Pryor, A.N., Notice of Allowance and Fee(s) Due for U.S. Appl. No. 13/836,653, Apr. 2, 2014, pp. 1-8, USPTO.*
Pryor, A.N., Notice of Allowance and Fee(s) Due for U.S. Appl. No. 13/834,706, Mar. 12, 2014, pp. 1-13, USPTO.*
Pryor, A.N., Notice of Allowance and Fee(s) Due for U.S. Appl. No. 13/839,043, May 27, 2014, pp. 1-5, USPTO.*
Pryor, A.N., Notice of Allowance and Fee(s) Due for U.S. Appl. No. 13/839,043, Mar. 24, 2014, pp. 1-8, USPTO.*
Pryor, A.N., Notice of Allowance and Fee(s) Due for U.S. Appl. No. 13/840,236, Apr. 25, 2014, pp. 1-8, USPTO.*
Pryor, A.N., Notice of Allowance and Fee(s) Due for U.S. Appl. No. 13/840,303, Apr. 25, 2014, pp. 1-8, USPTO.*
Pryor, A.N., Notice of Allowance and Fee(s) Due for U.S. Appl. No. 13/840,346, Jun. 4, 2014, pp. 1-8, USPTO.*
Pryor, A.N., Notice of Allowance and Fee(s) Due for U.S. Appl. No. 13/840,419, May 5, 2014, pp. 1-8, USPTO.*
Pryor, A.N., Notice of Allowance and Fee(s) Due for U.S. Appl. No. 13/840,488, May 2, 2014, pp. 1-8, USPTO.*
Thomas, S, Written Opinion of the International Search Authority for PCT/US2013/051323, Dec. 6, 2013, pp. 1-5, ISA/US.
Thomas, S, International Search Report for PCT/US2013/051323, Dec. 6, 2013, pp. 1-4, ISA/US.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND CERTAIN SULFONYLUREAS

PRIORITY CLAIM

This application claims the benefit of U.S. provisional patent application No. 61/675,117 filed on Jul. 24, 2012, this provisional application is incorporated herein by reference in its entirety.

FIELD

Provided herein are herbicidal compositions comprising, as well as methods of controlling undersirable vegetation utilizing: (a) 4-amino-3-chloro-5-fluoro-6-(4-chloro-2-fluoro-3-methoxyphenyl)pyridine-2-carboxylic acid or an agriculturally acceptable ester or salt thereof and (b) a sulfonylurea selected from the group consisting of amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl and trifloxysulfuron-sodium, or an agriculturally acceptable salt or ester thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

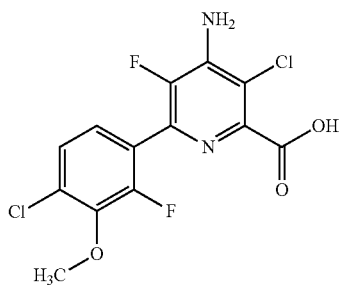

or an agriculturally acceptable salt or ester thereof, and (b) at least one a sulfonylurea and agriculturally acceptable salts and esters thereof.

A second embodiment includes the mixture of the first embodiment in which of formula (I), is present in the form of at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixture according to either the first or second embodiments wherein the (b) at least one sulfonylurea selected from the group consisting of: amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl or trifloxysulfuron-sodium, or an agriculturally acceptable salt, carboxylic acid, carboxylate salt, or ester thereof of at least one of the aforementioned dimethoxypyrimidines.

A fourth embodiment includes the mixtures according to any of the first, second, or third embodiments in which the sulfonylurea in the mixture is amidosulfuron wherein the weight ratio of the compound of formula (I) to amidosulfuron given in units of gae/ha to gai/ha or gae/ha to gae/ha is selected from the group of ranges of ratios and ratios consisting of about: 1:1.1 or within any range defined between any pair of the foregoing values.

A fifth embodiment includes the mixtures according to any of the first, second, or third embodiments in which the sulfonylurea in the mixture is azimsulfuron wherein the weight ratio of the compound of formula (I) to azimsulfuron given in units of gae/ha to gai/ha or gae/ha to gae/ha is selected from the group of ranges of ratios and ratios consisting of about: 1:4.1, 1:1.4, 1:2.9, 3.5:1, 7:1, 2.8:1, 1:5.7, 14:1, from 1:5.7 to 7:1, from 1.4:1 to 1:2.9, from 2.8:1 to 1:1.4, from 3.5:1 to 14:1, from 1.4:1 to 2.8:1, from 14:1 to 1:5.7, or within any range defined between any pair of the foregoing values.

A sixth embodiment includes the mixtures according to any of the first, second, or third embodiments in which the sulfonylurea in the mixture is bensulfuron-methyl wherein the weight ratio of the compound of formula (I) to bensulfuron-methyl given in units of gae/ha to gai/ha or gae/ha to gae/ha is selected from the group of ranges of ratios and ratios consisting of about: 1.4:1, 2.8:1, 1:1.4, 4.4:1, 1:1, 1:2, 1:4, 1:8, 1:16, 3:1, 2:1, 1:1.7, 1:1.5, 1:4.4, 5.5:1, 1:2.2, 1:8.8, from 1.4:1 to 5.5:1, from 1:2.2 to 1:8.8, from 2.8:1 to 1:1.4, from 1:4 to 2:1, from 1:1 to 1:8, from 1:2 to 1:8, from 4.4:1 to 1:16, from 3:1 to 1:16, from 1:16 to 5.5:1, or within any range defined between any pair of the foregoing values.

A seventh embodiment includes the mixtures according to any of the first, second, or third embodiments in which the sulfonylurea in the mixture is chlorsulfuron wherein the weight ratio of the compound of formula (I) to chlorsulfuron given in units of gae/ha to gai/ha or gae/ha to gae/ha is selected from the group of ranges of ratios and ratios consisting of about: 4:1, or within any range defined between any pair of the foregoing values.

An eighth embodiment includes the mixtures according to any of the first, second, or third embodiments in which the sulfonylurea in the mixture is cyclosulfamuron wherein the weight ratio of the compound of formula (I) to cyclosulfamuron given in units of gae/ha to gai/ha or gae/ha to gae/ha is selected from the group of ranges of ratios and ratios consisting of about: 1:1.6, 1.3:1, 2.6:1, from 1:1.6 to 2.6:1, from 1.3:1 to 1:1.6, or within any range defined between any pair of the foregoing values.

A ninth embodiment includes the mixtures according to any of the first, second, or third embodiments in which the sulfonylurea in the mixture is ethametsulfuron-methyl wherein the weight ratio of the compound of formula (I) to ethametsulfuron-methyl given in units of gae/ha to gai/ha or gae/ha to gae/ha is selected from the group of ranges of ratios and ratios consisting of about: from 1:15 to 68:1, from 1:9 to 8:1, or within any range defined between any pair of the foregoing values.

A tenth embodiment includes the mixtures according to any of the first, second, or third embodiments in which the sulfonylurea in the mixture is ethoxysulfuron wherein the weight ratio of the compound of formula (I) to ethoxysulfuron given in units of gae/ha to gai/ha or gae/ha to gae/ha is selected from the group of ranges of ratios and ratios consisting of about: 1.1:1, 1:1.9, 1:3.8, 1:8.8, 1:4.4, 2.1:1, 2.3:1, 1.2:1, 1.4:1, 2.8:1, 5.7:1, 1:1.7, 1:3.4, from 2.3:1 to 1.2:1, from 1:1.7 to 1:3.4, from 1.4:1 to 5.7:1, from 2.1:1 to 1:1.9, from 2.1:1 to 1:8.8, from 5.7:1 to 1:8.8, or within any range defined between any pair of the foregoing values.

An eleventh embodiment includes the mixtures according to any of the first, second, or third embodiments in which the sulfonylurea in the mixture is flazasulfuron wherein the weight ratio of the compound of formula (I) to flazasulfuron given in units of gae/ha to gai/ha or gae/ha to gae/ha is selected from the group of ranges of ratios and ratios consisting of about: 1:3.1, 1:6.3, 1:12.5, 1.3:1, and from 1:3.1 to 1:12.5, or within any range defined between any pair of the foregoing values.

A twelfth embodiment includes the mixtures according to any of the first, second, or third embodiments in which the sulfonylurea in the mixture is flucetosulfuron wherein the weight ratio of the compound of formula (I) to flucetosulfuron given in units of gae/ha to gai/ha or gae/ha to gae/ha is selected from the group of ranges of ratios and ratios consisting of about: 350:1, 175:1, 88:1, 44:1, 22:1, 19:1, 8.8:1, 3.2:1, 1.6:1, 1:1.25, 9.4:1, 4.7:1, 6.4:1, from 88:1 to 350:1, from 4.7:1 to 19.1, from 1:125 to 3.2:1, from 350:1 to 22.1; and from 350:1 to 1:1.25, or within any range defined between any pair of the foregoing values.

A thirteenth embodiment includes the mixtures according to any of the first, second, or third embodiments in which the sulfonylurea in the mixture is flupyrsulfuron-methyl sodium wherein the weight ratio of the compound of formula (I) to flupyrsulfuron-methyl sodium given in units of gae/ha to gai/ha or gae/ha to gae/ha is selected from the group of ranges of ratios and ratios consisting of about: 1.75:1, or within any range defined between any pair of the foregoing values.

A fourteenth embodiment includes the mixtures according to any of the first, second, or third embodiments in which the sulfonylurea in the mixture is foramsulfuron wherein the weight ratio of the compound of formula (I) to foramsulfuron given in units of gae/ha to gai/ha or gae/ha to gae/ha is selected from the group of ranges of ratios and ratios consisting of about: 1:2.5, 1:5, from 1:2.5 to 1:5, or within any range defined between any pair of the foregoing values.

A fifteenth embodiment includes the mixtures according to any of the first, second, or third embodiments in which the sulfonylurea in the mixture is imazosulfuron wherein the weight ratio of the compound of formula (I) to imazosulfuron given in units of gae/ha to gai/ha or gae/ha to gae/ha is selected from the group of ranges of ratios and ratios consisting of about: 1:1.2, 1:2.4, 1:4.8, 1:9.6, 1:19, 1:56, 1:38, 1:1.3, 1:2.6, 1:5.1, 1:10.3, from 1:1.3 to 1.5:1, from 1:2.6 to 1:38, from 1:19 to 1:56, from 1:1.2 to 1:56, from 1:1.2 to 1:2.4, and from 1:1.2 to 1:9.6, or within any range defined between any pair of the foregoing values.

A sixteenth embodiment includes the mixtures according to any of the first, second, or third embodiments in which the sulfonylurea in the mixture is iodosulfuron-methyl sodium wherein the weight ratio of the compound of formula (I) to iodosulfuron-methyl sodium given in units of gae/ha to gai/ha or gae/ha to gae/ha is selected from the group of ranges of ratios and ratios consisting of about: 1.6:1, 3.2:1, 3.5:1, 6.4:1, 12.8:1, and from 1.6:1 to 12.8:1, or within any range defined between any pair of the foregoing values.

A seventeenth embodiment includes the mixtures according to any of the first, second, or third embodiments in which the sulfonylurea in the mixture is iofensulfuron wherein the weight ratio of the compound of formula (I) to iofensulfuron given in units of gae/ha to gai/ha or gae/ha to gae/ha is selected from the group of ranges of ratios and ratios consisting of about: 1:25 to about 600:1, from about 1:9 to about 75:1, or within any range defined between any pair of the foregoing values.

A eighteenth embodiment includes the mixtures according to any of the first, second, or third embodiments in which the sulfonylurea in the mixture is mesosulfuron-methyl wherein the weight ratio of the compound of formula (I) to mesosulfuron-methyl given in units of gae/ha to gai/ha or gae/ha to gae/ha is selected from the group of ranges of ratios and ratios consisting of about: 1:8 to 300:1, from 1:2 to 50:1, from 1:1 to 8:1, from 2:1 to 4:1, 2.9:1, or within any range defined between any pair of the foregoing values.

A nineteenth embodiment includes the mixtures according to any of the first, second, or third embodiments in which the sulfonylurea in the mixture is metsulfuron-methyl wherein the weight ratio of the compound of formula (I) to metsulfuron-methyl given in units of gae/ha to gai/ha or gae/ha to gae/ha is selected from the group of ranges of ratios and ratios consisting of about: 1:1.7, 1.2:1, 2.3:1, 1:3.4, 1.4:1, 2.8:1, 5.6:1, 8:1, from 1.4:1 to 5.6:1, from 1:3.4 to 8:1, from 1:3.4 to 2.3:1, or within any range defined between any pair of the foregoing values.

A twentieth embodiment includes the mixtures according to any of the first, second, or third embodiments in which the sulfonylurea in the mixture is nicosulfuron wherein the weight ratio of the compound of formula (I) to nicosulfuron given in units of gae/ha to gai/ha or gae/ha to gae/ha is selected from the group of ranges of ratios and ratios consisting of about: 1.2:1, 2.4:1, 1:1, 1:2, 1:4, 1:1.7, 1:3.3, 1:6.6, 2.4:1, from 2.4 to 1:6.6, and from 1:1.7 to 1:6.6, from 1:1.7 to 2.4:1, from 1.2:1 to 1:3.3, from 1:1 to 1:4, from 2.4:1 to 1:6.6, or within any range defined between any pair of the foregoing values.

A twenty-first embodiment includes the mixtures according to any of the first, second, or third embodiments in which the sulfonylurea in the mixture is orthosulfamuron wherein the weight ratio of the compound of formula (I) to orthosulfamuron given in units of gae/ha to gai/ha or gae/ha to gae/ha is selected from the group of ranges of ratios and ratios consisting of about: 1:1.7, 1.2:1, 1:3.4, 2.3:1, 1:6.9, 1:1.4, 1.4:1, from 1:1.4 to 1.4:1, from 1:1.7 to 1.2:1, from 1:1 to 1:6.9, from 1:3.4 to 2.3:1, and from 1:1.7 to 1:6.9, or within any range defined between any pair of the foregoing values.

A twenty-second embodiment includes the mixtures according to any of the first, second, or third embodiments in which the sulfonylurea in the mixture is primisulfuron-methyl wherein the weight ratio of the compound of formula (I)

to primisulfuron-methyl given in units of gae/ha to gai/ha or gae/ha to gae/ha is selected from the group of ranges of ratios and ratios consisting of about: 1:1.9, 1:3.8, and from 1:1.9 to 1:3.8, or within any range defined between any pair of the foregoing values.

A twenty-third embodiment includes the mixtures according to any of the first, second, or third embodiments in which the sulfonylurea in the mixture is propyrisulfuron wherein the weight ratio of the compound of formula (I) to propyrisulfuron given in units of gae/ha to gai/ha or gae/ha to gae/ha is selected from the group of ranges of ratios and ratios consisting of about: 1:2.6, 1:5.1, 1:10.3, 1:1.3, 1:1.4, 1.4:1, 2.8:1, 1:2.8, 1:5.6, from 1:10.3 to 2.8:1, from 1:5.6 to 2.8:1, from 1:2.6 to 1:10.3, or within any range defined between any pair of the foregoing values.

A twenty-fourth embodiment includes the mixtures according to any of the first, second, or third embodiments in which the sulfonylurea in the mixture is prosulfuron wherein the weight ratio of the compound of formula (I) to prosulfuron given in units of gae/ha to gai/ha or gae/ha to gae/ha is selected from the group of ranges of ratios and ratios consisting of about: 1:20 to about 68:1, from about 1:14 to about 8:1, or within any range defined between any pair of the foregoing values.

A twenty-fifth embodiment includes the mixtures according to any of the first, second, or third embodiments in which the sulfonylurea in the mixture is pyrimisulfan wherein the weight ratio of the compound of formula (I) to pyrimisulfan given in units of gae/ha to gai/ha or gae/ha to gae/ha is selected from the group of ranges of ratios and ratios consisting of about: 1:100 to about 30:1, from about 1:45 to about 10:1, or within any range defined between any pair of the foregoing values.

A twenty-sixth embodiment includes the mixtures according to any of the first, second, or third embodiments in which the sulfonylurea in the mixture is pyroxasulfone wherein the weight ratio of the compound of formula (I) to pyroxasulfone given in units of gae/ha to gai/ha or gae/ha to gae/ha is selected from the group of ranges of ratios and ratios consisting of about: from about 1:500 to about 3:1, from about 1:136 to about 1:2, or within any range defined between any pair of the foregoing values.

A twenty-seventh embodiment includes the mixtures according to any of the first, second, or third embodiments in which the sulfonylurea in the mixture is rimsulfuron wherein the weight ratio of the compound of formula (I) to rimsulfuron given in units of gae/ha to gai/ha or gae/ha to gae/ha is selected from the group of ranges of ratios and ratios consisting of about: 1:1, 4:1, 2:1, 1:2, 1.2:1, 2.4:1, 4.8:1, 9.7:1, 1:1.7, 1:2, 8:1, from 1:1.7 to 9.7:1, from 1:2 to 4:1, from 1:1.7 to 4.8:1, and from 1:2 to 8:1, or within any range defined between any pair of the foregoing values.

A twenty-eighth embodiment includes the mixtures according to any of the first, second, or third embodiments in which the sulfonylurea in the mixture is sulfometuron-methyl wherein the weight ratio of the compound of formula (I) to sulfometuron-methyl given in units of gae/ha to gai/ha or gae/ha to gae/ha is selected from the group of ranges of ratios and ratios consisting of about: 1:4.4, 1:2.2, and 1:1.1, or within any range defined between any pair of the foregoing values.

A twenty-ninth embodiment includes the mixtures according to any of the first, second, or third embodiments in which the sulfonylurea in the mixture is sulfosulfuron wherein the weight ratio of the compound of formula (I) to sulfosulfuron given in units of gae/ha to gai/ha or gae/ha to gae/ha is selected from the group of ranges of ratios and ratios consisting of about: 1:1, or within any range defined between any pair of the foregoing values.

A thirtieth embodiment includes the mixtures according to any of the first, second, or third embodiments in which the sulfonylurea in the mixture is thifensulfuron-methyl wherein the weight ratio of the compound of formula (I) to thifensulfuron-methyl given in units of gae/ha to gai/ha or gae/ha to gae/ha is selected from the group of ranges of ratios and ratios consisting of about: 2.3:1, or within any range defined between any pair of the foregoing values.

A thirty-first embodiment includes the mixtures according to any of the first, second, or third embodiments in which the sulfonylurea in the mixture is triafamone wherein the weight ratio of the compound of formula (I) to triafamone given in units of gae/ha to gai/ha or gae/ha to gae/ha is selected from the group of ranges of ratios and ratios consisting of about: from 1:25 to 60:1, from 1:23 to 30:1, or within any range defined between any pair of the foregoing values.

A thirty-second embodiment includes the mixtures according to any of the first, second, or third embodiments in which the sulfonylurea in the mixture is triasulfuron wherein the weight ratio of the compound of formula (I) to triasulfuron given in units of gae/ha to gai/ha or gae/ha to gae/ha is selected from the group of ranges of ratios and ratios consisting of about: 1:15 to 136:1, from 1:7 to 16:1, or within any range defined between any pair of the foregoing values.

A thirty-third embodiment includes the mixtures according to any of the first, second, or third embodiments in which the sulfonylurea in the mixture is tribenuron-methyl wherein the weight ratio of the compound of formula (I) to tribenuron-methyl given in units of gae/ha to gai/ha or gae/ha to gae/ha is selected from the group of ranges of ratios and ratios consisting of about: 4:1, or within any range defined between any pair of the foregoing values.

A thirty-fourth embodiment includes the mixtures according to any of the first, second, or third embodiments in which the sulfonylurea in the mixture is trifloxysulfuron-sodium. wherein the weight ratio of the compound of formula (I) to trifloxysulfuron-sodium. given in units of gae/ha to gai/ha or gae/ha to gae/ha is selected from the group of ranges of ratios and ratios consisting of about: 1:3, 1:1.5, 1.3:1, and from 1:3 to 1.3:1, or within any range defined between any pair of the foregoing values.

A thirty-fifth embodiment includes any composition according to any of the first through the thirty-fourth embodiments wherein the mixture further comprises at least one an agriculturally acceptable agent selected from the group consisting of an adjuvant.

A thirty-sixth embodiment includes any composition according to any of the first through the thirty-fifth embodiments wherein the mixture further comprises at least one an agriculturally acceptable agent selected from the group consisting of a carrier, or a safener.

A thirty-seventh embodiment includes any composition according to any of the first through the thirty-sixth embodiments wherein the mixture further comprises at least one an agriculturally acceptable agent selected from the group consisting of a safener.

A thirty-eighth embodiment includes any composition according to any of the first through the thirty-fourth embodiments wherein the mixture further comprises at least one an agriculturally acceptable agent selected from the group consisting of an adjuvant, a carrier, or a safener.

A thirty-ninth embodiment includes methods of controlling undesirable vegetation comprising the steps of applying or otherwise contacting vegetation and/or soil, and/or water with a herbicidally effective amount of at least one mixture according to any of the first through the thirty-eighth embodiments.

A fortieth embodiment includes methods according to the tenth embodiment wherein undesirable vegetation is controlled according to at least technique selected from the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A forty-first embodiment includes methods according to either of the thirty-ninth and fortieth embodiments wherein a herbicidally effective amount of the mixture is applied post emergently to at least one of the following: a crop, a field, a ROW, or a paddy.

A forty-second embodiment includes methods according to either of the thirty-ninth and fortieth embodiments wherein a herbicidally effective amount of the mixture is applied pre-emergently to at least one of the following: a crop, a field, a ROW, or a paddy.

A forty-third embodiment includes methods according to any of the thirty-ninth through forty-second embodiments wherein a herbicidally effective amount of the mixture is applied either pre- or post emergently to at least one of the following: a crop, a field, a ROW, or a paddy.

A forty-fourth embodiment includes methods according to any of the forty-first through the forty-third embodiments wherein the undesirable vegetation controlled by an application of a herbicidally effective amount of the mixture and at least one of the following phytotoxic actives: glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

A forty-fifth embodiment includes a at least one method according to any of the forty-first through the forty-fourth embodiments wherein a plant that is tolerant to at least one herbicide is treated, and where the tolerant crop possesses multiple or stacked traits conferring tolerance to multiple herbicides or inhibitors of multiple modes of action, in some embodiments the treated plant that expresses resistance to a herbicide is a itself undesirable vegetation.

A forty-sixth embodiment includes methods according to the forty-fifth embodiment, wherein the resistant or tolerant weed is a biotype with resistance or tolerance to multiple herbicides, multiple chemical classes, inhibitors of multiple herbicide modes-of-action, or via multiple resistance mechanisms.

A forty-seventh embodiment includes at least one of the methods according to either the forty-fifth or forty-sixth embodiments, wherein the resistant or tolerant undesirable plant is a biotype resistant or tolerant to at least on agent selected from the groups consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A forty-eighth embodiment includes methods of controlling undesirable vegetation comprising the step of applying a herbicidally effective amount of at least one mixture according to the fourth embodiment wherein the amount of the mixture is applied at a rate, expressed in gai/ha or gae/ha of amidosulfuron selected from the group of rates and ranges of rates consisting of about: 10 or within any range defined between any pair of the foregoing values.

A forty-ninth embodiment includes methods according to either of the fourth and forty-eighth embodiments wherein the controlled plant is at least one plant selected from the group consisting of: GALAP, LAMPU, VERDE, still other embodiments include controlling plants from the genera consisting of: *Galium, Lamium, Veronica.*

A fiftieth embodiment includes methods of controlling undesirable vegetation comprising the step of applying a herbicidally effective amount of at least one mixture according to the fifth embodiment wherein the amount of the mixture is applied at a rate, expressed in gai/ha or gae/ha of azimsulfuron selected from the group of rates and ranges of rates consisting of about: 2.5, 3.13, 5, 6.25, 12.5, 25, 3.13 to 12.5, and 2.5 to 25, or within any range defined between any pair of the foregoing values.

A fifty-first embodiment includes methods according to either of the fifth and fiftieth embodiments wherein the controlled plant is at least one plant selected from the group consisting of: BRAPP, LEFCH, SCPMA, and ECHOR, still other embodiments include controlling plants from the genera consisting of: *Brachiaria, Leptochloa, Schoenoplectus, Bolboschoenus, Echinochloa.*

A fifty-second embodiment includes methods of controlling undesirable vegetation comprising the step of applying a herbicidally effective amount of at least one mixture according to the sixth embodiment wherein the amount of the mixture is applied at a rate, expressed in gai/ha or gae/ha of bensulfuron-methyl selected from the group of rates and ranges of rates consisting of about: 3.125, 6.25, 4.38, 8.75, 17.5, 35, 70, from 3.125 to 6.25, from 4.38 to 17.5, and from 4.38 to 35, or within any range defined between any pair of the foregoing values.

A fifty-third embodiment includes methods according to either of the sixth and fifty-second embodiments wherein the controlled plant is at least one plant selected from the group consisting of: ECHOR, LEFCH, BRAPP, ECHCG, ISCRU, SCPMA, still other embodiments include controlling plants from the genera consisting of: *Echinochloa, Leptochloa, Brachiaria, Ischaemum, Schoenoplectus, Bolboschoenus.*

A fifty-fourth embodiment includes methods of controlling undesirable vegetation comprising the step of applying a herbicidally effective amount of at least one mixture according to the seventh embodiment wherein the amount of the mixture is applied at a rate, expressed in gai/ha or gae/ha of chlorsulfuron selected from the group of rates and ranges of rates consisting of about: 2.2 or within any range defined between any pair of the foregoing values.

A fifty-fifth embodiment includes methods according to either of the seventh and fifty-fourth embodiments wherein the controlled plant is at least one plant selected from the group consisting of: VIOTR, CIRAR, still other embodiments include controlling plants from the genera consisting of: *Viola, Cirsium*.

A fifty-sixth embodiment includes methods of controlling undesirable vegetation comprising the step of applying a herbicidally effective amount of at least one mixture according to the eighth embodiment wherein the amount of the mixture is applied at a rate, expressed in gai/ha or gae/ha of cyclosulfamuron selected from the group of rates and ranges of rates consisting of about: 12.5, or within any range defined between any pair of the foregoing values.

A fifty-seventh embodiment includes methods according to either of the eighth and fifty-sixth embodiments wherein the controlled plant is at least one plant selected from the group consisting of: CYPIR, SCPMA, still other embodiments include controlling plants from the genera consisting of: *Cirsium, Schoenoplectus, Bolboschoenus*.

A fifty-eighth embodiment includes methods of controlling undesirable vegetation comprising the step of applying a herbicidally effective amount of at least one mixture according to the ninth embodiment wherein the amount of the mixture is applied at a rate, expressed in gai/ha or gae/ha of ethametsulfuron-methyl selected from the group of rates and ranges of rates consisting of about: from 6 to 300, from 7 to 55, or within any range defined between any pair of the foregoing values.

A fifth-ninth embodiment includes methods according to either of the ninth and fifty-eighth embodiments used in herbicidally effective rates for controlling the growth of undesirable plants that have a negative impact on the growth of various crop plants.

A sixtieth embodiment includes methods of controlling undesirable vegetation comprising the step of applying a herbicidally effective amount of at least one mixture according to the tenth embodiment wherein the amount of the mixture is applied at a rate, expressed in gai/ha or gae/ha of ethoxysulfuron selected from the group of rates and ranges of rates consisting of about: 7.5, 15, 30, from 7.5 to 15, and from 7.5 to 30, or within any range defined between any pair of the foregoing values.

A sixty-first embodiment includes methods according to either of the tenth and sixtieth embodiments wherein the controlled plant is at least one plant selected from the group consisting of: CYPIR, BRAPP, ISCRU, ECHOR, LEFCH still other embodiments include controlling plants from the genera consisting of: *Cyperus, Brachiaria, Ischaemum, Echinochloa, Leptochloa*.

A sixty-second embodiment includes methods of controlling undesirable vegetation comprising the step of applying a herbicidally effective amount of at least one mixture according to the eleventh embodiment wherein the amount of the mixture is applied at a rate, expressed in gai/ha or gae/ha of flazasulfuron selected from the group of rates and ranges of rates consisting of about: 25, 50, 100, from 25 to 50, from 50 to 100, and from 25 to 100, or within any range defined between any pair of the foregoing values.

A sixty-third embodiment includes methods according to either of the eleventh and sixty-second embodiments wherein the controlled plant is at least one plant selected from the group consisting of: IPOHE, LEFCH, still other embodiments include controlling plants from the genera consisting of: *Ipomoea, Leptochloa*.

A sixty-fourth embodiment includes methods of controlling undesirable vegetation comprising the step of applying a herbicidally effective amount of at least one mixture according to the twelfth embodiment wherein the amount of the mixture is applied at a rate, expressed in gai/ha or gae/ha of flucetosulfuron selected from the group of rates and ranges of rates consisting of about: 0.05, 0.10, 0.20, 1.7, 5, 10, from 0.05 to 0.20, from 5 to 0 10, and from 0.05 to 10, or within any range defined between any pair of the foregoing values.

A sixth-fifth embodiment includes methods according to either of the twelfth and sixty-fourth embodiments wherein the controlled plant is at least one plant selected from the group consisting of: LEFCH, IPOHE, CYPIR, BRAPP, and SCPSU, still other embodiments include controlling plants from the genera consisting of: *Ipomoea, Leptochloa, Cyperus, Brachiaria, Schoenoplectus, Bolboschoenus*.

A sixty-sixth embodiment includes methods of controlling undesirable vegetation comprising the step of applying a herbicidally effective amount of at least one mixture according to the thirteenth embodiment wherein the amount of the mixture is applied at a rate, expressed in gai/ha or gae/ha of flupyrsulfuron-methyl sodium selected from the group of rates and ranges of rates consisting of about: 5 or within any range defined between any pair of the foregoing values.

A sixty-seventh embodiment includes methods according to either of the thirteenth and sixty-sixth embodiments wherein the controlled plant is at least one plant selected from the group consisting of: VERPE, CIRAR, still other embodiments include controlling plants from the genera consisting of: *Veronica, Cirsium*.

A sixty-eighth embodiment includes methods of controlling undesirable vegetation comprising the step of applying a herbicidally effective amount of at least one mixture according to the fourteenth embodiment wherein the amount of the mixture is applied at a rate, expressed in gai/ha or gae/ha of foramsulfuron selected from the group of rates and ranges of rates consisting of about: 20, 40, and from 20 to 40, or within any range defined between any pair of the foregoing values.

A sixty-ninth embodiment includes methods according to either of the fourteenth and sixty-eighth embodiments wherein the controlled plant is at least one plant selected from the group consisting of: LEFCH, still other embodiments include controlling plants from the genera consisting of: *Leptochloa*.

A seventieth embodiment includes methods of controlling undesirable vegetation comprising the step of applying a herbicidally effective amount of at least one mixture according to the fifteenth embodiment wherein the amount of the mixture is applied at a rate, expressed in gai/ha or gae/ha of imazosulfuron selected from the group of rates and ranges of rates consisting of about: 21, 42, 84, 22.5, 45, 168, from 22.5 to 168, from 21 to 42, or within any range defined between any pair of the foregoing values.

A seventy-first embodiment includes methods according to either of the fifteenth and seventieth embodiments wherein the controlled plant is at least one plant selected from the group consisting of: DIGSA, LEFCH, ECHCO, SCPMA, still other embodiments include controlling plants from the genera consisting of: *Digitaria, Leptochloa, Echinochloa, Schoenoplectus, Bolboschoenus*.

A seventy-second embodiment includes methods of controlling undesirable vegetation comprising the step of applying a herbicidally effective amount of at least one mixture according to the sixteenth embodiment wherein the amount of the mixture is applied at a rate, expressed in gai/ha or gae/ha of iodosulfuron-methyl sodium selected from the group of rates and ranges of rates consisting of about: 5, 2.5, and from 2.5 to 5, or within any range defined between any pair of the foregoing values.

A seventy-third embodiment includes methods according to either of the sixteenth and seventy-second embodiments wherein the controlled plant is at least one plant selected from the group consisting of: IPOHE, VIOTR, MATCH, CIRAR, still other embodiments include controlling plants from the genera consisting of: *Ipomoea, Viola, Chamomilla, Cirsium.*

A seventy-fourth embodiment includes methods of controlling undesirable vegetation comprising the step of applying a herbicidally effective amount of at least one mixture according to the seventeenth embodiment wherein the amount of the mixture is applied at a rate, expressed in gai/ha or gae/ha of iofensulfuron selected from the group of rates and ranges of rates consisting of about: from 315 to 3, from 10 to 65, from 1 to 15, from 2 to 300, from 1 to 8, from 3.5 to 20, from 2 to 4, from 7 to 10, from 3 to 8.75, 3, or within any range defined between any pair of the foregoing values.

A seventy-fifth embodiment includes methods according to either of the seventeenth and seventy-fourth used in herbicidally effective rates for controlling the growth of undesirable plants that have a negative impact on the growth of various crop plants.

A seventy-sixth embodiment includes methods of controlling undesirable vegetation comprising the step of applying a herbicidally effective amount of at least one mixture according to the eighteenth embodiment wherein the amount of the mixture is applied at a rate, expressed in gai/ha or gae/ha of mesosulfuron-methyl selected from the group of rates and ranges of rates consisting of about: 8.75, from 3, 2 to 4, or within any range defined between any pair of the foregoing values.

A seventy-seventh embodiment includes methods according to either of the eighteenth and seventy-sixth embodiments wherein the controlled plant is at least one plant selected from the group consisting of: VERPE, MATCH, CIRAR, still other embodiments include controlling plants from the genera consisting of: *Veronica, Chamomilla, Cirsium.*

A seventy-eighth embodiment includes methods of controlling undesirable vegetation comprising the step of applying a herbicidally effective amount of at least one mixture according to the nineteenth embodiment wherein the amount of the mixture is applied at a rate, expressed in gai/ha or gae/ha of metsulfuron-methyl selected from the group of rates and ranges of rates consisting of about: 7.5, 15, 1.1, from 1.1 to 15, from 7.5 to 15, or within any range defined between any pair of the foregoing values.

A seventy-ninth embodiment includes methods according to either of the ninteenth and seventy-eighth embodiments wherein the controlled plant is at least one plant selected from the group consisting of: BRAPP, ECHOR, MATCH, CIRAR, still other embodiments include controlling plants from the genera consisting of: *Cirsium, Chamomilla, Echinochloa, Brachiaria.*

An eightieth embodiment includes methods of controlling undesirable vegetation comprising the step of applying a herbicidally effective amount of at least one mixture according to the twentieth embodiment wherein the amount of the mixture is applied at a rate, expressed in gai/ha or gae/ha of nicosulfuron selected from the group of rates and ranges of rates consisting of about: 8.75, 17.5, 35, and from 8.75 to 35, or within any range defined between any pair of the foregoing values.

An eighty-first embodiment includes methods according to either of the twentieth and eightieth embodiments wherein the controlled plant is at least one plant selected from the group consisting of: DIGSA, LEFCH, CYPES, ECHOR, CYPRO, and CYPIR, still other embodiments include controlling plants from the genera consisting of: *Digitaria, Leptochloa, Cyperus, Echinochloa, Cyperus.*

An eighty-second embodiment includes methods of controlling undesirable vegetation comprising the step of applying a herbicidally effective amount of at least one mixture according to the twenty-first embodiment wherein the amount of the mixture is applied at a rate, expressed in gai/ha or gae/ha of orthosulfamuron selected from the group of rates and ranges of rates consisting of about: 7.5, 15, 30, 60 from 7.5 to 15, from 7.5 to 30, from 7.5 to 60, or within any range defined between any pair of the foregoing values.

An eighty-third embodiment includes methods according to either of the twenty-first and eighty-second embodiments wherein the controlled plant is at least one plant selected from the group consisting of: LEFCH, BRAPP, CYPIR, CYPES, ECHOR, SCPMA, still other embodiments include controlling plants from the genera consisting of: *Leptochloa, Cyperus, Schoenoplectus, Bolboschoenus, Echinochloa, Brachiaria.*

An eighty-fourth embodiment includes methods of controlling undesirable vegetation comprising the step of applying a herbicidally effective amount of at least one mixture according to the twenty-second embodiment wherein the amount of the mixture is applied at a rate, expressed in gai/ha or gae/ha of primisulfuron-methyl selected from the group of rates and ranges of rates consisting of about: 15, 30 and from 15 to 30, or within any range defined between any pair of the foregoing values.

An eighty-fifth embodiment includes methods according to either of the twenty-second and eighty-fourth embodiments wherein the controlled plant is at least one plant selected from the group consisting of: LEFCH, still other embodiments include controlling plants from the genera consisting of: *Leptochloa.*

An eighty-sixth embodiment includes methods of controlling undesirable vegetation comprising the step of applying a herbicidally effective amount of at least one mixture according to the twenty-third embodiment wherein the amount of the mixture is applied at a rate, expressed in gai/ha or gae/ha of propyrisulfuron sodium selected from the group of rates and ranges of rates consisting of about: 11.25, 22.5, 45 and from 11.25 to 45, or within any range defined between any pair of the foregoing values.

An eighty-seventh embodiment includes methods according to either of the twenty-third and eighty-sixth embodiments wherein the controlled plant is at least one plant selected from the group consisting of: BRAPP, SCPMA, FIMMI, still other embodiments include controlling plants from the genera consisting of: *Schoenoplectus, Bolboschoenus, Brachiaria, Fimbristylis.*

An eighty-eighth embodiment includes methods of controlling undesirable vegetation comprising the step of applying a herbicidally effective amount of at least one mixture according to the twenty-fourth embodiment wherein the amount of the mixture is applied at a rate, expressed in gai/ha or gae/ha of prosulfuron selected from the group of rates and ranges of rates consisting of about: from 7 to 65, from 4.4 to 40, or within any range defined between any pair of the foregoing values.

An eighty-ninth embodiment includes methods according to either of the twenty-fourth and eighty-eighth used in herbicidally effective rates for controlling the growth of undesirable plants that have a negative impact on the growth of various crop plants.

A ninetieth embodiment includes methods of controlling undesirable vegetation comprising the step of applying a herbicidally effective amount of at least one mixture according to the twenty-fifth embodiment wherein the amount of the mixture is applied at a rate, expressed in gai/ha or gae/ha of pyrimisulfan selected from the group of rates and ranges of rates consisting of about: from 10 to 200, from 15 to 300, or within any range defined between any pair of the foregoing values.

A ninety-first embodiment includes methods according to either of the twenty-fifth and ninetieth used in herbicidally effective rates for controlling the growth of undesirable plants that have a negative impact on the growth of various crop plants.

A ninety-second embodiment includes methods of controlling undesirable vegetation comprising the step of applying a herbicidally effective amount of at least one mixture according to the twenty-sixth embodiment wherein the amount of the mixture is applied at a rate, expressed in gai/ha or gae/ha of pyroxasulfone selected from the group of rates and ranges of rates consisting of about: from 100 to 1000, from 105 to 350, or within any range defined between any pair of the foregoing values.

A ninety-third embodiment includes methods according to either of the twenty-sixth and ninety-second used in herbicidally effective rates for controlling the growth of undesirable plants that have a negative impact on the growth of various crop plants.

A ninety-fourth embodiment includes methods of controlling undesirable vegetation comprising the step of applying a herbicidally effective amount of at least one mixture according to the twenty-seventh embodiment wherein the amount of the mixture is applied at a rate, expressed in gai/ha or gae/ha of rimsulfuron selected from the group of rates and ranges of rates consisting of about: 2.19, 4.38, 8.75, and from 2.19 to 8.75, or within any range defined between any pair of the foregoing values.

A ninety-fifth embodiment includes methods according to either of the twenty-seventh and ninety-fourth embodiments wherein the controlled plant is at least one plant selected from the group consisting of: IPOHE, CYPES, LEFCH, CYPRO, and DIGSA, still other embodiments include controlling plants from the genera consisting of: *Ipomoea, Cyperus, Leptochloa, Digitaria*.

A ninety-sixth embodiment includes methods of controlling undesirable vegetation comprising the step of applying a herbicidally effective amount of at least one mixture according to the twenty-eighth embodiment wherein the amount of the mixture is applied at a rate, expressed in gai/ha or gae/ha of sulfometuron-methyl selected from the group of rates and ranges of rates consisting of about: 35, or within any range defined between any pair of the foregoing values.

A ninety-seventh embodiment includes methods according to either of the twenty-eighth and ninety-sixth embodiments wherein the controlled plant is at least one plant selected from the group consisting of: DIGSA, still other embodiments include controlling plants from the genera consisting of: *Digitaria*.

A ninety-eighth embodiment includes methods of controlling undesirable vegetation comprising the step of applying a herbicidally effective amount of at least one mixture according to the twenty-ninth embodiment wherein the amount of the mixture is applied at a rate, expressed in gai/ha or gae/ha of sulfosulfuron selected from the group of rates and ranges of rates consisting of about: 8.75 or within any range defined between any pair of the foregoing values.

A ninety-ninth embodiment includes methods according to either of the twenty-ninth and ninety-eighth embodiments wherein the controlled plant is at least one plant selected from the group consisting of: LAMPU, VERPE, MATCH, CIRAR, still other embodiments include controlling plants from the genera consisting of: *Lamium, Veronica, Chamomilla, Cirsium*.

A one-hundredth embodiment includes methods of controlling undesirable vegetation comprising the step of applying a herbicidally effective amount of at least one mixture according to the thirtieth embodiment wherein the amount of the mixture is applied at a rate, expressed in gai/ha or gae/ha of thifensulfuron-methyl selected from the group of rates and ranges of rates consisting of about: 3.75, or within any range defined between any pair of the foregoing values.

A one-hundred-first embodiment includes methods according to either of the thirtieth and one-hundredth embodiments wherein the controlled plant is at least one plant selected from the group consisting of: CIRAR, still other embodiments include controlling plants from the genera consisting of: *Cirsium*.

A one-hundred-second embodiment includes methods of controlling undesirable vegetation comprising the step of applying a herbicidally effective amount of at least one mixture according to the thirty-first embodiment wherein the amount of the mixture is applied at a rate, expressed in gai/ha or gae/ha of triafamone selected from the group of rates and ranges of rates consisting of about: from 7 to 200, from 5 to 50, or within any range defined between any pair of the foregoing values.

A one-hundred-third embodiment includes methods according to either of the thirty-first and one-hundred-second used in herbicidally effective rates for controlling the growth of undesirable plants that have a negative impact on the growth of various crop plants.

A one-hundred-fourth embodiment includes methods of controlling undesirable vegetation comprising the step of applying a herbicidally effective amount of at least one mixture according to the thirty-second embodiment wherein the amount of the mixture is applied at a rate, expressed in gai/ha or gae/ha of triasulfuron selected from the group of rates and ranges of rates consisting of about: from 2.2 to 30, from 5 to 50, or within any range defined between any pair of the foregoing values.

A one-hundred-fifth embodiment includes methods according to either of the thirty-second and one-hundred-fourth used in herbicidally effective rates for controlling the growth of undesirable plants that have a negative impact on the growth of various crop plants.

A one-hundred-sixth embodiment includes methods of controlling undesirable vegetation comprising the step of applying a herbicidally effective amount of at least one mixture according to the thirty-third embodiment wherein the amount of the mixture is applied at a rate, expressed in gai/ha or gae/ha of tribenuron-methyl selected from the group of rates and ranges of rates consisting of about: 2.2, or within any range defined between any pair of the foregoing values.

A one-hundred-eighth embodiment includes methods according to either of the thirty-third and one-hundred-sixth embodiments wherein the controlled plant is at least one plant selected from the group consisting of: MATCH, CIRAR, still other embodiments include controlling plants from the genera consisting of: *Chamomilla, Cirsium*.

A one-hundred-ninth embodiment includes methods of controlling undesirable vegetation comprising the step of applying a herbicidally effective amount of at least one mixture according to the thirty-fourth embodiment wherein the amount of the mixture is applied at a rate, expressed in gai/ha or gae/ha of trifloxysulfuron-sodium selected from the group of rates and ranges of rates consisting of about: 24, or within any range defined between any pair of the foregoing values.

A one-hundred-tenth embodiment includes methods according to either of the thirty-fourth and one-hundred ninth embodiments wherein the controlled plant is at least one plant selected from the group consisting of: DIGSA, still other embodiments include controlling plants from the genera consisting of: *Digitaria*.

Provided herein are herbicidal compositions comprising and methods for controlling undesirable vegetation utilizing a herbicidally effective amount of (a) a compound of the formula (I)

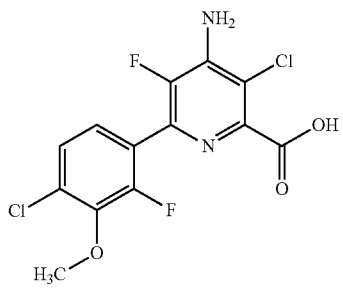

(I)

or an agriculturally acceptable salt or ester thereof, and (b) a sulfonylurea selected from the group consisting of amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl and trifloxysulfuron-sodium, or an agriculturally acceptable salt or ester thereof. In certain embodiments, the compositions further comprise an agriculturally acceptable adjuvant or carrier.

DETAILED DESCRIPTION

Definitions

As used herein, the compound of formula (I) has the following structure:

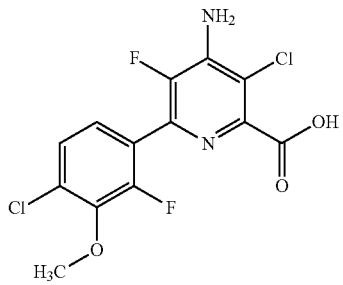

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, amidosulfuron is N-[[[[(4,6-dimethoxy-2-pyrimidinyl)amino]carbonyl]amino]sulfonyl]-N-methyl-methanesulfonamide and possesses the following structure:

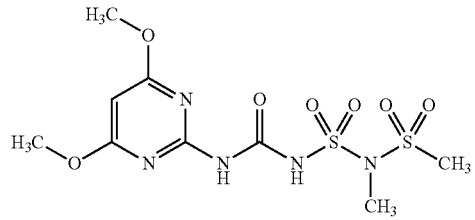

Its herbicidal activity is exemplified in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Amidosulfuron provides, e.g., post-emergence control of a wide range of broadleaf weeds, e.g., cleavers, in winter wheat, durum wheat, barley, rye, triticale and oats.

As used herein, azimsulfuron is N-[[(4,6-dimethoxy-2-pyrimidinyl)amino]carbonyl]-1-methyl-4-(2-methyl-2H-tetrazol-5-yl)-1H-pyrazole-5-sulfonamide and possesses the following structure:

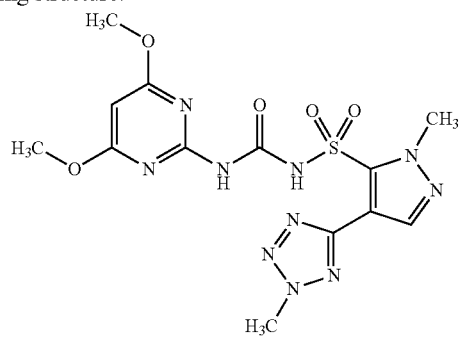

Its herbicidal activity is exemplified in *The Pesticide Manual*, Fifteenth Edition, 2009. Azimsulfuron provides, e.g., post-emergence control of annual and perennial broadleaf and sedge weeds in rice.

As used herein, bensulfuron-methyl is methyl 2-[[[[[(4,6-dimethoxy-2-pyrimidinyl)amino]carbonyl]amino]sulfonyl]methyl]benzoate and possesses the following structure:

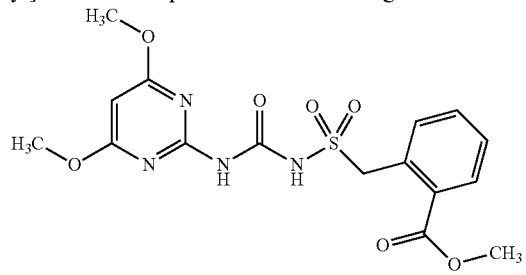

Its herbicidal activity is exemplified in *The Pesticide Manual*, Fifteenth Edition, 2009. Bensulfuron-methyl provides, e.g., pre- and post-emergence control of annual and perennial broadleaf weeds and sedges in rice. In certain embodiments, the free carboxylic acid, with respect to the methyl ester moiety, i.e., α-(4,6-dimethoxypyrimidin-2-yl-carbamoylsulfamoyl)-o-toluic acid, or its salt, is utilized. In certain embodiments, a different ester, e.g., an alkyl or aralkyl ester is utilized.

As used herein, chlorsulfuron is 2-chloro-N-[[(4-methoxy-6-methyl-1,3,5-triazin-2-yl)amino]carbonyl]benzene-sulfonamide and possesses the following structure:

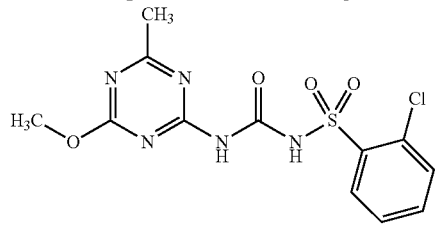 [SMILES: COc1nc(C)nc(NC(=O)NS(=O)(=O)c2ccccc2Cl)n1]

Its herbicidal activity is exemplified in *The Pesticide Manual*, Fifteenth Edition, 2009. Chlorsulfuron provides control of, e.g., broadleaf weeds and annual grasses in wheat, barley, oats, rye, triticale, flax and on non-crop land.

As used herein, cyclosulfamuron is N-[[[2-(cyclopropyl-carbonyl)phenyl]amino]sulfonyl]-N'-(4,6-dimethoxy-2-pyrimidinyl)urea and possess the following structure:

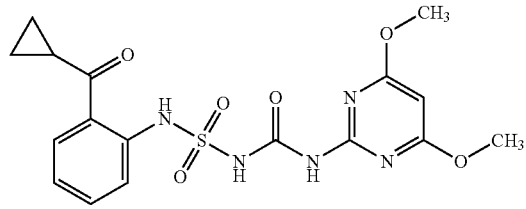 [SMILES: COc1cc(OC)nc(NC(=O)NS(=O)(=O)Nc2ccccc2C(=O)C2CC2)n1]

Its herbicidal activity is exemplified in Senseman, S., ed. Herbicide Handbook. 9th ed. Lawrence: Weed Science Society of America, 2007 ("Herbicide Handbook, Ninth Edition, 2007"). Cyclosulfamuron provides control of, e.g., dicotyledonous and sedge weeds, e.g. *Cyperus serotinus, Eleocharis kuroguwai* and *Sagittaria pygmaea*, in rice and *Galium aparine, Matricaria* spp., *Veronica* spp., *Sinapis arvensis* and *Brassica napus* in wheat and barley.

As used herein, ethametsulfuron-methyl is methyl 2-[[[[[4-ethoxy-6-(methylamino)-1,3,5-triazin-2-yl]amino]carbonyl]amino]sulfonyl]benzoate and possess the following structure:

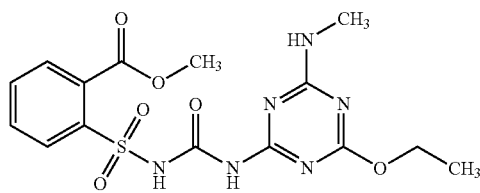 [SMILES: CCOc1nc(NC)nc(NC(=O)NS(=O)(=O)c2ccccc2C(=O)OC)n1]

Its herbicidal activity is exemplified in the *Herbicide Handbook*, Ninth Edition, 2007. Ethametsulfuron-methyl provides, e.g., post-emergence control of wild mustard, hempnettle and other broadleaf weeds in oilseed rape. In some embodiments, the corresponding carboxylic acid of salt thereof, or a different ester, e.g., alkyl or aralkyl ester, with respect the methyl ester moiety, is utilized.

As used herein, ethoxysulfuron is 2-ethoxyphenyl[[(4,6-dimethoxy-2-pyrimidinyl)amino]carbonyl]sulfamate and possesses the following structure:

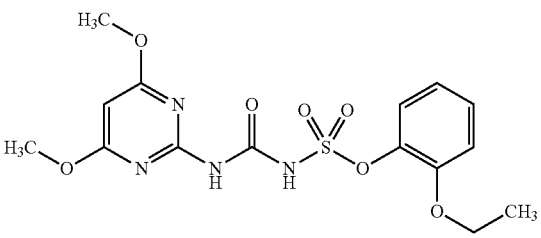 [SMILES: CCOc1ccccc1OS(=O)(=O)NC(=O)Nc1nc(OC)cc(OC)n1]

Its herbicidal activity is exemplified in *The Pesticide Manual*, Fifteenth Edition, 2009. Ethoxysulfuron provides, e.g., control of broadleaf and sedge weeds in cereals, rice and sugar cane.

As used herein, flazasulfuron is N-[[(4,6-dimethoxy-2-pyrimidinyl)amino]carbonyl]-3-(trifluoromethyl)-2-pyridinesulfonamide and possess the following structure:

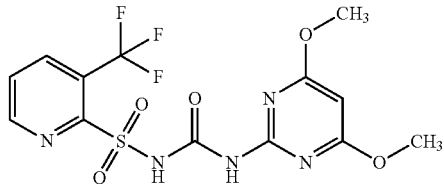 [SMILES: COc1cc(OC)nc(NC(=O)NS(=O)(=O)c2ncccc2C(F)(F)F)n1]

Its herbicidal activity is exemplified in the *Herbicide Handbook*, Ninth Edition, 2007. Flazasulfuron provides, e.g., pre-emergence and postemergence control of grass, broadleaf and sedge weeds in warm-season turf, vines, sugar cane, citrus, olives and on railways and other non-crop land.

As used herein, flucetosulfuron is 1-[3-[[[[(4,6-dimethoxy-2-pyrimidinyl)amino]carbonyl]amino]sulfonyl]-2-pyridinyl]-2-fluoropropyl 2-methoxyacetate and possesses the following structure:

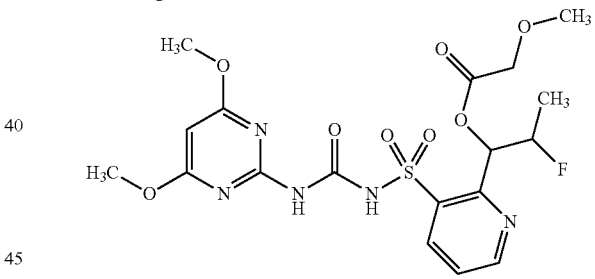

Its herbicidal activity is exemplified in *The Pesticide Manual*, Fifteenth Edition, 2009. Flucetosulfuron provides control of, e.g., broadleaf weeds, some grass weeds, and sedges in rice and cereals.

As used herein, flupyrsulfuron-methyl sodium is methyl 2-[[[[(4,6-dimethoxy-2-pyrimidinyl)amino]carbonyl]amino]sulfonyl]-6-(trifluoromethyl)-3-pyridinecarboxylate monosodium salt and possesses the following structure:

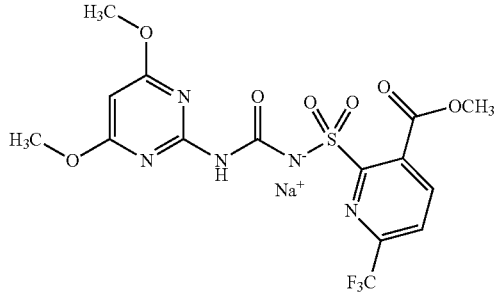 [SMILES: COC(=O)c1ccc(C(F)(F)F)nc1S(=O)(=O)[N-]C(=O)Nc1nc(OC)cc(OC)n1 ; [Na+]]

Its herbicidal activity is exemplified in *The Pesticide Manual*, Fifteenth Edition, 2009. Flupyrsulfuron-methyl sodium is used, e.g., for post-emergent control of grass and broadleaf weeds in cereals. In certain embodiments, the carboxylic acid or a salt thereof, or a different ester, e.g., alkyl or aralkyl ester, with respect to the methyl ester moiety is utilized. In certain embodiments, a different salt or non-ionic form is utilized.

As used herein, foramsulfuron is 2-[[[[(4,6-dimethoxy-2-pyrimidinyl)amino]carbonyl]amino]sulfonyl]-4-(formylamino)-N,N-dimethylbenzamide and possess the following structure:

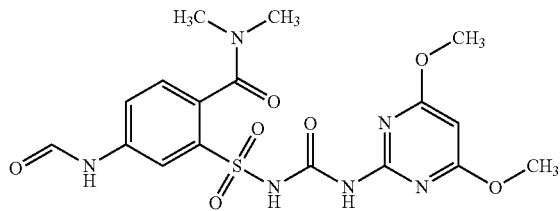 [SMILES: COc1cc(OC)nc(NC(=O)NS(=O)(=O)c2cc(NC=O)ccc2C(=O)N(C)C)n1]

Its herbicidal activity is exemplified in the *Herbicide Handbook*, Ninth Edition, 2007. Foramsulfuron provides, e.g., post-emergence control of grass and broadleaf weeds in maize.

As used herein, imazosulfuron is 2-chloro-N-[[(4,6-dimethoxy-2-pyrimidinyl)amino]carbonyl]imidazo[1,2-a]pyridine-3-sulfonamide and possesses the following structure:

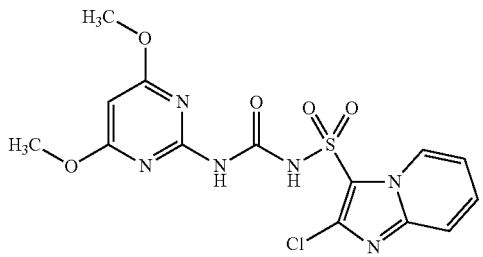 [SMILES: COc1cc(OC)nc(NC(=O)NS(=O)(=O)c2c(Cl)nc3ccccn23)n1]

Its herbicidal activity is exemplified in *The Pesticide Manual*, Fifteenth Edition, 2009. Imazosulfuron provides, e.g., control of annual and perennial broadleaf weeds and sedges in paddy rice and turf.

As used herein, iodosulfuron-methyl sodium is methyl 4-iodo-2-[[[[(4-methoxy-6-methyl-1,3,5-triazin-2-yl)amino]carbonyl]amino]sulfonyl]benzoate, sodium salt and possesses the following structure:

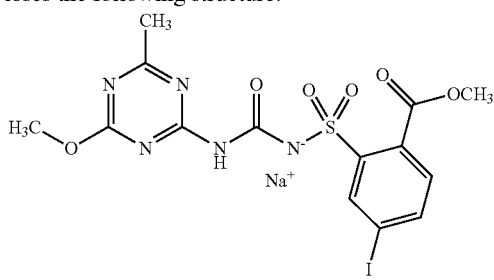

Its herbicidal activity is exemplified in *The Pesticide Manual*, Fifteenth Edition, 2009. Iodosulfuron-methyl sodium provides, e.g., post-emergence control of grass and broadleaf weeds in winter, spring and durum wheat, triticale, rye and spring barley. In certain embodiments, the carboxylic acid or a salt thereof, or a different ester, e.g., alkyl or aralkyl ester, with respect to the methyl ester moiety is utilized. In certain embodiments, a different salt or non-ionic form is utilized.

As used herein, iofensulfuron is 2-iodo-N-[[(4-methoxy-6-methyl-1,3,5-triazin-2-yl)amino]carbonyl]benzenesulfonamide and possesses the following structure:

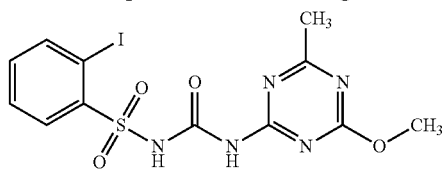

Its herbicidal activity is exemplified in *The Pesticide Manual*, Fifteenth Edition, 2009. Iofensulfuron provides control of, e.g., annual grass, broadleaf and sedge weeds in rice.

As used herein, mesosulfuron-methyl is methyl 2-[[[[(4,6-dimethoxy-2-pyrimidinyl)amino]carbonyl]amino]sulfonyl]-4-[[(methylsulfonyl)amino]methyl]benzoate and possesses the following structure:

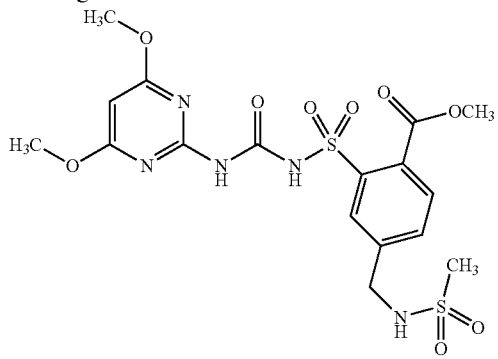

Its herbicidal activity is exemplified in *The Pesticide Manual*, Fifteenth Edition, 2009. Mesosulfuron-methyl provides, e.g., early to mid post-emergence control of grass and broadleaf weeds in winter, spring and durum wheat, triticale and rye. In certain embodiments, the carboxylic acid or a salt thereof, or a different ester, e.g., alkyl or aralkyl ester, with respect to the methyl ester moiety is utilized.

As used herein, metsulfuron-methyl is methyl 2-[[[[(4-methoxy-6-methyl-1,3,5-triazin-2-yl)amino]carbonyl]amino]sulfonyl]benzoate and possesses the following structure:

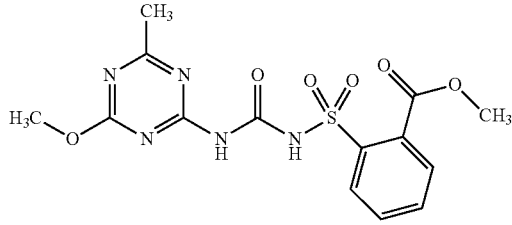

Its herbicidal activity is exemplified in *The Pesticide Manual*, Fifteenth Edition, 2009. Metsulfuron-methyl controls, e.g., grass and broadleaf weeds in wheat, barley, rice, oats and triticale. In certain embodiments, the carboxylic acid or a salt thereof, or a different ester, e.g., alkyl or aralkyl ester, with respect to the methyl ester moiety is utilized.

As used herein, nicosulfuron is 2-[[[[(4,6-dimethoxy-2-pyrimidinyl)amino]carbonyl]amino]sulfonyl]-N,N-dimethyl-3-pyridinecarboxamide and possesses the following structure:

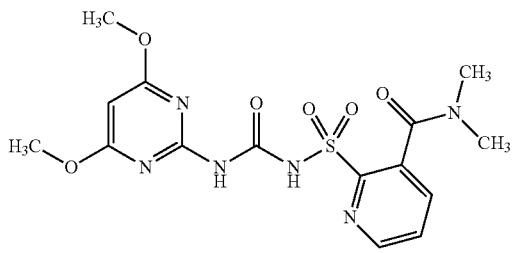

Its herbicidal activity is exemplified in *The Pesticide Manual*, Fifteenth Edition, 2009. Nicosulfuron provides, e.g., selective post-emergence control in maize of annual grass weeds, including *Setaria, Echinochloa, Digitaria, Panicum, Lolium* and *Avena* spp., broadleaf weeds, including *Amaranthus* spp. and *Cruciferae*, and perennials such as *Sorghum halepense* and *Agropyron repens*.

As used herein, orthosulfamuron is 2-[[[[[(4,6-dimethoxy-2-pyrimidinyl)amino]carbonyl]amino]sulfonyl]amino]-N,N-dimethylbenzamide and possesses the following structure:

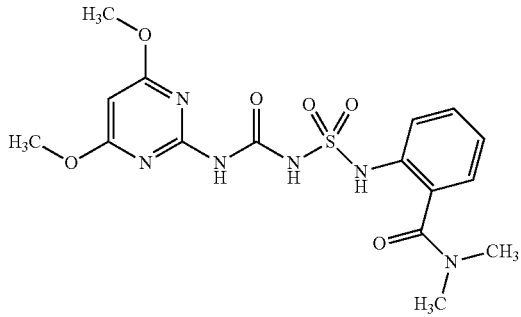

Its herbicidal activity is exemplified in *The Pesticide Manual*, Fifteenth Edition, 2009. Orthosulfamuron provides, e.g., early post-emergence control of annual and perennial broadleaf weeds and sedges in rice, cereals, pastures and sugar cane.

As used herein, primisulfuron-methyl is methyl 2-[[[[[4,6-bis(difluoromethoxy)-2-pyrimidinyl]amino]carbonyl]amino]sulfonyl]benzoate and possesses the following structure:

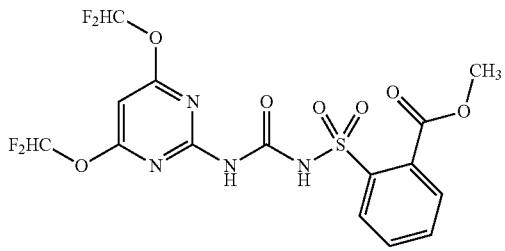 [SMILES: COC(=O)c1ccccc1S(=O)(=O)NC(=O)Nc1nc(OC(F)F)cc(OC(F)F)n1]

Its herbicidal activity is exemplified in *The Pesticide Manual*, Fifteenth Edition, 2009. Primisulfuron-methyl provides, e.g., post-emergence control of problem grass weeds, including *Sorghum bicolor, Sorghum almum, Sorghum halepense* and *Agropyron repens*, and many broadleaf weeds, in maize. In certain embodiments, the carboxylic acid or a salt thereof, or a different ester, e.g., alkyl or aralkyl ester, with respect to the methyl ester moiety is utilized.

As used herein, propyrisulfuron is 2-chloro-N-[[(4,6-dimethoxy-2-pyrimidinyl)amino]carbonyl]-6-propylimidazo[1,2-b]pyridazine-3-sulfonamide and possesses the following structure:

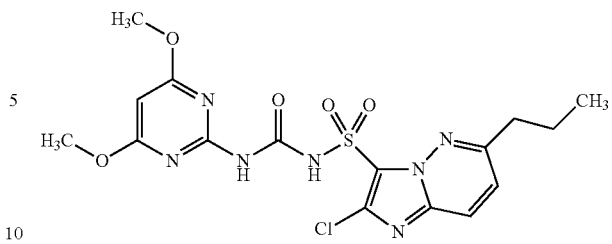

Its herbicidal activity is exemplified in: Development of a novel paddy rice herbicide propyrisulfuron (ZETA-ONE), Sumitomo Kagaku (Osaka, Japan) (2011), (2), 14-25. Publisher: (Sumitomo Kagaku Kogyo K.K.). Propyrisulfuron is used, e.g., as a rice herbicide to control annual and perennial paddy weeds, including *Echinochloa* spp., sedges and broadleaf weeds.

As used herein, prosulfuron is N-[[(4-methoxy-6-methyl-1,3,5-triazin-2-yl)amino]carbonyl]-2-(3,3,3-trifluoropropyl)benzene sulfonamide and possess the following structure:

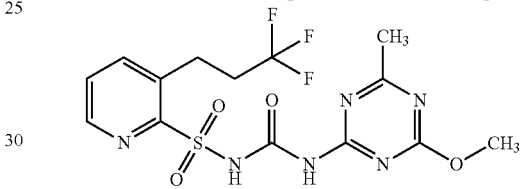

Its herbicidal activity is exemplified in the *Herbicide Handbook*, Ninth Edition, 2007. Prosulfuron provides, e.g., post-emergence control of annual broadleaf weeds in maize, sorghum, cereals, pasture and turf.

As used herein, pyrimisulfan is N-[2-[(4,6-dimethoxy-2-pyrimidinyl)hydroxymethyl]-6-(methoxymethyl)phenyl]-1,1-difluoromethanesulfonamide and possesses the following structure:

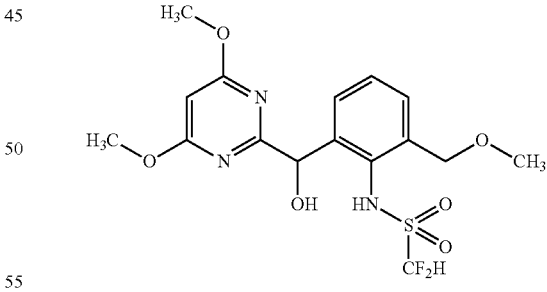

Its herbicidal activity is exemplified in the Journal of Pesticide Science (Tokyo, Japan) (2012), 37(1), 62-68. Pyrimisulfan can be used, e.g., as a herbicide for the control of rice weeds in rice fields.

As used herein, pyroxasulfone is 3-[[[5-(difluoromethoxy)-1-methyl-3-(trifluoromethyl)-1H-pyrazol-4-yl]methyl]sulfonyl]-4,5-dihydro-5,5-dimethylisoxazole and possesses the following structure:

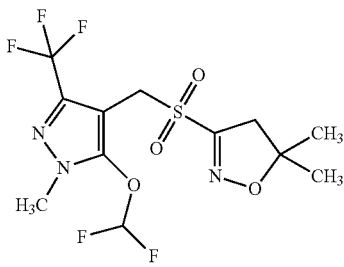 [SMILES: Cn1nc(C(F)(F)F)c(CS(=O)(=O)C2=NOC(C)(C)C2)c1OC(F)F]

Its herbicidal activity is exemplified in *The Pesticide Manual*, Fifteenth Edition, 2009. Pyroxasulfone provides, e.g., pre-emergence control of annual grasses and some broadleaf weeds in maize, soya beans, wheat and other crops.

As used herein, rimsulfuron is N-[[(4,6-dimethoxy-2-pyrimidinyl)amino]carbonyl]-3-(ethylsulfonyl)-2-pyridinesulfonamide and possesses the following structure:

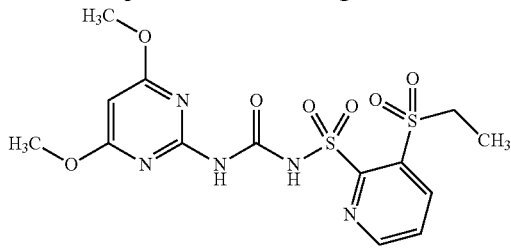

Its herbicidal activity is exemplified in *The Pesticide Manual*, Fifteenth Edition, 2009. Rimsulfuron provides, e.g., post-emergence control of most annual and perennial grasses and several broadleaf weeds in maize.

As used herein, sulfometuron-methyl is methyl 2-[[[[(4,6-dimethyl-2-pyrimidinyl)amino]carbonyl]amino]sulfonyl]benzoate and possesses the following structure:

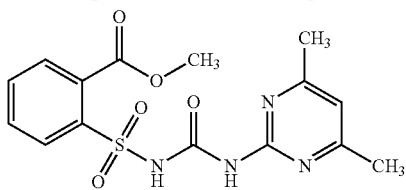 [SMILES: COC(=O)c1ccccc1S(=O)(=O)NC(=O)Nc1nc(C)cc(C)n1]

Its herbicidal activity is exemplified in *The Pesticide Manual*, Fifteenth Edition, 2009. Sulfometuron-methyl provides, e.g., control of annual and perennial grasses and broadleaf weeds in non-crop land. It is also used, e.g., for selective weed control in Bermuda grass and other turf grasses; and in forestry to control woody tree species in pine trees. In certain embodiments, the carboxylic acid or a salt thereof, or a different ester, e.g., alkyl or aralkyl ester, with respect to the methyl ester moiety is utilized.

As used herein, sulfosulfuron is N-[[(4,6-dimethoxy-2-pyrimidinyl)amino]carbonyl]-2-(ethylsulfonyl)imidazo[1,2-a]pyridine-3-sulfonamide and possesses the following structure:

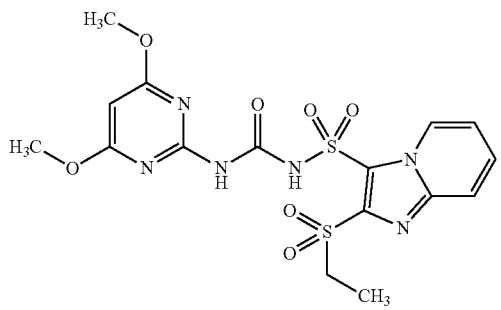 [SMILES: CCS(=O)(=O)c1nc2ccccn2c1S(=O)(=O)NC(=O)Nc1nc(OC)cc(OC)n1]

Its herbicidal activity is exemplified in *The Pesticide Manual*, Fifteenth Edition, 2009. Sulfosulfuron can be used, e.g., in the control of annual broadleaf weeds and grass weeds in cereals.

As used herein, thifensulfuron-methyl is methyl 3-[[[[(4-methoxy-6-methyl-1,3,5-triazin-2-yl)amino]carbonyl]amino]sulfonyl]-2-thiophenecarboxylate and possesses the following structure:

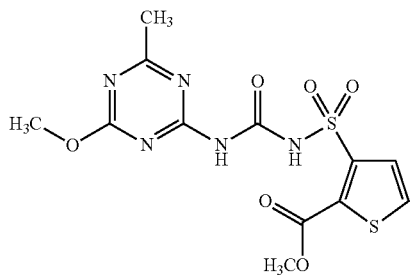 [SMILES: COC(=O)c1sccc1S(=O)(=O)NC(=O)Nc1nc(C)nc(OC)n1]

Its herbicidal activity is exemplified in *The Pesticide Manual*, Fifteenth Edition, 2009. Thifensulfuron-methyl is used, e.g., in the control of annual weeds in cereals, maize and pasture. In certain embodiments, the carboxylic acid or a salt thereof, or a different ester, e.g., alkyl or aralkyl ester, with respect to the methyl ester moiety is utilized.

As used herein, triafamone is N-[2-[(4,6-dimethoxy-1,3,5-triazin-2-yl)carbonyl]-6-fluorophenyl]-1,1-difluoro-N-methylmethanesulfonamide and possesses the following structure:

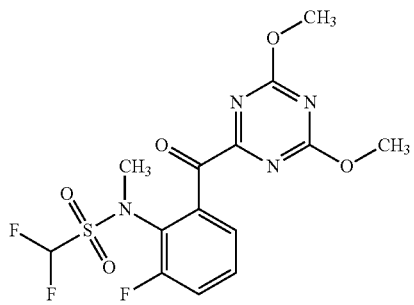 [SMILES: COc1nc(OC)nc(C(=O)c2cccc(F)c2N(C)S(=O)(=O)C(F)F)n1]

Its herbicidal activity is exemplified in the published article Shijie Nongyao (2011), 33(3), 22-24. Triafamone is used, e.g., in the pre- and post-emergence control of grass, broadleaf and sedge weeds in rice.

As used herein, triasulfuron is 2-(2-chloroethoxy)-N-[[(4-methoxy-6-methyl-1,3,5-triazin-2-yl)amino]carbonyl]benzenesulfonamide and possess the following structure:

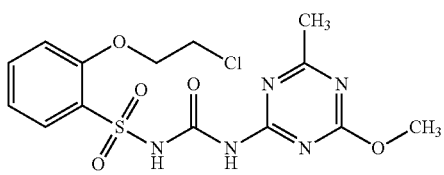 [SMILES: COc1nc(C)nc(NC(=O)NS(=O)(=O)c2ccccc2OCCCl)n1]

Its herbicidal activity is exemplified in the *Herbicide Handbook*, Ninth Edition, 2007. Triasulfuron is used, e.g., in the pre- and post-emergence control of broadleaf weeds in wheat, barley and triticale.

As used herein, tribenuron-methyl is methyl 2-[[[[(4-methoxy-6-methyl-1,3,5-triazin-2-yl)methylamino]carbonyl]amino]sulfonyl]benzoate and possesses the following structure:

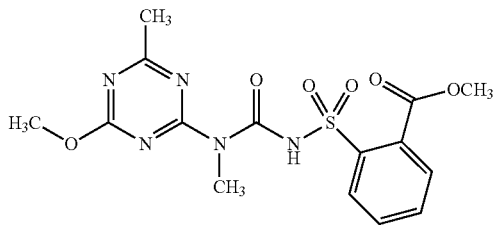 [SMILES: COC(=O)c1ccccc1S(=O)(=O)NC(=O)N(C)c1nc(C)nc(OC)n1]

Its herbicidal activity is exemplified in *The Pesticide Manual*, Fifteenth Edition, 2009. Tribenuron-methyl is used, e.g., in post-emergence control of broadleaf weeds in cereal crops, including wheat, barley, oats, rye and triticale.

As used herein, trifloxysulfuron-sodium is N-[[(4,6-dimethoxy-2-pyrimidinyl)amino]carbonyl]-3-(2,2,2-trifluoroethoxy)-2-pyridinesulfonamide, sodium salt and possesses the following structure:

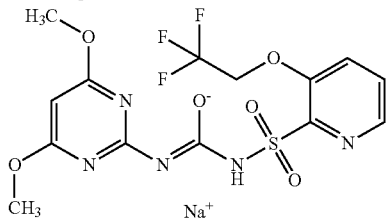 [SMILES: COc1cc(OC)nc(/N=C(\[O-])NS(=O)(=O)c2ncccc2OCC(F)(F)F)n1 ; [Na+]]

Its herbicidal activity is exemplified in *The Pesticide Manual*, Fifteenth Edition, 2009. Trifloxysulfuron-sodium is used for post-emergence grass, sedge and broadleaf weed control in cotton and sugar cane. It is also used in turf and weed control in plantations. In certain embodiments, a different salt or non-ionic form is utilized.

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as preemergence, postemergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising an herbicidally effective amount of (a) a compound of the formula (I)

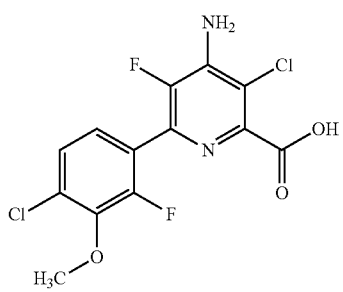

(I)

or an agriculturally acceptable salt or ester thereof, and (b) a sulfonylurea selected from the group consisting of amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl and trifloxysulfuron-sodium or an agriculturally acceptable salt or ester thereof.

Provided herein are also methods of controlling undesirable vegetation comprising contacting the vegetation or the locus thereof, i.e., area adjacent to the vegetation, with or applying to the soil or water to prevent the emergence or growth of vegetation a herbicidally effective amount of the compound of formula (I) or agriculturally acceptable salt or ester thereof and (b) a sulfonylurea selected from the group consisting of: amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, prosulfuron, pyrimisulfan, pyroxasulfone, rimsulfuron, sulfometuron-methyl, sulfosulfuron, thifensulfuron-methyl, triafamone, triasulfuron, tribenuron-methyl and trifloxysulfuron-sodium or an agriculturally acceptable salt or ester thereof.

In certain embodiments, the methods employ the compositions described herein.

Furthermore, in some embodiments, the combination of compound (I) or agriculturally acceptable salt or ester thereof and sulfonylurea, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. 9$^{th}$ ed. Lawrence: Weed Science Society of America, 2007 In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and sulfonylurea are formulated in one composition, tank mixed, applied simultaneously, or applied sequentially.

Herbicidal activity is exhibited by the compounds when they are applied directly to the plant or to the locus of the plant, i.e. area adjacent to the plant, at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in direct-seeded, water-seeded, and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, ornamental species, aquatics, plantation crops, vegetables, industrial vegetation management (IVM) and rights-of-way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L.

(wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (kylling a, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including, but not limited to *Brachiaria* or *Urochloa*, *Bolboschoenus*, *Cassia*, *Chamomilla*, *Cirsium*, *Cyperus*, *Digitaria*, *Echinochloa*, *Fimbristylis*, *Galium*, *Ipomoea*, *Ischaemum*, *Lamium*, *Leptochloa*, *Portulaca*, *Schoenoplectus*, *Sida*, *Veronica* and *Viola*.

In certain embodiments, the combination of compound (I) or agriculturally acceptable ester or salt thereof and sulfonylurea or agriculturally acceptable salt or ester thereof is used to control *Brachiaria platyphylla* (Griseb.) Nash or *Urochloa platyphylla* (Nash) R. D. Webster (broadleaf signalgrass, BRAPP), *Cassia obtusifolia* L. (sicklepod, CASOB), *Chamomilla chamomilla* (L.) Rydb. (scented mayweed, MATCH), *Cirsium arvense* (L.) Scop. (Canada thistle, CIRAR), *Cyperus difformis* L. (smallflower umbrella sedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Digitaria sanguinalis* (L.) Scop. (large crabgrass, DIGSA), *Echinochloa crus-galli* (L.) Beauv. (barnyardgrass, ECHCG), *Echinochloa colona* (L.) Link (junglerice, ECHCO), *Echinochloa oryzoides* (Ard.) Fritsch (early watergrass, ECHOR), *Fimbristylis miliacea* (L.) Vahl (globe fringerush, FIMMI), *Galium aparine* (L.) (cleavers, GALAP), *Ipomoea hederacea* Jacq. (ivyleaf morningglory, IPOHE), *Ischaemum rugosum* Salisb. (saramollagrass, ISCRU), *Lamium purpureum* (L.) (purple deadnettle, LAMPU), *Leptochloa chinensis* (L.) Nees (Chinese sprangletop, LEFCH), *Portulaca oleracea* L. (portulaca, POROL), *Schoenoplectus juncoides* (Roxb.) Palla (Japanese bulrush, SCPJU), *Bolboschoenus maritimus* (L.) Palla or *Schoenoplectus maritimus* (L.) Lye (sea clubrush, SCPMA), *Sida spinosa* L. (sida, prickly, SIDSP), *Veronica persica* Poir. (bird's-eye speedwell, VERPE) and *Viola tricolor* (L.) (wild pansy, VIOTR).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors, (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with amidosulfuron or salt thereof. With respect to the compositions, in some embodiments of the compositions described herein, the weight ratio of the compound of formula (I) or salt or ester thereof to amidosulfuron or salt thereof is within the range of from about 1:20 to about 34:1. In certain embodiments, the weight ratio of the compound of formula (I) or salt or ester thereof to amidosulfuron or salt thereof is within the range of from about 1:5 to about 8:1. In certain embodiments, the weight ratio of the compound of formula (I) or salt or ester thereof to amidosulfuron or salt thereof is within the range of from about 0.25:1 to about 4:1. In certain embodiments, the weight ratio of the compound of formula (I) or salt or ester thereof to amidosulfuron or salt thereof is within the range of from about 0.50:1 to about 2:1. In certain embodiments, the weight ratio of the compound of formula (I) or salt or ester thereof to amidosulfuron or salt thereof is about 1:1.1. In certain embodiments, the compositions provided herein comprise the benzyl ester of the compound of formula (I) and amidosulfuron. In one embodiment, the composition comprises the benzyl ester of the compound of formula (I) and amidosulfuron, wherein the weight ratio of the benzyl ester of the compound of formula (I) to amidosulfuron is about 1:1.1. With respect to the methods, in certain embodiments, the methods comprise contacting the undesirable vegetation or locus thereof or applying to the soil or water to prevent the emergence or growth of vegetation a composition described herein. In certain embodiments, the composition is applied at an application rate of from about 10 grams active ingredient per hectare (gai/ha) to about 340 gai/ha based on the total amount of active ingredients in the composition. In certain embodiments, the composition is applied at an application rate of from about 12 grams active ingredient per hectare (gai/ha) to about 110 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and amidosulfuron or salt thereof, e.g., sequentially or simultaneously. In some embodiments, the amidosulfuron or salt thereof is applied at a rate from about 8 gai/ha to about 40 gai/ha and the compound of formula (I) of salt or ester thereof is applied at a rate from about 2 g acid equivalent per hectare (gae/ha) to about 300 gae/ha. In some embodiments, the amidosulfuron or salt thereof is applied at a rate from about 4 gai/ha to about 24 gai/ha and the compound of formula (I) of salt or ester thereof is applied at a rate from about 3.5 g acid equivalent per hectare (gae/ha) to about 20 gae/ha. In some embodiments, the amidosulfuron or salt thereof is applied at a rate from about 8 gai/ha to about 12 gai/ha and the compound of formula (I) of salt or ester thereof is applied at a rate from about 7 g acid equivalent per hectare (gae/ha) to about 10 gae/ha. In some embodiments, the amidosulfuron or salt thereof is applied at a rate of about 10 gai/ha and the compound of formula (I) of salt or ester thereof is applied at a rate of about 8.75 g acid equivalent per hectare (gae/ha). In certain embodiments, the methods utilize the benzyl ester of the compound of formula (I) and amidosulfuron. In one embodiment, the methods utilize the benzyl ester of the compound of formula (I) and amidosulfuron, wherein the benzyl ester of the compound of formula (I) is applied at a rate of about 8.75 gai/ha, and the amidosulfuron is applied at a rate of about 10 gai/ha. In certain embodiments, the methods and compositions utilizing the compound of formula (I) or salt or ester thereof in combination with amidosulfuron or salt thereof are used to control GALAP, LAMPU, or VERPE.

In certain embodiments of the compositions and methods described herein, the compound of formula (I) or salt or ester thereof is used in combination with azimsulfuron or salt thereof. With respect to the composition, in some embodiments, the weight ratio of the compound of formula (I) or salt or ester thereof to azimsulfuron or salt thereof is within the range of from about 1:15 to about 120:1. In certain embodiments, the weight ratio of the compound of formula (I) or salt or ester thereof to azimsulfuron or salt thereof is within the range of from about 1:8 to about 28:1. In certain embodiments, the weight ratio of the compound of formula (I) or salt or ester thereof to azimsulfuron or salt thereof is within the range of from about 28:1 to about 1:3. In certain embodiments, the weight ratio of the compound of formula (I) or salt or ester thereof to azimsulfuron or salt thereof is within the range of from about 14:1 to about 1:1.1. In certain embodiments, the compositions provided herein comprise the compound of formula (I) or its benzyl or n-butyl ester and azimsulfuron. In one embodiment, the composition comprises the compound of formula (I) and azimsulfuron, wherein the weight ratio of the compound of formula (I) and azimsulfuron is about 14:1 to about 1.4:1. In one embodiment, the composition comprises the benzyl ester of the compound of formula (I) and azimsulfuron, wherein the weight ratio of the benzyl ester of the compound of formula (I) and azimsulfuron is about 7:1 to about 1:1.8. In one embodiment, the composition comprises the n-butyl ester of the compound of formula (I) and azimsulfuron, wherein the weight ratio of the n-butyl ester of the compound of formula (I) and azimsulfuron is about 2.8:1 to about 1.4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 330 gai/ha based on the total amount of active ingredients in the composition. In certain embodiments, the composition is applied at an application rate of from about 7 grams active ingredient per hectare (gai/ha) to about 100 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and azimsulfuron or salt thereof, e.g., sequentially or simultaneously. In some embodiments, the azimsulfuron or salt thereof is applied at a rate from about 2.5 gai/ha to about 30 gai/ha and the compound of formula (I) of salt or ester thereof is applied at a rate from about 2 gae/ha to about 300 gae/ha. In some embodiments, the azimsulfuron or salt thereof is applied at a rate from about 1.3 gai/ha to about 50 gai/ha and the compound of formula (I) of salt or ester thereof is applied at a rate from about 2 g acid equivalent per hectare (gae/ha) to about 140 gae/ha. In some embodiments, the azimsulfuron or salt thereof is applied at a rate from about 2.5 gai/ha to about 25 gai/ha and the compound of formula (I) of salt or ester thereof is applied at a rate from about 4.38 g acid equivalent per hectare (gae/ha) to about 70 gae/ha. In certain embodiments, the methods utilize the compound of formula (I) or its benzyl or n-butyl ester and azimsulfuron. In one embodiment, the methods utilize the compound of formula (I) and azimsulfuron, wherein the compound of formula (I) is applied at a rate of from about 8.75 g acid equivalent per hectare (gae/ha) to about 70 gae/ha, and the azimsulfuron is applied at a rate of from about 2.5 gai/ha to about 25 gai/ha. In one embodiment, the methods utilize the benzyl ester of the compound of formula (I) and azimsulfuron, wherein the benzyl ester of the compound of formula (I) is applied at a rate of from about 4.38 g acid equivalent per hectare (gae/ha) to about 70 gae/ha, and the azimsulfuron is applied at a rate of from about 2.5 gai/ha to about 25 gai/ha. In one embodiment, the methods utilize the n-butyl ester of the compound of formula (I) and azimsulfuron, wherein the n-butyl ester of the compound of formula (I) is applied at a rate of from about 17.5 g acid equivalent per hectare (gae/ha) to about 70 gae/ha, and the azimsulfuron is applied at a rate of about 25 gai/ha. In certain embodiments, the methods and compositions utilizing the compound of formula (I) or salt or ester thereof in combination with amidosulfuron or salt thereof are used to control BRAPP, LEFCH, ECHCG, ECHOR, or SCPMA.

In certain embodiments of the compositions and methods described herein, the compound of formula (I) or salt or ester thereof is used in combination with bensulfuron-methyl or salt, carboxylic acid, carboxylate salt, or ester thereof. With respect to the compositions, in some embodiments, the weight ratio of the compound of formula (I) or salt or ester thereof to bensulfuron- or salt, carboxylic acid, carboxylate salt, or ester thereof is within the range of from about 1:35 to about 17:1. In certain embodiments, the weight ratio of the compound of formula (I) or salt or ester thereof to bensulfuron-methyl or salt, carboxylic acid, carboxylate salt, or ester thereof is within the range of from about 1:16 to about 10:1. In certain embodiments, the weight ratio of the compound of formula (I) or salt or ester thereof to bensulfuron-methyl or salt, carboxylic acid, carboxylate salt, or ester thereof is within the range of from 1:0.2 to about 1:16. In certain embodiments, the weight ratio of the compound of formula (I) or salt or ester thereof to bensulfuron-methyl or salt, carboxylic acid, carboxylate salt, or ester thereof is within the range of from about 1:0.50 to about 1:8. In certain embodiments, the compositions provided herein comprise the compound of formula (I), its benzyl or n-butyl ester and bensulfuron-methyl. In one embodiment, the composition comprises the compound of formula (I) and bensulfuron-methyl, wherein the weight ratio of the compound of formula (I) to bensulfuron-methyl is from about 1:2 to about 1:8. In one embodiment, the composition comprises the benzyl ester of the compound of formula (I) and bensulfuron-methyl, wherein the weight ratio of the benzyl ester of the compound of formula (I) to bensulfuron-methyl is from about 1:0.5 to about 1:8. In one embodiment, the composition comprises the n-butyl ester of the compound of formula (I) and bensulfuron-methyl, wherein the weight ratio of the n-butyl ester of the compound of formula (I) to bensulfuron-methyl is about 1:0.5 to about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 370 gai/ha based on the total amount of active ingredients in the composition. In certain embodiments, the composition is applied at an application rate of from about 9 grams active ingredient per hectare (gai/ha) to about 120 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and bensulfuron-methyl or salt, carboxylic acid, carboxylate salt, or ester thereof, e.g., sequentially or simultaneously. In some embodiments, the bensulfuron-methyl or salt, carboxylic acid, carboxylate salt, or ester thereof is applied at a rate from about 4 gai/ha to about 70 gai/ha and the compound of formula (I) of salt or ester thereof is applied at a rate from about 2 gae/ha to about 300 gae/ha. In some embodiments, the bensulfuron-methyl or salt, carboxylic acid, carboxylate salt, or ester thereof is applied at a rate from about 4 gai/ha to about 140 gai/ha and the compound of formula (I) of salt or ester thereof is applied at a rate from about 2 g acid equivalent per hectare (gae/ha) to about 125 gae/ha. In some embodiments, the bensulfuron-methyl or salt, carboxylic acid, carboxylate salt, or ester thereof is applied at a rate from about 4 gai/ha to about 70 gai/ha and the compound of formula (I) of salt or ester thereof is applied at a rate from about 4 g acid equivalent per hectare (gae/ha) to about 70 gae/ha. In certain embodiments, the methods utilize the compound of formula (I) or its benzyl or n-butyl ester and bensulfuron methyl. In one embodiment, the methods utilize the compound of formula (I) and bensulfuron-methyl, wherein the compound of formula (I) is applied at a rate of from about 4.38 to about 42 gai/ha, and the bensulfuron-methyl is applied at a rate of from about 4.38 to about 70 gai/ha. In one embodiment, the methods utilize the benzyl ester of the compound of formula (I) and bensulfuron-methyl, wherein the benzyl ester of the compound of formula (I) is applied at a rate of from about 4.38 to about 17.5 gai/ha, and the bensulfuron-methyl is applied at a rate of from about 4.38 to about 35 gai/ha. In one embodiment, the methods utilize the n-butyl ester of the compound of formula (I) and bensulfuron-methyl, wherein the n-butyl ester of the compound of formula (I) is applied at a rate of from about 4.38 to about 8.75 gai/ha, and the bensulfuron-methyl is applied at a rate of from about 4.38 to about 17.5 gai/ha. In certain embodiments, the methods and compositions utilizing the compound of formula (I) or salt or ester thereof in combination with bensulfuron-methyl or salt, carboxylic acid, carboxylate salt, or ester thereof are used to control BRAPP, ECHCG, LEFCH, ECHOR, SCPMA, or ISCRU.

In certain embodiments of the compositions and methods described herein, the compound of formula (I) or salt or ester thereof is used in combination with chlorsulfuron or salt thereof. With respect to the compositions, in some embodiments, the weight ratio of the compound of formula (I) or salt or ester thereof to chlorsulfuron or salt thereof is within the range of from about 1:27 to about 136:1. In certain embodiments, the weight ratio of the compound of formula (I) or salt or ester thereof to chlorsulfuron or salt thereof is within the range of from about 1:32 to about 24:1. In certain embodiments, the weight ratio of the compound of formula (I) or salt or ester thereof to chlorsulfuron or salt thereof is within the range of from about 1.5:1 to about 10:1. In certain embodiments, the weight ratio of the compound of formula (I) or salt or ester thereof to chlorsulfuron or salt thereof is within the range of from about 3:1 to about 5:1. In certain embodiments, the weight ratio of the compound of formula (I) or salt or ester thereof to chlorsulfuron or salt thereof is about 4:1. In certain embodiments, the compositions provided herein comprise the benzyl ester of the compound of formula (I) and chlorsulfuron. In one embodiment, the composition comprises the benzyl ester of the compound of formula (I) and chlorsulfuron, wherein the weight ratio of the benzyl ester of the compound of formula (I) to chlorsulfuron is from about 3:1 to about 5:1. In one embodiment, the composition comprises the benzyl ester of the compound of formula (I) and chlorsulfuron, wherein the weight ratio of the benzyl ester of the compound of formula (I) to chlorsulfuron is about 4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 353 gai/ha based on the total amount of active ingredients in the composition. In certain embodiments, the composition is applied at an application rate of from about 5 grams active ingredient per hectare (gai/ha) to about 120 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and chlorsulfuron or salt thereof, e.g., sequentially or simultaneously. In some embodiments, the chlorsulfuron or salt thereof is applied at a rate from about 2 gai/ha to about 53 gai/ha and the compound of formula (I) of salt or ester thereof is applied at a rate from about 2 gae/ha to about 300 gae/ha. In some embodiments, the chlorsulfuron or salt thereof is applied at a rate from about 1 gai/ha to about 5 gai/ha and the compound of formula (I) of salt or ester thereof is applied at a rate from about 6 g acid equivalent per hectare (gae/ha) to about 10 gae/ha. In certain embodiments, the chlorsulfuron or salt thereof is applied at a rate from about 1.5 gai/ha to about 3.5 gai/ha and the compound of formula (I) of salt or ester thereof is applied at a rate from about 7 g acid equivalent per hectare (gae/ha) to about 9.5 gae/ha. In some embodiments, the chlorsulfuron or salt thereof is applied at a rate of about 2.2 gai/ha and the compound of formula (I) of salt or ester thereof is applied at a rate of about 8.75 g acid equivalent per hectare (gae/ha). In certain embodiments, the methods utilize the benzyl ester of the compound of formula (I) and chlorsulfuron. In one embodiment, the methods utilize the benzyl ester of the compound of formula (I) and chlorsulfuron, wherein the benzyl ester of the compound of formula (I) is applied at a rate of about 8.75 gai/ha, and the amidosulfuron is applied at a rate of about 2.2 gai/ha. In certain embodiments, the methods and compositions utilizing the compound of formula (I) or salt or ester thereof in combination with chlorsulfuron or salt thereof are used to control VIOTR or CIRAR.

In certain embodiments of the compositions and methods described herein, the compound of formula (I) or salt or ester thereof is used in combination with cyclosulfamuron or salt thereof. With regard to the compositions, in some embodiments, the weight ratio of the compound of formula (I) or salt or ester thereof to cyclosulfamuron or salt thereof is within the range of from about 1:30 to about 68:1. In certain embodiments, the weight ratio of the compound of formula (I) or salt or ester thereof to cyclosulfamuron or salt thereof is within the range of from about 1:20 to about 8:1. In certain embodiments, the weight ratio of the compound of formula (I) or salt or ester thereof to cyclosulfamuron or salt thereof is within the range of from about 1:1.5 to about 3:1. In certain embodiments, the compositions comprise the compound of formula (I) or its benzyl or n-butyl ester and cyclosulfamuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 360 gai/ha based on the total amount of active ingredients in the composition. In certain embodiments, the composition is applied at an application rate of from about 7 grams active ingredient per hectare (gai/ha) to about 80 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and cyclosulfamuron or salt thereof, e.g., sequentially or simultaneously. In some embodiments, the cyclosulfamuron or salt thereof is applied at a rate from about 4.4 gai/ha to about 60 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and cyclosulfamuron. In certain embodiments, the methods and compositions utilizing the compound of formula (I) or salt or ester thereof in combination with cyclosulfamuron or salt thereof are used to control CYPIR and SCPMA.

In certain embodiments of the compositions and methods described herein, the compound of formula (I) or salt or ester thereof is used in combination with ethametsulfuron-methyl or salt, carboxylic acid, carboxylate salt, or ester thereof. With regard to the compositions, in some embodiments, the weight ratio of the compound of formula (I) or salt or ester thereof to ethametsulfuron-methyl or salt, carboxylic acid, carboxylate salt, or ester thereof is within the range of from about 1:15 to about 68:1. In certain embodiments, the weight ratio of the compound of formula (I) or salt or ester thereof to ethametsulfuron-methyl salt, carboxylic acid, carboxylate salt, or ester thereof is within the range of from about 1:9 to about 8:1. In certain embodiments, the compositions comprise the compound of formula (I) or its benzyl or n-butyl ester and ethametsulfuron-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 330 gai/ha based on the total amount of active ingredients in the composition. In certain embodiments, the composition is applied at an application rate of from about 7 grams active ingredient per hectare (gai/ha) to about 55 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and ethametsulfuron-methyl or salt, carboxylic acid, carboxylate salt, or ester thereof, e.g., sequentially or simultaneously. In some embodiments, the ethametsulfuron-methyl or salt, carboxylic acid, carboxylate salt, or ester thereof is applied at a rate from about 4.4 gai/ha to about 30 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and ethametsulfuron-methyl.

In certain embodiments of the compositions and methods described herein, the compound of formula (I) or salt or ester thereof is used in combination with ethoxysulfuron or salt thereof. With respect to the compositions, in some embodiments, the weight ratio of the compound of formula (I) or salt or ester thereof to ethoxysulfuron or salt or ester thereof is within the range of from about 1:66 to about 40:1. In certain embodiments, the weight ratio of the compound of formula (I) or salt or ester thereof to ethoxysulfuron or salt or ester thereof is within the range of from about 1:9 to about 6:1. In certain embodiments, the weight ratio of the compound of formula (I) or salt or ester thereof to ethoxysulfuron or salt or ester thereof is within the range of from about 1:4 to about 6:1. In certain embodiments, the weight ratio of the compound of formula (I) or salt or ester thereof to ethoxysulfuron or salt thereof is within the range of from 12:1 to about 0.10:1. In certain embodiments, the weight ratio of the compound of formula (I) or salt or ester thereof to ethoxysulfuron or salt thereof is within the range of from 5.7:1 to about 0.30:1. In certain embodiments, the compositions provided herein comprise the compound of formula (I) or its benzyl ester and ethoxysulfuron. In one embodiment, the composition comprises the compound of formula (I) and ethoxysulfuron, wherein the weight ratio of the compound of formula (I) to ethoxysulfuron is from about 5.7:1 to about 0.71:1. In one embodiment, the composition comprises the benzyl ester of the compound of formula (I) and ethoxysulfuron, wherein the weight ratio of the benzyl ester of the compound of formula (I) to ethoxysulfuron is from about 2.3:1 to about 0.30:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 9 grams active ingredient per hectare (gai/ha) to about 420 gai/ha based on the total amount of active ingredients in the composition. In certain embodiments, the composition is applied at an application rate of from about 12 grams active ingredient per hectare (gai/ha) to about 70 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and ethoxysulfuron or salt thereof, e.g., sequentially or simultaneously. In some embodiments, the ethoxysulfuron or salt thereof is applied at a rate from about 7.5 gai/ha to about 120 gai/ha and the compound of formula (I) of salt or ester thereof is applied at a rate from about 2 gae/ha to about 300 gae/ha. In some embodiments, the ethoxysulfuron or salt thereof is applied at a rate from about 3 gai/ha to about 30 gai/ha and the compound of formula (I) of salt or ester thereof is applied at a rate from about 2 g acid equivalent per hectare (gae/ha) to about 80 gae/ha. In some embodiments, the ethoxysulfuron or salt thereof is applied at a rate from about 7.5 gai/ha to about 15 gai/ha and the compound of formula (I) of salt or ester thereof is applied at a rate from about 4 g acid equivalent per hectare (gae/ha) to about 42 gae/ha. In certain embodiments, the methods utilize the compound of formula (I) or its benzyl ester and ethoxysulfuron. In one embodiment, the methods utilize the compound of formula (I) and ethoxysulfuron, wherein the compound of formula (I) is applied at a rate of from about 10.6 to about 42.4 gai/ha, and the ethoxysulfuron is applied at a rate of from about 7.5 to about 15 gai/ha. In one embodiment, the methods utilize the compound of formula (I) and ethoxysulfuron, wherein the compound of formula (I) is applied at a rate of from about 10.6 to about 120 gai/ha, and the ethoxysulfuron is applied at a rate of from about 7.5 to about 30 gai/ha. In one embodiment, the methods utilize the benzyl ester of the compound of formula (I) and ethoxysulfuron, wherein the benzyl ester of the compound of formula (I) is applied at a rate of from about 4.38 to about 42.4 ai/ha, and the ethoxysulfuron is applied at a rate of from about 7.5 to about 70 gai/ha. In certain embodiments, the methods and compositions utilizing the compound of formula (I) or salt or ester thereof in combination with ethoxysulfuron or salt thereof are used to control ECHOR, BRAPP, CYPIR, ISCRU or LEFCH.

In certain embodiments of the compositions and methods described herein, the compound of formula (I) or salt or ester thereof is used in combination with flazasulfuron or salt thereof. With respect to the compositions, in some embodiments, the weight ratio of the compound of formula (I) or salt or ester thereof to flazasulfuron or salt or ester thereof is within the range of from about 1:50 to about 68:1. In certain embodiments, the weight ratio of the compound of formula (I) or salt or ester thereof to flazasulfuron or salt or ester thereof is within the range of from 1:23 to about 8:1. In certain embodiments, the weight ratio of the compound of formula (I) or salt or ester thereof to flazasulfuron or salt or ester thereof is within the range of from 1:13 to about 1:1. In certain embodiments, the compositions provided herein comprise the compound of formula (I) or its benzyl or n-butyl ester and flazasulfuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 400 gai/ha based on the total amount of active ingredients in the composition. In certain embodiments, the composition is applied at an application rate of from about 7 grams active ingredient per hectare (gai/ha) to about 85 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flazasulfuron or salt thereof, e.g., sequentially or simultaneously. In some embodiments, the flazasulfuron or salt or ester thereof is applied at a rate from about 4.4 gai/ha to about 100 gai/ha and the compound of formula (I) of salt or ester thereof is applied at a rate from about 2 gae/ha to about 300 gae/ha. In certain embodiments, the methods utilize the compound of formula (I) or its benzyl of n-butyl ester and flazasulfuron. In some embodiments, the flazasulfuron or salt or ester thereof is applied at a rate from about 25 gai/ha to about 100 gai/ha and the compound of formula (I) of salt or ester thereof is applied at a rate from about 4 gae/ha to about 42 gae/ha. In certain embodiments, the methods utilize the compound of formula (I) or its benzyl of n-butyl ester and flazasulfuron. In certain embodiments, the methods and compositions utilizing the compound of formula (I) or salt or ester thereof in combination with flazasulfuron or salt thereof are used to control IPOHE, LEFCH or SETFA.

In certain embodiments of the compositions and methods described herein, the compound of formula (I) or salt or ester thereof is used in combination with flucetsulfuron or salt thereof. With regard to the compositions, in some embodiments, the weight ratio of the compound of formula (I) or salt or ester thereof to flucetsulfuron or salt thereof is within the range of from about 1:20 to about 60:1. In certain embodiments, the weight ratio of the compound of formula (I) or salt or ester thereof to flucetsulfuron or salt thereof is within the range of from about 1:5 to about 7:1. In certain embodiments, the weight ratio of the compound of formula (I) or salt or ester thereof to flucetsulfuron or salt thereof is within the range of from about 700:1 to about 4:1. In certain embodiments, the weight ratio of the compound of formula (I) or salt thereof to flucetsulfuron or salt thereof is within the range of from about 350:1 to about 9:1. In certain embodiments, the compositions provided herein comprise the compound of formula (I) or its benzyl ester and flucetsulfuron. In one embodiment, the composition comprises the compound of formula (I) and flucetsulfuron, wherein the weight ratio of the compound of formula (I) to flucetsulfuron is about 350:1 to about 9:1. In one embodiment, the composition comprises the benzyl ester of the compound of formula (I) and flucetsulfuron, wherein the weight ratio of the benzyl ester of the compound of formula (I) to flucetsulfuron is about 175:1 to about 40:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (gai/ha) to about 340 gai/ha based on the total amount of active ingredients in the composition. In certain embodiments, the composition is applied at an application rate of from about 10 grams active ingredient per hectare (gai/ha) to about 60 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flucetsulfuron or salt thereof, e.g., sequentially or simultaneously. In some embodiments, the flucetsulfuron or salt or ester thereof is applied at a rate from about 5 gai/ha to about 40 gai/ha and the compound of formula (I) of salt or ester thereof is applied at a rate from about 2 gae/ha to about 300 gae/ha. In some embodiments, the flucetsulfuron or salt thereof is applied at a rate from about 0.025 gai/ha to about 0.4 gai/ha and the compound of formula (I) of salt or ester thereof is applied at a rate from about 2 g acid equivalent per hectare (gae/ha) to about 70 gae/ha. In some embodiments, the flucetsulfuron or salt thereof is applied at a rate from about 0.05 gai/ha to about 0.2 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I) or its benzyl ester and flucetsulfuron. In one embodiment, the methods utilize the compound of formula (I) and flucetsulfuron, wherein the compound of formula (I) is applied at a rate of from about 4.38 to about 35 gai/ha, and the flucetsulfuron is applied at a rate of from about 0.05 to about 10 gai/ha. In one embodiment, the methods utilize the benzyl ester of the compound of formula (I) and flucetsulfuron, wherein the benzyl ester of the compound of formula (I) is applied at a rate of from about 8.75 to about 120 gai/ha, and the flucetsulfuron is applied at a rate of about 0.05 to about 35 gai/ha. In one embodiment, the methods utilize the benzyl ester of the compound of formula (I) and flucetsulfuron, wherein the benzyl ester of the compound of formula (I) is applied at a rate of from about 8.75 to about 17.5 gai/ha, and the flucetsulfuron is applied at a rate of about 0.1 to about 10 gai/ha.

In certain embodiments, the methods and compositions utilizing the compound of formula (I) or salt or ester thereof in combination with flucetsulfuron or salt thereof are used to control LEFCH, IPOHE, CYPIR, BRAPP, SCPJU, or ECHOR.

In certain embodiments of the compositions and methods described herein, the compound of formula (I) or salt or ester thereof is used in combination with flupyrsulfuron-methyl sodium or non-ionic form, carboxylic acid, carboxylate salt, or ester thereof or other flupyrsulfuron-methyl salt. With respect to the compositions, in some embodiments, the weight ratio of the compound of formula (I) or salt or ester thereof to flupyrsulfuron-methyl sodium or non-ionic form, carboxylic acid, carboxylate salt, or ester thereof or other flupyrsulfuron-methyl salt is within the range of from about 1:10 to about 150:1. In certain embodiments, the weight ratio of the compound of formula (I) or salt or ester thereof to flupyrsulfuron-methyl sodium or non-ionic form, carboxylic acid, carboxylate salt, or ester thereof or other flupyrsulfuron-methyl salt is within the range of from about 1:2 to about 35:1. In certain embodiments, the weight ratio of the compound of formula (I) or salt or ester thereof to flupyrsulfuron-methyl sodium or non-ionic form, carboxylic acid, carboxylate salt, or ester thereof or other flupyrsulfuron-methyl salt is within the range of from about 3.5:1 to about 0.90:1. In certain embodiments, the weight ratio of the compound of formula (I) or salt or ester thereof to flupyrsulfuron-methyl sodium or non-ionic form, carboxylic acid, carboxylate salt, or ester thereof or other flupyrsulfuron-methyl salt is about 1.75:1. In certain embodiments, the compositions provided herein comprise the benzyl ester of the compound of formula (I) and flupyrsulfuron-methyl sodium. In one embodiment, the composition comprises the benzyl ester of the compound of formula (I) and flupyrsulfuron-methyl sodium, wherein the weight ratio of the benzyl ester of the compound of formula (I) to flupyrsulfuron-methyl sodium is about 1.75:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 320 gai/ha based on the total amount of active ingredients in the composition. In certain embodiments, the composition is applied at an application rate of from about 10 grams active ingredient per hectare (gai/ha) to about 90 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flupyrsulfuron-methyl sodium or non-ionic form, carboxylic acid, carboxylate salt, or ester thereof or other flupyrsulfuron-methyl salt, e.g., sequentially or simultaneously. In some embodiments, the flupyrsulfuron-methyl sodium or non-ionic form, carboxylic acid, carboxylate salt, or ester thereof or other flupyrsulfuron-methyl salt is applied at a rate from about 2 gai/ha to about 20 gai/ha and the compound of formula (I) of salt or ester thereof is applied at a rate from about 2 gae/ha to about 300 gae/ha. In some embodiments, the flupyrsulfuron-methyl sodium or non-ionic form, carboxylic acid, carboxylate salt, or ester thereof or other flupyrsulfuron-methyl salt is applied at a rate from about 2.5 gai/ha to about 10 gai/ha and the compound of formula (I) of salt or ester thereof is applied at a rate from about 4 g acid equivalent per hectare (gae/ha) to about 17 gae/ha. In some embodiments, the flupyrsulfuron-methyl sodium or non-ionic form, carboxylic acid, carboxylate salt, or ester thereof or other flupyrsulfuron-methyl salt thereof is applied at a rate from about 4 to about 6 gai/ha and the compound of formula (I) of salt or ester thereof is applied at a rate about 7 to about 10 gae/ha. In certain embodiments, the methods utilize the benzyl ester of the compound of formula (I) and flupyrsulfuron-methyl sodium. In one embodiment, the methods utilize the benzyl ester of the compound of formula (I) and flupyrsulfuron-methyl sodium, wherein the benzyl ester of the compound of formula (I) is applied at a rate of about 8.75 gai/ha, and the flupyrsulfuron-methyl sodium is applied at a rate of about 5 gai/ha. In certain embodiments, the methods and compositions utilizing the compound of formula (I) or salt or ester thereof in combination with flupyrsulfuron-methyl sodium or salt thereof are used to control VERPE or CIRAR.

In certain embodiments of the compositions and methods described herein, the compound of formula (I) or salt or ester thereof is used in combination with foramsulfuron or salt thereof. With respect to the compositions, in some embodiments, the weight ratio of the compound of formula (I) or salt or ester thereof to foramsulfuron or salt thereof is within the range of from about 1:30 to about 68:1. In certain embodiments, the weight ratio of the compound of formula (I) or salt or ester thereof to foramsulfuron or salt thereof is within the range of from about 1:18 to about 8:1. In certain embodiments, the weight ratio of the compound of formula (I) or salt or ester thereof to foramsulfuron or salt thereof is within the range of from about 1:5 to about 2:1. In certain embodiments, the compositions provided herein comprise the compound of formula (I) or its benzyl or n-butyl ester and foramsulfuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 360 gai/ha based on the total amount of active ingredients in the composition. In certain embodiments, the composition is applied at an application rate of from about 7 grams active ingredient per hectare (gai/ha) to about 75 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and foramsulfuron or salt thereof, e.g., sequentially or simultaneously. In some embodiments, the foramsulfuron or salt thereof is applied at a rate from about 4.4 gai/ha to about 60 gai/ha and the compound of formula (I) of salt or ester thereof is applied at a rate from about 2 gae/ha to about 300 gae/ha. In some embodiments, the foramsulfuron or salt thereof is applied at a rate from about 4.4 gai/ha to about 40 gai/ha and the compound of formula (I) of salt or ester thereof is applied at a rate from about 4 gae/ha to about 100 gae/ha. In certain embodiments, the methods utilize compound of formula (I) or its benzyl or n-butyl ester and foramsulfuron. In certain embodiments, the methods and compositions utilizing the compound of formula (I) or salt or ester thereof in combination with foramsulfuron or salt thereof are used to control LEFCH.

In certain embodiments of the compositions and methods described herein, the compound of formula (I) or salt or ester thereof is used in combination with imazosulfuron or salt thereof. With respect to the compositions, in some embodiments, the weight ratio of the compound of formula (I) or salt or ester thereof to imazosulfuron or salt thereof is within the range of from about 1:500 to about 14:1. In certain embodiments, the weight ratio of the compound of formula (I) or salt or ester thereof to imazosulfuron or salt thereof is within the range of from about 1:18 to about 4:1. In certain embodiments, the weight ratio of the compound of formula (I) or salt or ester thereof to imazosulfuron or salt thereof is within the range of from about 1:0.60 to about 1:20. In certain embodiments, the weight ratio of the compound of formula (I) or salt or ester thereof to imazosulfuron or salt thereof is within the range of from about 1:1.2 to about 1:10.3. In certain embodiments, the compositions provided herein comprise the compound of formula (I) or its benzyl or n-butyl ester and imazosulfuron. In one embodiment, the composition comprises the compound of formula (I) and imazosulfuron, wherein the weight ratio of the compound of formula (I) and imazosulfuron is from about 1:1.2 to about 1:5.1. In one embodiment, the composition comprises the benzyl ester of the compound of formula (I) and imazosulfuron, wherein the weight ratio of the benzyl ester of the compound of formula (I) and imazosulfuron is from about 1:1.2 to about 1:10.3. In one embodiment, the composition comprises the n-butyl ester of the compound of formula (I) and imazosulfuron, wherein the weight ratio of the n-butyl ester of the compound of formula (I) and imazosulfuron is from about 1:2.4 to about 1:4.8. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 23 grams active ingredient per hectare (gai/ha) to about 1300 gai/ha based on the total amount of active ingredients in the composition. In certain embodiments, the composition is applied at an application rate of from about 30 grams active ingredient per hectare (gai/ha) to about 240 gai/ha based on the total amount of active ingredients in the composition. In some embodiments, the imazosulfuron or salt thereof is applied at a rate from about 21 gai/ha to about 1000 gai/ha and the compound of formula (I) of salt or ester thereof is applied at a rate from about 2 gae/ha to about 300 gae/ha. In some embodiments, the imazosulfuron or salt thereof is applied at a rate from about 10 gai/ha to about 280 gai/ha and the compound of formula (I) of salt or ester thereof is applied at a rate from about 2 g acid equivalent per hectare (gae/ha) to about 140 gae/ha. In some embodiments, the imazosulfuron or salt thereof is applied at a rate from about 20 gai/ha to about 170 gai/ha and the compound of formula (I) of salt or ester thereof is applied at a rate from about 4.38 g acid equivalent per hectare (gae/ha) to about 70 gae/ha. In certain embodiments, the methods utilize the compound of formula (I) or its benzyl or n-butyl ester and imazosulfuron. In one embodiment, the methods utilize the compound of formula (I) and imazosulfuron, wherein the compound of formula (I) is applied at a rate of from about 8.75 g acid equivalent per hectare (gae/ha) to about 70 gae/ha, and the imazosulfuron is applied at a rate of from about 21 gai/ha to about 168 gai/ha. In one embodiment, the methods utilize the benzyl ester of the compound of formula (I) and imazosulfuron, wherein the benzyl ester of the compound of formula (I) is applied at a rate of from about 4.38 g acid equivalent per hectare (gae/ha) to about 70 gae/ha, and the imazosulfuron is applied at a rate of from about 21 gai/ha to about 168 gai/ha. In one embodiment, the methods utilize the n-butyl ester of the compound of formula (I) and imazosulfuron, wherein the n-butyl ester of the compound of formula (I) is applied at a rate of from about 35 g acid equivalent per hectare (gae/ha) to about 70 gae/ha, and the imazosulfuron is applied at a rate of about 168 gai/ha. In certain embodiments, the methods and compositions utilizing the compound of formula (I) or salt or ester thereof in combination with imazosulfuron or salt thereof are used to control DIGSA, LEFCH, ECHCO, or SCPMA.

In certain embodiments of the compositions and methods described herein, the compound of formula (I) or salt or ester thereof is used in combination with iodosulfuron-methyl sodium or non-ionic form, carboxylic acid, carboxylate salt, or ester thereof or other iodosulfuron-methyl salt. With respect to the compositions, in some embodiments, the weight ratio of the compound of formula (I) or salt or ester thereof to iodosulfuron-methyl sodium or non-ionic form, carboxylic acid, carboxylate salt, or ester thereof or other iodosulfuron-methyl salt is within the range of from about 1:5 to about 300:1. In certain embodiments, the weight ratio of the compound of formula (I) or salt or ester thereof to iodosulfuron-methyl sodium or non-ionic form, carboxylic acid, carboxylate salt, or ester thereof or other iodosulfuron-methyl salt is within the range of from about 1:1 to about 50:1. In certain embodiments, the weight ratio of the compound of formula (I) or salt or ester thereof to iodosulfuron-methyl sodium or non-ionic form, carboxylic acid, carboxylate salt, or ester thereof or other iodosulfuron-methyl salt is within the range of from about 9:1 to about 1.2:1. In certain embodiments, the weight ratio of the compound of formula (I) or salt or ester thereof to iodosulfuron-methyl sodium or non-ionic form, carboxylic acid, carboxylate salt, or ester thereof or other iodosulfuron-methyl salt is within the range of from about 4.5:1 to about 2.5:1. In certain embodiments, the weight ratio of the compound of formula (I) or salt or ester thereof to iodosulfuron-methyl sodium or non-ionic form, carboxylic acid, carboxylate salt, or ester thereof or other iodosulfuron-methyl salt is about 3.5:1. In certain embodiments, the compositions provided herein comprise the benzyl ester of the compound of formula (I) and iodosulfuron-methyl sodium. In one embodiment, the composition comprises the benzyl ester of the compound of formula (I) and iodosulfuron-methyl sodium, wherein the weight ratio of the benzyl ester of the compound of formula (I) to iodosulfuron-methyl sodium is about 3.5:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 3 grams active ingredient per hectare (gai/ha) to about 310 gai/ha based on the total amount of active ingredients in the composition. In certain embodiments, the composition is applied at an application rate of from about 10 grams active ingredient per hectare (gai/ha) to about 60 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and iodosulfuron-methyl sodium or non-ionic form, carboxylic acid, carboxylate salt, or ester thereof or other iodosulfuron-methyl salt, e.g., sequentially or simultaneously. In some embodiments, the iodosulfuron-methyl sodium or non-ionic form, carboxylic acid, carboxylate salt, or ester thereof or other iodosulfuron-methyl salt is applied at a rate from about 1 gai/ha to about 10 gai/ha and the compound of formula (I) of salt or ester thereof is applied at a rate from about 2 gae/ha to about 300 gae/ha. In some embodiments, the iodosulfuron-methyl sodium or non-ionic form, carboxylic acid, carboxylate salt, or ester thereof or other iodosulfuron-methyl salt is applied at a rate from about 0.50 gai/ha to about 8 gai/ha and the compound of formula (I) of salt or ester thereof is applied at a rate from about 3.5 g acid equivalent per hectare (gae/ha) to about 20 gae/ha. In some embodiments, the iodosulfuron-methyl sodium or non-ionic form, carboxylic acid, carboxylate salt, or ester thereof or other iodosulfuron-methyl salt is applied at a rate from about 1 gai/ha to about 4 gai/ha and the compound of formula (I) of salt or ester thereof is applied at a rate from about 7 g acid equivalent per hectare (gae/ha) to about 10 gae/ha. In some embodiments, the iodosulfuron-methyl sodium or non-ionic form, carboxylic acid, carboxylate salt, or ester thereof or other iodosulfuron-methyl salt is applied at a rate of about 2.5 gai/ha and the compound of formula (I) of salt or ester thereof is applied at a rate of about 8.75 g acid equivalent per hectare (gae/ha). In certain embodiments, the methods utilize the benzyl ester of the compound of formula (I) and iodosulfuron-methyl sodium. In one embodiment, the methods utilize the benzyl ester of the compound of formula (I) and iodosulfuron-methyl sodium, wherein the benzyl ester of the compound of formula (I) is applied at a rate of about 8.75 gae/ha to about 32 gae/ha, and the iodosulfuron-methyl sodium is applied at a rate of about 2.5 gai/ha to about 5 gai/ha. In certain embodiments, the methods and compositions utilizing the compound of formula (I) or salt or ester thereof in combination with iodosulfuron-methyl sodium or non-ionic form, carboxylic acid, carboxylate salt, or ester thereof or other iodosulfuron-methyl salt are used to control IPOHE, VIOTR, MATCH, or CIRAR.

In certain embodiments of the compositions and methods described herein, the compound of formula (I) or salt or ester thereof is used in combination with iofensulfuron or salt thereof. With respect to the compositions, in some embodiments, the weight ratio of the compound of formula (I) or salt or ester thereof to iofensulfuron or salt or ester thereof is within the range of from about 1:25 to about 600:1. In certain embodiments, the weight ratio of the compound of formula (I) or salt or ester thereof to iofensulfuron or salt or ester thereof is within the range of from about 1:9 to about 75:1. In certain embodiments, the compositions provided herein comprise the compound of formula (I) or its benzyl or n-butyl ester and iofensulfuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 2.5 grams active ingredient per hectare (gai/ha) to about 350 gai/ha based on the total amount of active ingredients in the composition. In certain embodiments, the composition is applied at an application rate of from about 3 grams active ingredient per hectare (gai/ha) to about 55 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and iofensulfuron or salt thereof, e.g., sequentially or simultaneously. In some embodiments, the iofensulfuron or salt or ester thereof is applied at a rate from about 0.5 gai/ha to about 50 gai/ha and the compound of formula (I) of salt or ester thereof is applied at a rate from about 2 g acid equivalent per hectare (gae/ha) to about 300 gae/ha. In certain embodiments, the methods utilize the compound of formula (I) or its benzyl or n-butyl ester and iofensulfuron.

In certain embodiments of the compositions and methods described herein, the compound of formula (I) or salt or ester thereof is used in combination with mesosulfuron-methyl or salt, carboxylic acid, carboxylate salt, or ester thereof. With respect to the compositions, in some embodiments, the weight ratio of the compound of formula (I) or salt or ester thereof to mesosulfuron-methyl or salt, carboxylic acid, carboxylate salt, or ester thereof is within the range of from about 1:8 to about 300:1. In certain embodiments, the weight ratio of the compound of formula (I) or salt or ester thereof to mesosulfuron-methyl or salt, carboxylic acid, carboxylate salt, or ester thereof is within the range of from 1:2 to about 50:1. In certain embodiments, the weight ratio of the compound of formula (I) or salt or ester thereof to mesosulfuron-methyl or salt, carboxylic acid, carboxylate salt, or ester thereof is within the range of from about 1:1 to about 8:1. In certain embodiments, the weight ratio of the compound of formula (I) or salt or ester thereof to mesosulfuron-methyl or salt, carboxylic acid, carboxylate salt, or ester thereof is within the range of from about 2:1 to about 4:1. In certain embodiments, the weight ratio of the compound of formula (I) or salt or ester thereof to mesosulfuron-methyl or salt, carboxylic acid, carboxylate salt, or ester thereof is about 2.9:1. In certain embodiments, the compositions provided herein comprise the benzyl ester of the compound of formula (I) and mesosulfuron-methyl. In one embodiment, the composition comprises the benzyl ester of the compound of formula (I) and mesosulfuron-methyl, wherein the weight ratio of the benzyl ester of the compound of formula (I) to mesosulfuron-methyl is about 2.9:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 3 grams active ingredient per hectare (gai/ha) to about 315 gai/ha based on the total amount of active ingredients in the composition. In certain embodiments, the composition is applied at an application rate of from about 10 grams active ingredient per hectare (gai/ha) to about 65 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and mesosulfuron-methyl or salt, carboxylic acid, carboxylate salt, or ester thereof, e.g., sequentially or simultaneously. In some embodiments, the mesosulfuron-methyl or salt, carboxylic acid, carboxylate salt, or ester thereof is applied at a rate from about 1 gai/ha to about 15 gai/ha and the compound of formula (I) of salt or ester thereof is applied at a rate from about 2 gae/ha to about 300 gae/ha. In some embodiments, the mesosulfuron-methyl salt, carboxylic acid, carboxylate salt, or ester thereof is applied at a rate from about 1 gai/ha to about 8 gai/ha and the compound of formula (I) of salt or ester thereof is applied at a rate from about 3.5 g acid equivalent per hectare (gae/ha) to about 20 gae/ha. In some embodiments, the mesosulfuron-methyl or salt, carboxylic acid, carboxylate salt, or ester thereof is applied at a rate from about 2 gai/ha to about 4 gai/ha and the compound of formula (I) of salt or ester thereof is applied at a rate from about 7 g acid equivalent per hectare (gae/ha) to about 10 gae/ha. In some embodiments, the mesosulfuron-methyl salt, carboxylic acid, carboxylate salt, or ester thereof is applied at a rate of about 3 gai/ha and the compound of formula (I) of salt or ester thereof is applied at a rate of about 8.75 g acid equivalent per hectare (gae/ha). In certain embodiments, the methods utilize the benzyl ester of the compound of formula (I) and mesosulfuron-methyl. In one embodiment, the methods utilize the benzyl ester of the compound of formula (I) and amidosulfuron, wherein the benzyl ester of the compound of formula (I) is applied at a rate of about 8.75 gai/ha, and the mesosulfuron-methyl is applied at a rate of about 3 gai/ha. In certain embodiments, the methods and compositions utilizing the compound of formula (I) or salt or ester thereof in combination with mesosulfuron-methyl or salt, carboxylic acid, carboxylate salt, or ester thereof are used to control VERPE, MATCH, or CIRAR.

In certain embodiments of the compositions and methods described herein, the compound of formula (I) or salt or ester thereof is used in combination with metsulfuron-methyl or salt, carboxylic acid, carboxylate salt, or ester thereof. With respect to the compositions, in some embodiments, the weight ratio of the compound of formula (I) or salt or ester thereof to metsulfuron-methyl or salt, carboxylic acid, carboxylate salt, or ester thereof is within the range of from about 1:6 to about 300:1. In certain embodiments, the weight ratio of the compound of formula (I) or salt or ester thereof to metsulfuron-methyl or salt, carboxylic acid, carboxylate salt, or ester thereof is within the range of from 1:30 to about 40:1. In certain embodiments, the weight ratio of the compound of formula (I) or salt or ester thereof to metsulfuron-methyl or salt, carboxylic acid, carboxylate salt, or ester thereof is within the range of from about 16:1 to about 1:7. In certain embodiments, the weight ratio of the compound of formula (I) or salt or ester thereof to metsulfuron-methyl or salt, carboxylic acid, carboxylate salt, or ester thereof is within the range of from about 8:1 to about 1:3.4. In certain embodiments, the compositions provided herein comprise the compound of formula (I) or its benzyl ester and metsulfuron-methyl. In one embodiment, the composition comprises the compound of formula (I) and metsulfuron-methyl, wherein the weight ratio of the compound of formula (I) and metsulfuron-methyl is about 5.7:1 to about 1.1.4. In one embodiment, the composition comprises the benzyl ester of the compound of formula (I) and metsulfuron-methyl, wherein the weight ratio of the benzyl ester of the compound of formula (I) and metsulfuron-methyl is about 8:1 to about 1:3.4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 3 grams active ingredient per hectare (gai/ha) to about 315 gai/ha based on the total amount of active ingredients in the composition. In certain embodiments, the composition is applied at an application rate of from about 3 grams active ingredient per hectare (gai/ha) to about 75 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and metsulfuron-methyl or salt, carboxylic acid, carboxylate salt, or ester thereof or salt thereof, e.g., sequentially or simultaneously. In some embodiments, the metsulfuron-methyl or salt, carboxylic acid, carboxylate salt, or ester thereof is applied at a rate from about 1 gai/ha to about 15 gai/ha and the compound of formula (I) of salt or ester thereof is applied at a rate from about 2 gae/ha to about 300 gae/ha. In some embodiments, the metsulfuron-methyl or salt, carboxylic acid, carboxylate salt, or ester thereof is applied at a rate from about 0.50 gai/ha to about 30 gai/ha and the compound of formula (I) of salt or ester thereof is applied at a rate from about 1 g acid equivalent per hectare (gae/ha) to about 84 gae/ha. In some embodiments, the metsulfuron-methyl or salt, carboxylic acid, carboxylate salt, or ester thereof is applied at a rate from about 1.1 gai/ha to about 15 gai/ha and the compound of formula (I) of salt or ester thereof is applied at a rate from about 2.2 g acid equivalent per hectare (gae/ha) to about 42 gae/ha. In certain embodiments, the methods utilize the compound of formula (I) or its benzyl ester and metsulfuron-methyl. In one embodiment, the methods utilize the compound of formula (I) and metsulfuron-methyl, wherein the compound of formula (I) is applied at a rate of from about 2.2 g acid equivalent per hectare (gae/ha) to about 42.4 gae/ha, and the metsulfuron-methyl is applied at a rate of from about 1.1 gai/ha to about 15 gai/ha. In one embodiment, the methods utilize the benzyl ester of the compound of formula (I) and metsulfuron-methyl, wherein the benzyl ester of the compound of formula (I) is applied at a rate of from about 4.38 g acid equivalent per hectare (gae/ha) to about 42.4 gae/ha, and the metsulfuron-methyl is applied at a rate of from about 1.1 gai/ha to about 15 gai/ha. In certain embodiments, the methods and compositions utilizing the compound of formula (I) or salt or ester thereof in combination with metsulfuron-methyl or salt, carboxylic acid, carboxylate salt, or ester thereof are used to control BRAPP, ECHOR, MATCH, CIRAR, SIDSP, CASOB, or POROL.

In certain embodiments of the compositions and methods described herein, the compound of formula (I) or salt or ester thereof is used in combination with nicosulfuron or salt thereof. With respect to the composition, in some embodiments, the weight ratio of the compound of formula (I) or salt or ester thereof to nicosulfuron or salt thereof is within the range of from about 1:35 to about 34:1. In certain embodiments, the weight ratio of the compound of formula (I) or salt or ester thereof to nicosulfuron or salt thereof is within the range of from about 1:8 to about 5:1. In certain embodiments, the weight ratio of the compound of formula (I) or salt or ester thereof to nicosulfuron or salt thereof is within the range of from about 5:1 to about 1:13. In certain embodiments, the weight ratio of the compound of formula (I) or salt or ester thereof to nicosulfuron or salt thereof is within the range of from about 2.4:1 to about 1:6.6. In certain embodiments, the compositions provided herein comprise the compound of formula (I) or its benzyl ester and nicosulfuron. In one embodiment, the composition comprises the compound of formula (I) and nicosulfuron, wherein the weight ratio of the compound of formula (I) and nicosulfuron is about 2.4:1 to about 1:6.6. In one embodiment, the composition comprises the benzyl ester of the compound of formula (I) and nicosulfuron, wherein the weight ratio of the benzyl ester of the compound of formula (I) and nicosulfuron is about 2:1 to about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 10 grams active ingredient per hectare (gai/ha) to about 370 gai/ha based on the total amount of active ingredients in the composition. In certain embodiments, the composition is applied at an application rate of from about 13 grams active ingredient per hectare (gai/ha) to about 80 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and nicosulfuron or salt thereof, e.g., sequentially or simultaneously. In some embodiments, the nicosulfuron or salt or ester thereof is applied at a rate from about 4.4 gai/ha to about 70 gai/ha and the compound of formula (I) of salt or ester thereof is applied at a rate from about 2 gae/ha to about 300 gae/ha. In some embodiments, the nicosulfuron or salt thereof is applied at a rate from about 4 gai/ha to about 70 gai/ha and the compound of formula (I) of salt or ester thereof is applied at a rate from about 2 g acid equivalent per hectare (gae/ha) to about 82 gae/ha. In some embodiments, the nicosulfuron or salt thereof is applied at a rate from about 8.75 gai/ha to about 35 gai/ha and the compound of formula (I) of salt or ester thereof is applied at a rate from about 4.38 g acid equivalent per hectare (gae/ha) to about 42.4 gae/ha. In certain embodiments, the methods utilize the compound of formula (I) or its benzyl ester and nicosulfuron. In one embodiment, the methods utilize the compound of formula (I) and nicosulfuron, wherein the compound of formula (I) is applied at a rate of from about 5.3 g acid equivalent per hectare (gae/ha) to about 42.4 gae/ha, and the nicosulfuron is applied at a rate of from about 8.75 gai/ha to about 35 gai/ha. In one embodiment, the methods utilize the benzyl ester of the compound of formula (I) and nicosulfuron, wherein the benzyl ester of the compound of formula (I) is applied at a rate of from about 4.38 g acid equivalent per hectare (gae/ha) to about 42.4 gae/ha, and the nicosulfuron is applied at a rate of from about 8.75 gai/ha to about 35 gai/ha. In certain embodiments, the methods and compositions utilizing the compound of formula (I) or salt or ester thereof in combination with nicosulfuron salt thereof are used to control ECHOR, CYPRO, LEFCH, DIGSA, CYPES, or CYPIR.

In certain embodiments of the compositions and methods described herein, the compound of formula (I) or salt or ester thereof is used in combination with orthosulfamuron or salt thereof. In some embodiments, the weight ratio of the compound of formula (I) or salt thereof to orthosulfamuron or salt or ester thereof is within the range of from about 1:50 to about 40:1. In certain embodiments, the weight ratio of the compound of formula (I) or salt or ester thereof to orthosulfamuron or salt thereof is within the range of from about 1:14 to about 11:1. In certain embodiments, the weight ratio of the compound of formula (I) or salt or ester thereof to orthosulfamuron or salt thereof is within the range of from about 1:1 to about 1:14. In certain embodiments, the weight ratio of the compound of formula (I) or salt or ester thereof to orthosulfamuron or salt thereof is within the range of from about 2.3:1 to about 1:6.8. In certain embodiments, the compositions provided herein comprise the compound of formula (I) or its benzyl ester and orthosulfamuron. In one embodiment, the composition comprises the compound of formula (I) and orthosulfamuron, wherein the weight ratio of the compound of formula (I) and orthosulfamuron is about 2.3:1 to about 1.3.4. In one embodiment, the composition comprises the benzyl ester of the compound of formula (I) and orthosulfamuron, wherein the weight ratio of the benzyl ester of the compound of formula (I) and orthosulfamuron is about 2.3:1 to about 1:6.8. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 9 grams active ingredient per hectare (gai/ha) to about 400 gai/ha based on the total amount of active ingredients in the composition. In certain embodiments, the composition is applied at an application rate of from about 12 grams active ingredient per hectare (gai/ha) to about 145 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and orthosulfamuron or salt thereof, e.g., sequentially or simultaneously. In some embodiments, the orthosulfamuron or salt thereof is applied at a rate from about 7.5 gai/ha to about 100 gai/ha and the compound of formula (I) of salt or ester thereof is applied at a rate from about 2 gae/ha to about 300 gae/ha. In some embodiments, the orthosulfamuron or salt thereof is applied at a rate from about 3.8 gai/ha to about 120 gai/ha and the compound of formula (I) of salt or ester thereof is applied at a rate from about 2 g acid equivalent per hectare (gae/ha) to about 170 gae/ha. In some embodiments, the orthosulfamuron or salt thereof is applied at a rate from about 7.5 gai/ha to about 60 gai/ha and the compound of formula (I) of salt or ester thereof is applied at a rate from about 4.38 g acid equivalent per hectare (gae/ha) to about 84.8 gae/ha. In certain embodiments, the methods utilize the compound of formula (I) or its benzyl ester and orthosulfamuron. In one embodiment, the methods utilize the compound of formula (I) and orthosulfamuron, wherein the compound of formula (I) is applied at a rate of from about 4.38 g acid equivalent per hectare (gae/ha) to about 84.8 gae/ha, and the orthosulfamuron is applied at a rate of from about 7.5 gai/ha to about 60 gai/ha. In one embodiment, the methods utilize the benzyl ester of the compound of formula (I) and orthosulfamuron, wherein the benzyl ester of the compound of formula (I) is applied at a rate of from about 4.38 g acid equivalent per hectare (gae/ha) to about 70 gae/ha, and the orthosulfamuron is applied at a rate of from about 7.5 gai/ha to about 60 gai/ha. In certain embodiments, the methods and compositions utilizing the compound of formula (I) or salt or ester thereof in combination with orthosulfamuron or salt thereof are used to control ECHOR, LEFCH, CYPES, BRAPP, CYPIR, DIGSA or SCPMA.

In certain embodiments of the compositions and methods described herein, the compound of formula (I) or salt or ester thereof is used in combination with primisulfuron-methyl or salt, carboxylic acid, carboxylate salt, or ester thereof. With respect to the compositions, in some embodiments, the weight ratio of the compound of formula (I) or salt or ester thereof to primisulfuron-methyl or salt, carboxylic acid, carboxylate salt, or ester thereof is within the range of from about 1:20 to about 120:1. In certain embodiments, the weight ratio of the compound of formula (I) or salt or ester thereof to primisulfuron-methyl salt, carboxylic acid, carboxylate salt, or ester thereof is within the range of from about 1:9 to about 28:1. In certain embodiments, the weight ratio of the compound of formula (I) or salt or ester thereof to primisulfuron-methyl salt, carboxylic acid, carboxylate salt, or ester thereof is within the range of from about 1:4 to about 2:1. In certain embodiments, the compositions provided herein comprise the compound of formula (I) or its benzyl or n-butyl ester and primisulfuron-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 5 grams active ingredient per hectare (gai/ha) to about 340 gai/ha based on the total amount of active ingredients in the composition. In certain embodiments, the composition is applied at an application rate of from about 70 grams active ingredient per hectare (gai/ha) to about 110 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and primisulfuron-methyl or salt, carboxylic acid, carboxylate salt, or ester thereof, e.g., sequentially or simultaneously. In some embodiments, the primisulfuron-methyl or salt or ester thereof is applied at a rate from about 2.5 gai/ha to about 40 gai/ha and the compound of formula (I) of salt or ester thereof is applied at a rate from about 2 gae/ha to about 300 gae/ha. In some embodiments, the primisulfuron-methyl or salt or ester thereof is applied at a rate from about 15 gai/ha to about 30 gai/ha and the compound of formula (I) of salt or ester thereof is applied at a rate from about 8 gae/ha to about 20 gae/ha. In certain embodiments, the methods and compositions utilizing the compound of formula (I) or salt or ester thereof in combination with the primisulfuron-methyl or salt or ester thereof are used to control LEFCH.

In certain embodiments of the compositions and methods described herein, the compound of formula (I) or salt or ester thereof is used in combination with propyrisulfuron or salt thereof. With respect to the compositions, in some embodiments, the weight ratio of the compound of formula (I) or salt or ester thereof to propyrisulfuron or salt thereof is within the range of from about 1:50 to about 27:1. In certain embodiments, the weight ratio of the compound of formula (I) or salt thereof to propyrisulfuron or salt or ester thereof is within the range of from 1:10 to about 2:1. In certain embodiments, the weight ratio of the compound of formula (I) or salt or ester thereof to propyrisulfuron or salt thereof is within the range of from about 1:0.7 to about 1:20. In certain embodiments, the weight ratio of the compound of formula (I) or salt or ester thereof to propyrisulfuron or salt thereof is within the range of from about 1:1.3 to about 1:10.3. In certain embodiments, the compositions provided herein comprise the compound of formula (I) or its benzyl ester and propyrisulfuron. In one embodiment, the composition comprises the compound of formula (I) and propyrisulfuron, wherein the weight ratio of the compound of formula (I) and propyrisulfuron is about 1:1.3 to about 1:5.1. In one embodiment, the composition comprises the benzyl ester of the compound of formula (I) and propyrisulfuron, wherein the weight ratio of the benzyl ester of the compound of formula (I) and propyrisulfuron is about 1:2.6 to about 1:10.3. In one embodiment, the composition comprises the benzyl ester of the compound of formula (I) and propyrisulfuron, wherein the weight ratio of the benzyl ester of the compound of formula (I) and propyrisulfuron is about 1:10 to about 3:1. With respect to the methods, in certain embodiments, the methods comprise contacting the undesirable vegetation or locus thereof or applying to the soil or water to prevent the emergence or growth of vegetation a composition described herein. The application rate will depend upon the particular type of weed to be controlled, the degree of control required, and the timing and method of application. In some embodiments, the composition is applied at an application rate of from about 12 grams active ingredient per hectare (gai/ha) to about 400 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and propyrisulfuron or salt thereof, e.g., sequentially or simultaneously. In certain embodiments, the composition is applied at an application rate of from about 15 grams active ingredient per hectare (gai/ha) to about 65 gai/ha based on the total amount of active ingredients in the composition. In some embodiments, the propyrisulfuron or salt thereof is applied at a rate from about 11 gai/ha to about 100 gai/ha and the compound of formula (I) of salt or ester thereof is applied at a rate from about 2 gae/ha to about 300 gae/ha. In some embodiments, the propyrisulfuron or salt thereof is applied at a rate from about 5 gai/ha to about 90 gai/ha and the compound of formula (I) of salt or ester thereof is applied at a rate from about 2 g acid equivalent per hectare (gae/ha) to about 40 gae/ha. In some embodiments, the propyrisulfuron or salt thereof is applied at a rate from about 11.25 gai/ha to about 45 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I) or its benzyl ester and propyrisulfuron. In one embodiment, the methods utilize the compound of formula (I) and propyrisulfuron, wherein the compound of formula (I) is applied at a rate of from about 8.75 g acid equivalent per hectare (gae/ha) to about 17.5 gae/ha, and the propyrisulfuron is applied at a rate of from about 22.5 gai/ha to about 45 gai/ha. In one embodiment, the methods utilize the benzyl ester of the compound of formula (I) and propyrisulfuron, wherein the benzyl ester of the compound of formula (I) is applied at a rate of about 4.38 g acid equivalent per hectare (gae/ha) to about 32 gae/ha, and the propyrisulfuron is applied at a rate of from about 11.25 gai/ha to about 45 gai/ha. In certain embodiments, the methods and compositions utilizing the compound of formula (I) or salt or ester thereof in combination with propyrisulfuron or salt thereof are used to control BRAPP, FIMMI, SCPMA or LEFCH.

In certain embodiments of the compositions and methods described herein, the compound of formula (I) or salt or ester thereof is used in combination with prosulfuron or salt thereof. With respect to the compositions, in some embodiments, the weight ratio of the compound of formula (I) or salt or ester thereof to prosulfuron or salt thereof is within the range of from about 1:20 to about 68:1. In certain embodiments, the weight ratio of the compound of formula (I) or salt or ester thereof to prosulfuron or salt thereof is within the range of from about 1:14 to about 8:1. In certain embodiments, the compositions provided herein comprise the compound of formula (I) or its benzyl or n-butyl ester and prosulfuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 340 gai/ha based on the total amount of active ingredients in the composition. In certain embodiments, the composition is applied at an application rate of from about 7 grams active ingredient per hectare (gai/ha) to about 65 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and prosulfuron or salt thereof, e.g., sequentially or simultaneously. In some embodiments, the prosulfuron or salt thereof is applied at a rate from about 4.4 gai/ha to about 40 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and prosulfuron.

In certain embodiments of the compositions and methods described herein, the compound of formula (I) or salt or ester thereof is used in combination with pyrimisulfan or salt or ester thereof. With respect to the compositions, in some embodiments, the weight ratio of the compound of formula (I) or salt or ester thereof to pyrimisulfan or salt or ester thereof is within the range of from about 1:100 to about 30:1. In certain embodiments, the weight ratio of the compound of formula (I) or salt or ester thereof to pyrimisulfan or salt or ester thereof is within the range of from 1:45 to about 10:1. In certain embodiments, the compositions provided herein comprise the compound of formula (I) or its benzyl or n-butyl ester and pyrimisulfan. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (gai/ha) to about 500 gai/ha based on the total amount of active ingredients in the composition. In certain embodiments, the composition is applied at an application rate of from about 15 grams active ingredient per hectare (gai/ha) to about 300 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyrimisulfan or salt or ester thereof, e.g., sequentially or simultaneously. In some embodiments, the pyrimisulfan or salt or ester thereof is applied at a rate from about 10 gai/ha to about 200 gai/ha and the compound of formula (I) of salt or ester thereof is applied at a rate from about 2 gae/ha to about 300 gae/ha. In certain embodiments, the methods utilize compound of formula (I) or its benzyl or n-butyl ester and pyrimisulfan.

In certain embodiments of the compositions and methods described herein, the compound of formula (I) or salt or ester thereof is used in combination with pyroxasulfone or salt thereof. With regard to the compositions, in some embodiments, the weight ratio of the compound of formula (I) or salt or ester thereof to pyroxasulfone or salt thereof is within the range of from about 1:500 to about 3:1. In certain embodiments, the weight ratio of the compound of formula (I) or salt or ester thereof to pyroxasulfone or salt thereof is within the range of from 1:136 to about 1:2. In certain embodiments, the compositions provided herein comprise the compound of formula (I) or its benzyl or n-butyl ester and pyroxasulfone. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 102 grams active ingredient per hectare (gai/ha) to about 1300 gai/ha based on the total amount of active ingredients in the composition. In certain embodiments, the composition is applied at an application rate of from about 105 grams active ingredient per hectare (gai/ha) to about 350 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyroxasulfone or salt thereof, e.g., sequentially or simultaneously. In some embodiments, the pyroxasulfone or salt thereof is applied at a rate from about 100 gai/ha to about 1000 gai/ha and the compound of formula (I) of salt or ester thereof is applied at a rate from about 2 g acid equivalent per hectare (gae/ha) to about 300 gae/ha. In certain embodiments, the methods utilize the compound of formula (I) or its benzyl or n-butyl ester and pyroxasulfone.

In certain embodiments of the compositions and methods described herein, the compound of formula (I) or salt or ester thereof is used in combination with rimsulfuron or salt thereof. With respect to the compositions, in some embodiments, the weight ratio of the compound of formula (I) or salt or ester thereof to rimsulfuron or salt or thereof is within the range of from about 1:10 to about 100:1. In certain embodiments, the weight ratio of the compound of formula (I) or salt or ester thereof to rimsulfuron or salt thereof is within the range of from about 1:4 to about 10:1. In certain embodiments, the weight ratio of the compound of formula (I) or salt or ester thereof to rimsulfuron or salt thereof is within the range of from about 19:1 to about 1:4. In certain embodiments, the weight ratio of the compound of formula (I) or salt or ester thereof to rimsulfuron or salt thereof is within the range of from about 9.7:1 to about 1:2. In certain embodiments, the compositions provided herein comprise the compound of formula (I) or its benzyl ester and rimsulfuron. In one embodiment, the composition comprises the compound of formula (I) and rimsulfuron, wherein the weight ratio of the compound of formula (I) and rimsulfuron is about 9.7:1 to about 1:1.7. In one embodiment, the composition comprises the benzyl ester of the compound of formula (I) and rimsulfuron, wherein the weight ratio of the benzyl ester of the compound of formula (I) and rimsulfuron is about 8:1 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 5 grams active ingredient per hectare (gai/ha) to about 320 gai/ha based on the total amount of active ingredients in the composition. In certain embodiments, the composition is applied at an application rate of from about 7 grams active ingredient per hectare (gai/ha) to about 51 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and rimsulfuron or salt thereof, e.g., sequentially or simultaneously. In some embodiments, the rimsulfuron or salt or ester thereof is applied at a rate from about 3 gai/ha to about 20 gai/ha and the compound of formula (I) of salt or ester thereof is applied at a rate from about 2 gae/ha to about 300 gae/ha. In some embodiments, the rimsulfuron or salt thereof is applied at a rate from about 1 gai/ha to about 20 gai/ha and the compound of formula (I) of salt or ester thereof is applied at a rate from about 2 g acid equivalent per hectare (gae/ha) to about 85 gae/ha. In some embodiments, the rimsulfuron or salt thereof is applied at a rate from about 2.2 gai/ha to about 8.75 gai/ha and the compound of formula (I) of salt or ester thereof is applied at a rate from about 4.38 g acid equivalent per hectare (gae/ha) to about 42 gae/ha. In certain embodiments, the methods utilize the compound of formula (I) or its benzyl ester and rimsulfuron. In one embodiment, the methods utilize the compound of formula (I) and rimsulfuron, wherein the compound of formula (I) is applied at a rate of from about 5.3 g acid equivalent per hectare (gae/ha) to about 43 gae/ha, and the rimsulfuron is applied at a rate of from about 4.4 gai/ha to about 8.8 gai/ha. In one embodiment, the methods utilize the benzyl ester of the compound of formula (I) and rimsulfuron, wherein the benzyl ester of the compound of formula (I) is applied at a rate of from about 4.4 g acid equivalent per hectare (gae/ha) to about 42 gae/ha, and the rimsulfuron is applied at a rate of from about 2.2 gai/ha to about 8.8 gai/ha. In certain embodiments, the methods and compositions utilizing the compound of formula (I) or salt or ester thereof in combination with rimsulfuron or salt thereof are used to control IPOHE, CYPES, DIGSA, LEFCH, CYPRO, and ECHCG.

In certain embodiments of the compositions and methods described herein, the compound of formula (I) or salt or ester thereof is used in combination with sulfometuron-methyl or salt, carboxylic acid, carboxylate salt, or ester thereof. With respect to the compositions, in some embodiments, the weight ratio of the compound of formula (I) or salt or ester thereof to sulfometuron-methyl or salt, carboxylic acid, carboxylate salt, or ester thereof is within the range of from about 1:210 to about 30:1. In certain embodiments, the weight ratio of the compound of formula (I) or salt or ester thereof to sulfometuron-methyl or salt, carboxylic acid, carboxylate salt, or ester thereof is within the range of from 1:50 to about 5:1. In certain embodiments, the compositions provided herein comprise the compound of formula (I) or its benzyl or n-butyl ester and sulfometuron-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (gai/ha) to about 720 gai/ha based on the total amount of active ingredients in the composition. In certain embodiments, the composition is applied at an application rate of from about 52 grams active ingredient per hectare (gai/ha) to about 150 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and sulfometuron-methyl or salt, carboxylic acid, carboxylate salt, or ester thereof, e.g., sequentially or simultaneously. In some embodiments, the sulfometuron-methyl or salt, carboxylic acid, carboxylate salt, or ester thereof is applied at a rate from about 10 gai/ha to about 420 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and sulfometuron-methyl. In some embodiments, the sulfometuron-methyl or salt, carboxylic acid, carboxylate salt, or ester thereof is applied at a rate from about 20 gai/ha to about 100 gai/ha and the compound of formula (I) of salt or ester thereof is applied at a rate from about 2 gae/ha to about 32 gae/ha. In certain embodiments, the methods utilize the compound of formula (I) or its benzyl or n-butyl ester and sulfometuron-methyl. In certain embodiments, the methods and compositions utilizing the compound of formula (I) or salt or ester thereof in combination with sulfometuron-methyl or salt, carboxylic acid, carboxylate salt, or ester thereof are used to control DIGSA.

In certain embodiments of the compositions and methods described herein, the compound of formula (I) or salt or ester thereof is used in combination with sulfosulfuron or salt or ester thereof. In some embodiments, the weight ratio of the compound of formula (I) or salt or ester thereof to sulfosulfuron or salt or ester thereof is within the range of from about 1:35 to about 68:1. In certain embodiments, the weight ratio of the compound of formula (I) or salt or ester thereof to sulfosulfuron or salt or ester thereof is within the range of from 1:11 to about 2:1. The application rate will depend upon the particular type of weed to be controlled, the degree of control required, and the timing and method of application. In some embodiments, the composition is applied at an application rate of from about 6 grams active ingredient per hectare (gai/ha) to about 370 gai/ha based on the total amount of active ingredients in the composition. In certain embodiments, the composition is applied at an application rate of from about 9 grams active ingredient per hectare (gai/ha) to about 100 gai/ha based on the total amount of active ingredients in the composition. In some embodiments, the sulfosulfuron or salt or ester thereof is applied at a rate from about 4 gai/ha to about 70 gai/ha and the compound of formula (I) of salt or ester thereof is applied at a rate from about 2 gae/ha to about 300 gae/ha. In some embodiments, the sulfosulfuron or salt or ester thereof is applied at a rate from about 4 gai/ha to about 20 gai/ha and the compound of formula (I) of salt or ester thereof is applied at a rate from about 4 gae/ha to about 32 gae/ha. In certain embodiments, the methods and compositions utilizing the compound of formula (I) or salt or ester thereof in combination with sulfosulfuron or salt, carboxylic acid, carboxylate salt, or ester thereof are used to control CIRAR, LAMPA, MATCH or VERPE.

In certain embodiments of the compositions and methods described herein, the compound of formula (I) or salt or ester thereof is used in combination with thifensulfuron-methyl or salt, carboxylic acid, carboxylate salt, or ester thereof. With respect to the compositions, in some embodiments, the weight ratio of the compound of formula (I) or salt or ester thereof to thifensulfuron-methyl or salt, carboxylic acid, carboxylate salt, or ester thereof is within the range of from about 1:17 to about 136:1. In certain embodiments, the weight ratio of the compound of formula (I) or salt or ester thereof to thifensulfuron-methyl or salt, carboxylic acid, carboxylate salt, or ester thereof is within the range of from 1:7 to about 4:1. In certain embodiments, the weight ratio of the compound of formula (I) or salt or ester thereof to thifensulfuron-methyl or salt, carboxylic acid, carboxylate salt, or ester thereof is within the range of from about 0.70:1 to about 10:1. In certain embodiments, the weight ratio of the compound of formula (I) or salt or ester thereof to thifensulfuron-methyl or salt, carboxylic acid, carboxylate salt, or ester thereof is within the range of from about 1.5:1 to about 5:1. In certain embodiments, the weight ratio of the compound of formula (I) or salt or ester thereof to thifensulfuron-methyl or salt, carboxylic acid, carboxylate salt, or ester thereof is about 2.3:1. In certain embodiments, the compositions provided herein comprise the benzyl ester of the compound of formula (I) and thifensulfuron-methyl. In one embodiment, the composition comprises the benzyl ester of the compound of formula (I) and thifensulfuron-methyl, wherein the weight ratio of the benzyl ester of the compound of formula (I) to thifensulfuron-methyl is about 2.3:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 335 gai/ha based on the total amount of active ingredients in the composition. In certain embodiments, the composition is applied at an application rate of from about 6 grams active ingredient per hectare (gai/ha) to about 50 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and thifensulfuron-methyl or salt, carboxylic acid, carboxylate salt, or ester thereof, e.g., sequentially or simultaneously. In some embodiments, the thifensulfuron-methyl or salt, carboxylic acid, carboxylate salt, or ester thereof is applied at a rate from about 2.2 gai/ha to about 35 gai/ha and the compound of formula (I) of salt or ester thereof is applied at a rate from about 2 gae/ha to about 300 gae/ha. In some embodiments, the thifensulfuron-methyl or salt, carboxylic acid, carboxylate salt, or ester thereof is applied at a rate from about 1 gai/ha to about 9 gai/ha and the compound of formula (I) of salt or ester thereof is applied at a rate from about 2 g acid equivalent per hectare (gae/ha) to about 20 gae/ha. In some embodiments, the thifensulfuron-methyl or salt, carboxylic acid, carboxylate salt, or ester thereof is applied at a rate from about 3 gai/ha to about 4.5 gai/ha and the compound of formula (I) of salt or ester thereof is applied at a rate from about 7 g acid equivalent per hectare (gae/ha) to about 10 gae/ha. In some embodiments, the thifensulfuron-methyl or salt, carboxylic acid, carboxylate salt, or ester thereof is applied at a rate of about 3.8 gai/ha and the compound of formula (I) of salt or ester thereof is applied at a rate of about 8.75 g acid equivalent per hectare (gae/ha). In certain embodiments, the methods utilize the benzyl ester of the compound of formula (I) and thifensulfuron-methyl. In one embodiment, the methods utilize the benzyl ester of the compound of formula (I) and thifensulfuron-methyl, wherein the benzyl ester of the compound of formula (I) is applied at a rate of about 8.75 gai/ha, and the thifensulfuron-methyl is applied at a rate of about 3.75 gai/ha. In certain embodiments, the methods and compositions utilizing the compound of formula (I) or salt or ester thereof in combination with thifensulfuron-methyl or salt, carboxylic acid, carboxylate salt, or ester thereof are used to control CIRAR.

In certain embodiments of the compositions and methods described herein, the compound of formula (I) or salt or ester thereof is used in combination with triafamone or salt thereof. With respect to the compositions, in some embodiments, the weight ratio of the compound of formula (I) or salt or ester thereof to triafamone or salt thereof is within the range of from about 1:25 to about 60:1. In certain embodiments, the weight ratio of the compound of formula (I) or salt or ester thereof to triafamone or salt thereof is within the range of from 1:23 to about 30:1. In certain embodiments, the compositions provided herein comprise the compound of formula (I)

or its benzyl or n-butyl ester and triafamone. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (gai/ha) to about 350 gai/ha based on the total amount of active ingredients in the composition. In certain embodiments, the composition is applied at an application rate of from about 7 grams active ingredient per hectare (gai/ha) to about 200 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and triafamone or salt thereof, e.g., sequentially or simultaneously In some embodiments, the triafamone or salt or ester thereof is applied at a rate from about 5 gai/ha to about 50 gai/ha and the compound of formula (I) of salt or ester thereof is applied at a rate from about 2 gae/ha to about 300 gae/ha. In certain embodiments, the methods utilize the compound of formula (I) or its n-butyl or benzyl ester and triafamone.

In certain embodiments of the compositions and methods described herein, the compound of formula (I) or salt or ester thereof is used in combination with triasulfuron or salt thereof. With respect to the compositions, in some embodiments, the weight ratio of the compound of formula (I) or salt or ester thereof to triasulfuron or salt thereof is within the range of from about 1:15 to about 136:1. In certain embodiments, the weight ratio of the compound of formula (I) or salt or ester thereof to triasulfuron or salt thereof is within the range of from 1:7 to about 16:1. In certain embodiments, the compositions provided herein comprise the compound of formula (I) or its benzyl or n-butyl ester and triasulfuron. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 330 gai/ha based on the total amount of active ingredients in the composition. In certain embodiments, the composition is applied at an application rate of from about 5 grams active ingredient per hectare (gai/ha) to about 50 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and triasulfuron or salt thereof, e.g., sequentially or simultaneously. In some embodiments, the triasulfuron or salt thereof is applied at a rate from about 2.2 gai/ha to about 30 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and triasulfuron.

In certain embodiments of the compositions and methods described herein, the compound of formula (I) or salt or ester thereof is used in combination with tribenuron-methyl or salt, carboxylic acid, carboxylate salt, or ester thereof. With respect to the compositions, in some embodiments, the weight ratio of the compound of formula (I) or salt or ester thereof to tribenuron-methyl or salt, carboxylic acid, carboxylate salt, or ester thereof is within the range of from about 1:100 to about 100:1. In certain embodiments, the weight ratio of the compound of formula (I) or salt or ester thereof to tribenuron-methyl or salt, carboxylic acid, carboxylate salt, or ester thereof is within the range of from 1:100 to about 100:1. In certain embodiments, the weight ratio of the compound of formula (I) or salt or ester thereof to tribenuron-methyl or salt, carboxylic acid, carboxylate salt, or ester thereof is within the range of from about 1.5:1 to about 10:1. In certain embodiments, the weight ratio of the compound of formula (I) or salt or ester thereof to tribenuron-methyl or salt, carboxylic acid, carboxylate salt, or ester thereof is within the range of from about 3:1 to about 5:1. In certain embodiments, the weight ratio of the compound of formula (I) or salt or ester thereof to tribenuron-methyl or salt, carboxylic acid, carboxylate salt, or ester thereof is about 4:1. In certain embodiments, the compositions provided herein comprise the benzyl ester of the compound of formula (I) and tribenuron-methyl. In one embodiment, the composition comprises the benzyl ester of the compound of formula (I) and tribenuron-methyl, wherein the weight ratio of the benzyl ester of the compound of formula (I) to tribenuron-methyl is about 4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 1000 grams active ingredient per hectare (gai/ha) to about 3000 gai/ha based on the total amount of active ingredients in the composition. In certain embodiments, the composition is applied at an application rate of from about 1000 grams active ingredient per hectare (gai/ha) to about 3000 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tribenuron-methyl or salt, carboxylic acid, carboxylate salt, or ester thereof, e.g., sequentially or simultaneously. In some embodiments, the tribenuron-methyl or salt, carboxylic acid, carboxylate salt, or ester thereof is applied at a rate from about 1000 gai/ha to about 4000 gai/ha and the compound of formula (I) of salt or ester thereof is applied at a rate from about 2 gae/ha to about 300 gae/ha. In some embodiments, the tribenuron-methyl or salt, carboxylic acid, carboxylate salt, or ester thereof is applied at a rate from about 0.50 gai/ha to about 6 gai/ha and the compound of formula (I) of salt or ester thereof is applied at a rate from about 2 g acid equivalent per hectare (gae/ha) to about 20 gae/ha. In some embodiments, the tribenuron-methyl or salt, carboxylic acid, carboxylate salt, or ester thereof is applied at a rate from about 1.5 gai/ha to about 3 gai/ha and the compound of formula (I) of salt or ester thereof is applied at a rate from about 7 g acid equivalent per hectare (gae/ha) to about 10 gae/ha. In some embodiments, the tribenuron-methyl or salt, carboxylic acid, carboxylate salt, or ester thereof is applied at a rate of about 2.2 gai/ha and the compound of formula (I) of salt or ester thereof is applied at a rate of about 8.75 g acid equivalent per hectare (gae/ha). In certain embodiments, the methods utilize the benzyl ester of the compound of formula (I) and tribenuron-methyl. In one embodiment, the methods utilize the benzyl ester of the compound of formula (I) and tribenuron-methyl, wherein the benzyl ester of the compound of formula (I) is applied at a rate of about 8.75 gai/ha, and the tribenuron-methyl is applied at a rate of about 2.2 gai/ha. In certain embodiments, the methods and compositions utilizing the compound of formula (I) or salt or ester thereof in combination with tribenuron-methyl or salt, carboxylic acid, carboxylate salt, or ester thereof are used to control MATCH or CIRAR.

In certain embodiments of the compositions and methods described herein, the compound of formula (I) or salt or ester thereof is used in combination with trifloxysulfuron-sodium or non-ionic form thereof or other trifloxysulfuron salt. With respect to the compositions, in some embodiments, the weight ratio of the compound of formula (I) or salt or ester thereof to trifloxysulfuron-sodium or non-ionic form thereof or other trifloxysulfuron salt is within the range of from about 1:25 to about 600:1. In certain embodiments, the weight ratio of the compound of formula (I) or salt or ester thereof to trifloxysulfuron-sodium or non-ionic form thereof or other trifloxysulfuron salt is within the range of from 1:15 to about 100:1. In certain embodiments, the weight ratio of the compound of formula (I) or salt or ester thereof to trifloxysulfuron-sodium or non-ionic form thereof or other trifloxysulfuron salt is within the range of from 1:3 to about 1:1. In certain embodiments, the compositions provided herein comprise the compound of formula (I) or its benzyl or n-butyl ester and trifloxysulfuron-sodium. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 2.5 grams active ingredient per hectare (gai/ha) to about 350 gai/ha based on the total amount of active ingredients in the composition. In certain embodiments, the composition is applied at an application rate of from about 7 grams active ingredient per hectare (gai/ha) to about 80 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and trifloxysulfuron-sodium or non-ionic form thereof or other trifloxysulfuron salt, e.g., sequentially or simultaneously. In some embodiments, the trifloxysulfuron-sodium or salt or ester thereof is applied at a rate from about 0.5 gai/ha to about 50 gai/ha and the compound of formula (I) of salt or ester thereof is applied at a rate from about 2 gae/ha to about 300 gae/ha. In some embodiments, the trifloxysulfuron-sodium or salt or ester thereof is applied at a rate from about 10 gai/ha to about 30 gai/ha and the compound of formula (I) of salt or ester thereof is applied at a rate from about 8 gae/ha to about 32 gae/ha. In certain embodiments, the methods utilize the compound of formula (I) or benzyl or n-butyl ester thereof and trifloxysulfuron-sodium. In certain embodiments, the methods and compositions utilizing the compound of formula (I) or salt or ester thereof in combination with trifloxysulfuron-sodium or non-ionic form thereof are used to control DIGSA.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, aminocyclopyrachlor, aminopyralid, amiprofos-methyl, amitrole, ammonium sulfamate, anilofos, anisuron, asulam, atraton, atrazine, azafenidin, aziprotryne, barban, BCPC, beflubutamid, benazolin, bencarbazone, benfluralin, benfuresate, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethidimuron, ethiolate, ethobenzamid, etobenzanid, ethofumesate, ethoxyfen, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, florasulam, fluazifop, fluazifop-P-butyl, fluazolate, flucarbazone, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, fluridone, fluorochloridone, fluoroxypyr, fluoroxypyr-meptyl, flurtamone, fluthiacet, fomesafen, fosamine, fumiclorac, furyloxyfen, glufosinate, glufosinate-ammonium, glufosinate-P-ammonium, glyphosate salts and esters, halauxifen, halauxifen-methyl, halosafen, haloxydine, haloxyfop-methyl, haloxyfop-P-methyl, hexachloroacetone, hexaflurate, hexazinone, imazamethabenz, imazamox, imazapic, imazapyr, imazaquin, imazethapyr, indanofan, indaziflam, iodobonil, iodomethane, iodosulfuron-methyl sodium-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, molinate, monalide, monisouron, monochloroacetic acid, monolinuron, monuron, morfamquat, MSMA, naproanilide, napropamide, naptalam, neburon, nipyraclofen, nitralin, nitrofen, nitrofluorfen, norflurazon, noruron, OCH, orbencarb, ortho-dichlorobenzene, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyzamide, prosulfalin, prosulfocarb, proxan, prynachlor, pydanon, pyraclonil, pyraflufen-ethyl, pyrasulfotole, pyrazogyl, pyrazolynate, pyrazoxyfen, pyribenzoxim, pyributicarb, pyriclor, pyridafol, pyridate, pyriftalid, pyriminobac, pyrithiobac-sodium, pyroxasulfone, pyroxsulam, quinclorac, quinmerac, quinoclamine, quinonamid, quizalofop, quizalofop-P-ethyl, rhodethanil, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfosate, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfurnmethyl, thiobencarb, tiocarbazil, tioclorim, topramezone, tralkoxydim, tri-allate, triaziflam, tricamba, triclopyr choline salt, triclopyr esters and salts, tridiphane, trietazine, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, turf, tree and vine orchards, plantation crops, vegetables, and non-crop (ornamentals) settings. In some embodiments, the plant growth regulator is mixed with the compound of formula (I), or mixed with the compound of formula (I) and a sulfonylurea to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments from about 0.5 to 90 weight percent. Such compositions are, in certain embodiments, diluted with an inert carrier, such as water, before application. The diluted compositions usually applied to weeds or the locus of weeds contain, in certain embodiments, about 0.0003 to 65.0 weight percent active ingredient and in certain embodiments contain about 0.0008 to 32.5 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, IV, and V are greenhouse trial results.

Example I

Evaluation of Postemergence Foliar-Applied Herbicidal Mixtures for Weed Control in Direct Seeded Rice

Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC, and various herbicidal components alone and in combination. Forms of compound A were applied on an acid equivalent basis.

Forms of compound A (compound of formula I) tested include:

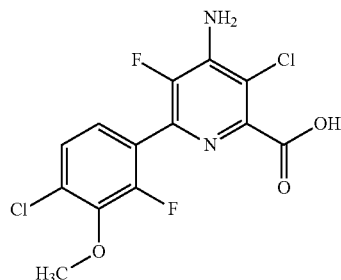

Compound A Acid

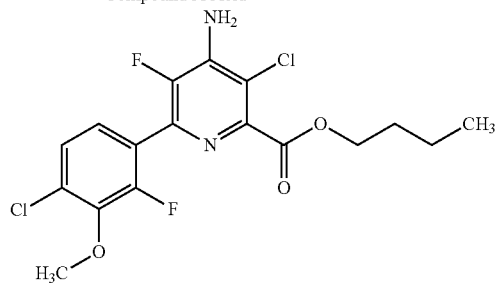

Compound A n-Butyl Ester

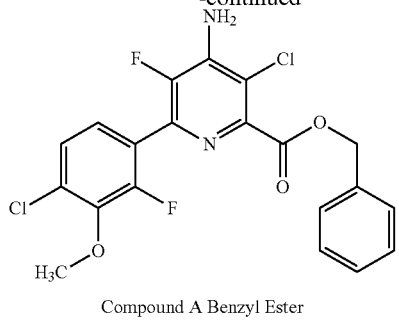

Compound A Benzyl Ester

Other herbicidal components were applied on an active ingredient basis and included acetolactate synthase (ALS)-inhibiting herbicides (sulfonylurea chemical class) azimsulfuron formulated as Gulliver®, bensulfuron-methyl formulated as Londax® 60DF, cyclosulfamuron (technical material), ethoxysulfuron formulated as Sunrice® 15 WDG, flazasulfuron formulated as Katana®, flucetosulfuron formulated as Sukedachi® 1KG G, foramsulfuron formulated as Option®, imazosulfuron formulated as Brazzos® WG, iodosulfuron-methyl-sodium formulated as Hussar®, metsulfuron-methyl formulated as Lorate®, nicosulfuron formulated as Accent®, orthosulfamuron formulated as Strada® WG, primisulfuron-methyl (technical material), propyrisulfuron formulated as Zeta One®, rimsulfuron formulated as Matrix® WG, sulfometuron-methyl formulated as Oust®, and trifloxysulfuron-sodium formulated as Monument® 75WG.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) Agrcrop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.25% (v/v) crop oil concentrate to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. When required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with an 8002E nozzle calibrated to deliver 187 L/ha over an application area of 0.503 $m^2$ at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-27.

TABLE 1

Synergistic Activity of Foliar-Applied Compound A Acid and Azimsulfuron Herbicidal Compositions on Weed Control in a Rice Cropping System.

| Compound A Acid | Azimsulfuron | Visual Weed Control (%) - 20 DAA BRAPP | |
|---|---|---|---|
| gae/ha | gai/ha | Obs | Exp |
| 4.38 | 0 | 10 | — |
| 0 | 3.125 | 0 | — |
| 0 | 6.25 | 0 | — |
| 0 | 12.5 | 60 | — |
| 4.38 | 3.125 | 20 | 10 |
| 4.38 | 6.25 | 70 | 10 |
| 4.38 | 12.5 | 75 | 64 |

TABLE 2

Synergistic Activity of Foliar-Applied Compound A Benzyl Ester and Azimsulfuron Herbicidal Compositions on Weed Control in a Rice Cropping System.

| Compound A Benzyl Ester | Azimsulfuron | Visual Weed Control (%) - 20 DAA LEFCH | |
|---|---|---|---|
| gae/ha | gai/ha | Obs | Exp |
| 4.38 | 0 | 10 | — |
| 8.75 | 0 | 20 | — |
| 0 | 3.125 | 0 | — |
| 0 | 6.25 | 0 | — |
| 4.38 | 3.125 | 10 | 10 |
| 8.75 | 3.125 | 45 | 20 |
| 4.38 | 6.25 | 20 | 10 |
| 8.75 | 6.25 | 35 | 20 |

TABLE 3

Synergistic Activity of Foliar-Applied Compound A Acid and Bensulfuron-methyl Herbicidal Compositions on Weed Control in a Rice Cropping System.

| Compound A Acid gae/ha | Bensulfuron-methyl gai/ha | Obs | Exp |
|---|---|---|---|
| | | Visual Weed Control (%) - 21 DAA BRAPP | |
| 4.38 | 0 | 40 | — |
| 0 | 4.38 | 0 | — |
| 0 | 8.75 | 0 | — |
| 0 | 17.5 | 0 | — |
| 4.38 | 4.38 | 55 | 40 |
| 4.38 | 8.75 | 50 | 40 |
| 4.38 | 17.5 | 60 | 40 |
| 4.38 | 0 | 50 | — |
| 0 | 17.5 | 0 | — |
| 0 | 35 | 0 | — |
| 4.38 | 17.5 | 65 | 50 |
| 4.38 | 35 | 55 | 50 |
| | | Visual Weed Control (%) - 21 DAA ECHCG | |
| 4.38 | 0 | 15 | — |
| 8.75 | 0 | 50 | — |
| 0 | 17.5 | 0 | — |
| 0 | 35 | 0 | — |
| 4.38 | 17.5 | 40 | 15 |
| 8.75 | 17.5 | 70 | 50 |
| 4.38 | 35 | 40 | 15 |
| 8.75 | 35 | 65 | 50 |
| | | Visual Weed Control (%) - 20 DAA LEFCH | |
| 19.4 | 0 | 5 | — |
| 0 | 70 | 5 | — |
| 19.4 | 70 | 35 | 10 |

TABLE 4

Synergistic Activity of Foliar-Applied Compound A Benzyl Ester and Bensulfuron-methyl Herbicidal Compositions on Weed Control in a Rice Cropping System.

| Compound A Benzyl Ester gae/ha | Bensulfuron-methyl gai/ha | Visual Weed Control (%) - 21 DAA BRAPP | |
|---|---|---|---|
| | | Obs | Exp |
| 8.75 | 0 | 70 | — |
| 17.5 | 0 | 80 | — |
| 0 | 8.75 | 0 | — |
| 0 | 17.5 | 0 | — |
| 8.75 | 8.75 | 80 | 70 |
| 17.5 | 8.75 | 95 | 80 |
| 8.75 | 17.5 | 85 | 70 |
| 17.5 | 17.5 | 90 | 80 |
| 4.38 | 0 | 50 | — |
| 8.75 | 0 | 80 | — |
| 0 | 17.5 | 0 | — |
| 0 | 35 | 0 | — |
| 4.38 | 17.5 | 75 | 50 |
| 8.75 | 17.5 | 95 | 80 |
| 4.38 | 35 | 75 | 50 |
| 8.75 | 35 | 95 | 80 |

| Compound A Benzyl Ester gae/ha | Bensulfuron-methyl gai/ha | Visual Weed Control (%) - 21 DAA | | | |
|---|---|---|---|---|---|
| | | ECHCG | | LEFCH | |
| | | Obs | Exp | Obs | Exp |
| 4.38 | 0 | 10 | — | 0 | — |
| 0 | 17.5 | 0 | — | 10 | — |
| 0 | 35 | 0 | — | 10 | — |
| 4.38 | 17.5 | 35 | 10 | 20 | 10 |
| 4.38 | 35 | 30 | 10 | 60 | 10 |

| Compound A Benzyl Ester gae/ha | Bensulfuron-methyl gai/ha | Visual Weed Control (%) - 20 DAA ISCRU | |
|---|---|---|---|
| | | Obs | Exp |
| 6 | 0 | 30 | — |
| 24 | 0 | 35 | — |
| 0 | 70 | 30 | — |
| 6 | 70 | 70 | 51 |
| 24 | 70 | 100 | 55 |

TABLE 5

Synergistic Activity of Foliar-Applied Compound A n-Butyl Ester and Bensulfuron-methyl Herbicidal Compositions on Weed Control in a Rice Cropping System.

| Compound A n-Butyl Ester gae/ha | Bensulfuron-methyl gai/ha | Visual Weed Control (%) - 21 DAA BRAPP | |
|---|---|---|---|
| | | Obs | Exp |
| 4.38 | 0 | 0 | — |
| 8.75 | 0 | 40 | — |
| 0 | 4.38 | 0 | — |
| 0 | 8.75 | 0 | — |
| 0 | 17.5 | 0 | — |
| 4.38 | 4.38 | 40 | 0 |
| 8.75 | 4.38 | 55 | 40 |
| 4.38 | 8.75 | 20 | 0 |
| 8.75 | 8.75 | 50 | 40 |
| 4.38 | 17.5 | 50 | 0 |
| 8.75 | 17.5 | 30 | 40 |

| Compound A n-Butyl Ester gae/ha | Bensulfuron-methyl gai/ha | Visual Weed Control (%) - 27 DAA ECHCG | |
|---|---|---|---|
| | | Obs | Exp |
| 4.38 | 0 | 0 | — |
| 8.75 | 0 | 0 | — |
| 0 | 4.38 | 0 | — |
| 0 | 8.75 | 0 | — |
| 0 | 17.5 | 0 | — |
| 4.38 | 4.38 | 10 | 0 |
| 8.75 | 4.38 | 20 | 0 |
| 4.38 | 8.75 | 20 | 0 |
| 8.75 | 8.75 | 10 | 0 |
| 4.38 | 17.5 | 10 | 0 |
| 8.75 | 17.5 | 20 | 0 |

TABLE 6

Synergistic Activity of Foliar-Applied Compound A Benzyl Ester and Cyclosulfamuron Herbicidal Compositions on Weed Control in a Rice Cropping System.

| Compound A Benzyl Ester gae/ha | Cyclosulfamuron gai/ha | Visual Weed Control (%) - 22 DAA CYPIR | |
|---|---|---|---|
| | | Obs | Exp |
| 8 | 0 | 10 | — |
| 16 | 0 | 60 | — |
| 0 | 12.5 | 95 | — |
| 8 | 12.5 | 100 | 96 |
| 16 | 12.5 | 100 | 98 |

TABLE 7

Synergistic Activity of Foliar-Applied Compound A Acid and Ethoxysulfuron Herbicidal Compositions on Weed Control in a Rice Cropping System.

| Compound A Acid gae/ha | Ethoxysulfuron gai/ha | Visual Weed Control (%) - 22 DAA CYPIR | |
|---|---|---|---|
| | | Obs | Exp |
| 8 | 0 | 60 | — |
| 16 | 0 | 90 | — |
| 0 | 7.5 | 50 | — |

TABLE 7-continued

Synergistic Activity of Foliar-Applied Compound A Acid and Ethoxysulfuron Herbicidal Compositions on Weed Control in a Rice Cropping System.

| Compound A Acid gae/ha | Ethoxysulfuron gai/ha | Visual Weed Control (%) - 22 DAA CYPIR Obs | Exp |
|---|---|---|---|
| 0 | 15 | 50 | — |
| 8 | 7.5 | 95 | 80 |
| 16 | 7.5 | 85 | 95 |
| 8 | 15 | 99 | 80 |
| 16 | 15 | 100 | 95 |

TABLE 8

Synergistic Activity of Foliar-Applied Compound A Benzyl Ester and Ethoxysulfuron Herbicidal Compositions on Weed Control in a Rice Cropping System.

| Compound A Benzyl Ester gae/ha | Ethoxysulfuron gai/ha | Obs | Exp |
|---|---|---|---|
| | | Visual Weed Control (%) - 22 DAA BRAPP | |
| 8 | 0 | 50 | — |
| 0 | 7.5 | 0 | — |
| 0 | 15 | 0 | — |
| 0 | 30 | 0 | — |
| 8 | 7.5 | 75 | 50 |
| 8 | 15 | 65 | 50 |
| 8 | 30 | 80 | 50 |
| | | Visual Weed Control (%) - 22 DAA CYPIR | |
| 8 | 0 | 60 | — |
| 16 | 0 | 80 | — |
| 0 | 7.5 | 50 | — |
| 0 | 15 | 50 | — |
| 0 | 30 | 85 | — |
| 8 | 7.5 | 95 | 80 |
| 16 | 7.5 | 85 | 90 |
| 8 | 15 | 99 | 80 |
| 16 | 15 | 100 | 90 |
| 8 | 30 | 99 | 94 |
| 16 | 30 | 100 | 97 |
| | | Visual Weed Control (%) - 21 DAA ISCRU | |
| 8 | 0 | 20 | — |
| 16 | 0 | 0 | — |
| 0 | 17.5 | 0 | — |
| 0 | 70 | 0 | — |
| 8 | 17.5 | 15 | 20 |
| 16 | 17.5 | 25 | 0 |
| 8 | 70 | 100 | 20 |
| 16 | 70 | 100 | 0 |

TABLE 9

Synergistic Activity of Foliar-Applied Compound A Acid and Flazasulfuron Herbicidal Compositions on Weed Control in a Rice Cropping System.

| Compound A Acid gae/ha | Flazasulfuron gai/ha | Visual Weed Control (%) - 22 DAA IPOHE Obs | Exp |
|---|---|---|---|
| 8 | 0 | 25 | — |
| 16 | 0 | 35 | — |
| 32 | 0 | 40 | — |
| 0 | 100 | 50 | — |
| 8 | 100 | 75 | 63 |
| 16 | 100 | 80 | 68 |
| 32 | 100 | 75 | 70 |

TABLE 10

Synergistic Activity of Foliar-Applied Compound A Benzyl Ester and Flazasulfuron Herbicidal Compositions on Weed Control in a Rice Cropping System.

| Compound A Benzyl Ester gae/ha | Flazasulfuron gai/ha | Visual Weed Control 22% - 22 DAA Obs | Exp |
|---|---|---|---|
| | | LEFCH | |
| 8 | 0 | 0 | — |
| 0 | 25 | 0 | — |
| 0 | 50 | 10 | — |
| 8 | 25 | 20 | 0 |
| 8 | 50 | 35 | 10 |
| | | IPOHE | |
| 8 | 0 | 10 | — |
| 16 | 0 | 10 | — |
| 32 | 0 | 35 | — |
| 0 | 50 | 50 | — |
| 0 | 100 | 50 | — |
| 8 | 50 | 65 | 55 |
| 16 | 50 | 65 | 55 |
| 32 | 50 | 70 | 68 |
| 8 | 100 | 65 | 55 |
| 16 | 100 | 85 | 55 |
| 32 | 100 | 70 | 68 |

TABLE 11

Synergistic Activity of Foliar-Applied Compound A Acid and Flucetosulfuron Herbicidal Compositions on Weed Control in a Rice Cropping System.

| Compound A Acid gae/ha | Flucetosulfuron gai/ha | Obs | Exp |
|---|---|---|---|
| | | Visual Weed Control (%) - 21 DAA LEFCH | |
| 8.75 | 0 | 40 | — |
| 17.5 | 0 | 30 | — |
| 0 | 0.05 | 0 | — |
| 0 | 0.1 | 0 | — |
| 8.75 | 0.05 | 55 | 40 |

TABLE 11-continued

Synergistic Activity of Foliar-Applied Compound A Acid and Flucetosulfuron Herbicidal Compositions on Weed Control in a Rice Cropping System.

| Compound A Acid gae/ha | Flucetosulfuron gai/ha | Obs | Exp |
|---|---|---|---|
| 17.5 | 0.05 | 40 | 30 |
| 8.75 | 0.1 | 35 | 40 |
| 17.5 | 0.1 | 60 | 30 |

Visual Weed Control (%) - 21 DAA IPOHE

| Compound A Acid gae/ha | Flucetosulfuron gai/ha | Obs | Exp |
|---|---|---|---|
| 4.38 | 0 | 25 | — |
| 8.75 | 0 | 30 | — |
| 17.5 | 0 | 45 | — |
| 0 | 0.2 | 20 | — |
| 4.38 | 0.2 | 50 | 40 |
| 8.75 | 0.2 | 65 | 44 |
| 17.5 | 0.2 | 65 | 56 |

Visual Weed Control (%) - 21 DAA CYPIR

| Compound A Acid gae/ha | Flucetosulfuron gai/ha | Obs | Exp |
|---|---|---|---|
| 4.38 | 0 | 70 | — |
| 0 | 0.05 | 0 | — |
| 0 | 0.1 | 0 | — |
| 0 | 0.2 | 20 | — |
| 4.38 | 0.05 | 95 | 70 |
| 4.38 | 0.1 | 95 | 70 |
| 4.38 | 0.2 | 95 | 76 |

Visual Weed Control (%) - 22 DAA IPOHE

| Compound A Acid gae/ha | Flucetosulfuron gai/ha | Obs | Exp |
|---|---|---|---|
| 8 | 0 | 25 | — |
| 16 | 0 | 35 | — |
| 0 | 5 | 90 | — |
| 0 | 10 | 90 | — |
| 8 | 5 | 95 | 93 |
| 16 | 5 | 95 | 94 |
| 8 | 10 | 95 | 93 |
| 16 | 10 | 99 | 94 |

TABLE 12

Synergistic Activity of Foliar-Applied Compound A Benzyl Ester and Flucetosulfuron Herbicidal Compositions on Weed Control in a Rice Cropping System.

| Compound A Benzyl Ester gae/ha | Flucetosulfuron gai/ha | Visual Weed Control (%) - 21 DAA IPOHE Obs | Exp |
|---|---|---|---|
| 4.38 | 0 | 0 | — |
| 8.75 | 0 | 10 | — |
| 17.5 | 0 | 30 | — |
| 0 | 0.05 | 20 | — |
| 4.38 | 0.05 | 60 | 20 |
| 8.75 | 0.05 | 60 | 28 |
| 17.5 | 0.05 | 45 | 44 |

TABLE 12-continued

Synergistic Activity of Foliar-Applied Compound A Benzyl Ester and Flucetosulfuron Herbicidal Compositions on Weed Control in a Rice Cropping System.

| Compound A Benzyl Ester gae/ha | Fluceto-sulfuron gai/ha | BRAPP Obs | BRAPP Exp | CYPIR Obs | CYPIR Exp | SCPJU Obs | SCPJU Exp |
|---|---|---|---|---|---|---|---|
| 4.38 | 0 | 50 | — | 50 | — | 40 | — |
| 0 | 0.05 | 0 | — | 0 | — | 95 | — |
| 0 | 0.1 | 0 | — | 0 | — | 50 | — |
| 0 | 0.2 | 0 | — | 20 | — | 30 | — |
| 4.38 | 0.5 | 65 | 50 | 90 | 50 | 100 | 97 |
| 4.38 | 0.1 | 70 | 50 | 100 | 50 | 99 | 70 |
| 4.38 | 0.2 | 75 | 50 | 99 | 60 | 100 | 58 |

| Compound A Benzyl Ester gae/ha | Flucetosulfuron gai/ha | Visual Weed Control (%) - 22 DAA LEFCH Obs | Exp |
|---|---|---|---|
| 8 | 0 | 0 | — |
| 16 | 0 | 20 | — |
| 32 | 0 | 15 | — |
| 0 | 1.7 | 0 | — |
| 0 | 5 | 0 | — |
| 8 | 1.7 | 20 | 0 |
| 16 | 1.7 | 10 | 20 |
| 32 | 1.7 | 10 | 15 |
| 8 | 5 | 0 | 0 |
| 16 | 5 | 20 | 20 |
| 32 | 5 | 30 | 15 |

| Compound A Benzyl Ester gae/ha | Flucetosulfuron gai/ha | Visual Weed Control (%) - 22 DAA BRAPP Obs | Exp |
|---|---|---|---|
| 8 | 0 | 50 | — |
| 16 | 0 | 90 | — |
| 32 | 0 | 85 | — |
| 0 | 1.7 | 0 | — |
| 8 | 1.7 | 75 | 50 |
| 16 | 1.7 | 85 | 90 |
| 32 | 1.7 | 85 | 85 |

TABLE 13

Synergistic Activity of Foliar-Applied Compound A Benzyl Ester and Foramsulfuron Herbicidal Compositions for Control of Weeds Common to Rice.

| Compound A Benzyl Ester gae/ha | Foramsulfuron gai/ha | Visual Weed Control (%) - 21 DAA LEFCH Obs | Exp |
|---|---|---|---|
| 8 | 0 | 20 | — |
| 0 | 20 | 0 | — |
| 0 | 40 | 25 | — |
| 8 | 20 | 30 | 20 |
| 8 | 40 | 45 | 40 |

TABLE 14

Synergistic Activity of Foliar-Applied Compound A Acid and Imazosulfuron Herbicidal Compositions on Weed Control in a Rice Cropping System.

| Compound A Acid | Imazosulfuron | Visual Weed Control (%) - 24 DAA DIGSA | |
|---|---|---|---|
| gae/ha | gai/ha | Obs | Exp |
| 17.5 | 0 | 25 | — |
| 0 | 21 | 0 | — |
| 0 | 42 | 0 | — |
| 17.5 | 21 | 40 | 25 |
| 17.5 | 42 | 50 | 25 |

TABLE 15

Synergistic Activity of Foliar-Applied Compound A Benzyl Ester and Imazosulfuron Herbicidal Compositions on Weed Control in a Rice Cropping System.

| Compound A Benzyl Ester | Imazosulfuron | Visual Weed Control (%) - 24 DAA LEFCH | |
|---|---|---|---|
| gae/ha | gai/ha | Obs | Exp |
| 8.75 | 0 | 0 | — |
| 17.5 | 0 | 10 | — |
| 0 | 21 | 0 | — |
| 0 | 42 | 0 | — |
| 0 | 84 | 0 | — |
| 8.75 | 21 | 15 | 0 |
| 17.5 | 21 | 25 | 10 |
| 8.75 | 42 | 10 | 0 |
| 17.5 | 42 | 25 | 10 |
| 8.75 | 84 | 10 | 0 |
| 17.5 | 84 | 25 | 10 |

TABLE 16

Synergistic Activity of Foliar-Applied Compound A Benzyl Ester and Iodosulfuron-Methyl-Sodium Herbicidal Compositions on Weed Control in a Rice Cropping System.

| Compound A Benzyl Ester | Iodosulfuron-methyl sodium | Visual Weed Control (%) - 21 DAA IPOHE | |
|---|---|---|---|
| gae/ha | gai/ha | Obs | Exp |
| 8 | 0 | 10 | — |
| 16 | 0 | 10 | — |
| 32 | 0 | 45 | — |
| 0 | 2.5 | 90 | — |
| 0 | 5 | 95 | — |
| 8 | 2.5 | 95 | 91 |
| 16 | 2.5 | 95 | 91 |
| 32 | 2.5 | 95 | 95 |
| 8 | 5 | 95 | 96 |
| 16 | 5 | 99 | 96 |
| 32 | 5 | 99 | 97 |

TABLE 17

Synergistic Activity of Foliar-Applied Compound A Benzyl Ester and Metsulfuronmethyl Herbicidal Compositions on Weed Control in a Rice Cropping System.

| Compound A Benzyl Ester | Metsulfuron-methyl | Visual Weed Control (%) - 20 DAA BRAPP | |
|---|---|---|---|
| gae/ha | gai/ha | Obs | Exp |
| 4.38 | 0 | 60 | — |
| 8.75 | 0 | 75 | — |
| 17.5 | 0 | 85 | — |
| 0 | 7.5 | 0 | — |
| 0 | 15 | 20 | — |
| 4.38 | 7.5 | 90 | 60 |
| 8.75 | 7.5 | 90 | 75 |
| 17.5 | 7.5 | 90 | 85 |
| 4.38 | 15 | 95 | 68 |
| 8.75 | 15 | 95 | 80 |
| 17.5 | 15 | 95 | 88 |

TABLE 18

Synergistic Activity of Foliar-Applied Compound A Acid and Nicosulfuron Herbicidal Compositions on Control of Weeds Common to Rice Cropping Systems.

| Compound A Acid | Nicosulfuron | Visual Weed Control (%) - 20 DAA | |
|---|---|---|---|
| gae/ha | gai/ha | Obs | Exp |
| | | DIGSA | |
| 5.3 | 0 | 10 | — |
| 0 | 8.75 | 30 | — |
| 0 | 17.5 | 55 | — |
| 5.3 | 8.75 | 50 | 37 |
| 5.3 | 17.5 | 85 | 60 |
| | | LEFCH | |
| 5.3 | 0 | 0 | — |
| 10.6 | 0 | 10 | — |
| 21.2 | 0 | 15 | — |
| 0 | 35 | 75 | — |
| 5.3 | 35 | 95 | 75 |
| 10.6 | 35 | 70 | 78 |
| 21.2 | 35 | 95 | 79 |
| | | CYPES | |
| 5.3 | 0 | 0 | — |
| 0 | 8.75 | 10 | — |
| 0 | 17.5 | 60 | — |
| 0 | 35 | 70 | — |
| 5.3 | 8.75 | 85 | 10 |
| 5.3 | 17.5 | 85 | 60 |
| 5.3 | 35 | 90 | 70 |

TABLE 19

Synergistic Activity of Foliar-Applied Compound A Benzyl Ester and Nicosulfuron Herbicidal Compositions on Control of Weeds Common to Rice Cropping Systems.

| Compound A Benzyl Ester | Nicosulfuron | Visual Weed Control (%) - 20 DAA CYPIR | |
|---|---|---|---|
| gae/ha | gai/ha | Obs | Exp |
| 4.38 | 0 | 15 | — |
| 8.75 | 0 | 60 | — |
| 17.5 | 0 | 90 | — |
| 0 | 8.75 | 80 | — |

TABLE 19-continued

Synergistic Activity of Foliar-Applied Compound A Benzyl Ester and Nicosulfuron Herbicidal Compositions on Control of Weeds Common to Rice Cropping Systems.

| Compound A Benzyl Ester | Nicosulfuron | Visual Weed Control (%) - 20 DAA CYPIR | |
|---|---|---|---|
| gae/ha | gai/ha | Obs | Exp |
| 4.38 | 8.75 | 100 | 83 |
| 8.75 | 8.75 | 95 | 92 |
| 17.5 | 8.75 | 100 | 98 |

TABLE 20

Synergistic Activity of Foliar-Applied Compound A Acid and Orthosulfamuron Herbicidal Compositions on Weed Control in a Rice Cropping System.

| Compound A Acid | Orthosulfamuron | Visual Weed Control (%) - 20 DAA | |
|---|---|---|---|
| gae/ha | gai/ha | Obs | Exp |
| | | LEFCH | |
| 4.38 | 0 | 0 | — |
| 8.75 | 0 | 0 | — |
| 17.5 | 0 | 10 | — |
| 0 | 7.5 | 0 | — |
| 0 | 15 | 0 | — |
| 4.38 | 7.5 | 25 | 0 |
| 8.75 | 7.5 | 20 | 0 |
| 17.5 | 7.5 | 25 | 10 |
| 4.38 | 15 | 15 | 0 |
| 8.75 | 15 | 10 | 0 |
| 17.5 | 15 | 20 | 10 |
| | | CYPES | |
| 4.38 | 0 | 30 | — |
| 8.75 | 0 | 70 | — |
| 0 | 7.5 | 0 | — |
| 0 | 15 | 30 | — |
| 4.38 | 7.5 | 85 | 30 |
| 8.75 | 7.5 | 95 | 70 |
| 4.38 | 15 | 60 | 51 |
| 8.75 | 15 | 95 | 79 |

TABLE 21

Synergistic Activity of Foliar-Applied Compound A Benzyl Ester and Orthosulfamuron Herbicidal Compositions on Weed Control in a Rice Cropping System.

| Compound A Benzyl Ester | Orthosulfamuron | Visual Weed Control (%) - 20 DAA LEFCH | |
|---|---|---|---|
| gae/ha | gai/ha | Obs | Exp |
| 4.38 | 0 | 0 | — |
| 8.75 | 0 | 20 | — |
| 17.5 | 0 | 40 | — |
| 0 | 7.5 | 0 | — |
| 0 | 15 | 0 | — |
| 4.38 | 7.5 | 30 | 0 |
| 8.75 | 7.5 | 25 | 20 |
| 17.5 | 7.5 | 45 | 40 |
| 4.38 | 15 | 20 | 0 |
| 8.75 | 15 | 30 | 20 |
| 17.5 | 15 | 55 | 40 |

TABLE 21-continued

Synergistic Activity of Foliar-Applied Compound A Benzyl Ester and Orthosulfamuron Herbicidal Compositions on Weed Control in a Rice Cropping System.

| Compound A Benzyl Ester | Orthosulfamuron | Visual Weed Control (%) - 20 DAA | | | |
|---|---|---|---|---|---|
| | | BRAPP | | CYPES | |
| gae/ha | gai/ha | Obs | Exp | Obs | Exp |
| 4.38 | 0 | 40 | — | 70 | — |
| 8.75 | 0 | 70 | — | 80 | — |
| 0 | 7.5 | 0 | — | 0 | — |
| 0 | 15 | 30 | — | 30 | — |
| 4.38 | 7.5 | 60 | 40 | 90 | 70 |
| 8.75 | 7.5 | 85 | 70 | 100 | 80 |
| 4.38 | 15 | 70 | 58 | 90 | 79 |
| 8.75 | 15 | 70 | 79 | 90 | 86 |

| Compound A Benzyl Ester | Orthosulfamuron | Visual Weed Control (%) - 20 DAA CYPIR | |
|---|---|---|---|
| gae/ha | gai/ha | Obs | Exp |
| 4.38 | 0 | 15 | — |
| 0 | 7.5 | 50 | — |
| 0 | 15 | 75 | — |
| 0 | 30 | 65 | — |
| 4.38 | 7.5 | 95 | 58 |
| 4.38 | 15 | 95 | 79 |
| 4.38 | 30 | 95 | 70 |

TABLE 22

Synergistic Activity of Foliar-Applied Compound A Benzyl Ester and Primisulfuron-methyl Herbicidal Compositions on Weed Control in a Rice Cropping System

| Compound A Benzyl Ester | Primisulfuron-methyl | Visual Weed Control (%) - 21 DAA LEFCH | |
|---|---|---|---|
| gae/ha | gai/ha | Obs | Exp |
| 8 | 0 | 25 | — |
| 0 | 15 | 40 | — |
| 0 | 30 | 60 | — |
| 8 | 15 | 70 | 55 |
| 8 | 30 | 75 | 70 |

TABLE 23

Synergistic Activity of Foliar-Applied Compound A Benzyl Ester and Propyrisulfuron Herbicidal Compositions on Weed Control in a Rice Cropping System

| Compound A Benzyl Ester | Propyrisulfuron | Visual Weed Control (%) - 21 DAA BRAPP | |
|---|---|---|---|
| gae/ha | gai/ha | Obs | Exp |
| 4.38 | 0 | 50 | — |
| 0 | 11.25 | 0 | — |
| 0 | 22.5 | 20 | — |
| 0 | 45 | 10 | — |
| 4.38 | 11.25 | 70 | 50 |
| 4.38 | 22.5 | 70 | 60 |
| 4.38 | 45 | 70 | 55 |

TABLE 24

Synergistic Activity of Foliar-Applied Compound A Acid and Rimsulfuron Herbicidal Compositions on Control of Weeds Common to Rice Cropping Systems.

| Compound A Acid | Rimsulfuron | Visual Weed Control (%) - 20 DAA | |
|---|---|---|---|
| gae/ha | gai/ha | Obs | Exp |
| IPOHE | | | |
| 5.3 | 0 | 0 | — |
| 10.6 | 0 | 15 | — |
| 21.2 | 0 | 25 | — |
| 0 | 4.38 | 60 | — |
| 0 | 8.75 | 75 | — |
| 5.3 | 4.38 | 80 | 60 |
| 10.6 | 4.38 | 85 | 66 |
| 21.2 | 4.38 | 85 | 70 |
| 5.3 | 8.75 | 90 | 75 |
| 10.6 | 8.75 | 85 | 79 |
| 21.2 | 8.75 | 90 | 81 |
| CYPES | | | |
| 5.3 | 0 | 0 | — |
| 0 | 2.19 | 0 | — |
| 0 | 4.38 | 0 | — |
| 0 | 8.75 | 60 | — |
| 5.3 | 2.19 | 30 | 0 |
| 5.3 | 4.38 | 90 | 0 |
| 5.3 | 8.75 | 85 | 60 |

TABLE 25

Synergistic Activity of Foliar-Applied Compound A Benzyl Ester and Rimsulfuron Herbicidal Compositions on Control of Weeds Common to Rice Cropping Systems.

| Compound A Benzyl Ester | Rimsulfuron | Visual Weed Control (%) - 20 DAA | |
|---|---|---|---|
| gae/ha | gai/ha | Obs | Exp |
| DIGSA | | | |
| 4.38 | 0 | 20 | — |
| 8.75 | 0 | 15 | — |
| 17.5 | 0 | 20 | — |
| 0 | 8.75 | 70 | — |
| 4.38 | 8.75 | 90 | 76 |
| 8.75 | 8.75 | 65 | 75 |
| 17.5 | 8.75 | 90 | 76 |
| IPOHE | | | |
| 4.38 | 0 | 10 | — |
| 8.75 | 0 | 10 | — |
| 17.5 | 0 | 25 | — |
| 0 | 4.38 | 60 | — |
| 0 | 8.75 | 75 | — |
| 4.38 | 4.38 | 80 | 64 |
| 8.75 | 4.38 | 95 | 64 |
| 17.5 | 4.38 | 85 | 70 |
| 4.38 | 8.75 | 100 | 78 |
| 8.75 | 8.75 | 75 | 78 |
| 17.5 | 8.75 | 99 | 81 |
| CYPES | | | |
| 4.38 | 0 | 85 | — |
| 8.75 | 0 | 90 | — |
| 17.5 | 0 | 90 | — |
| 0 | 2.19 | 0 | — |
| 0 | 4.38 | 0 | — |
| 4.38 | 2.19 | 95 | 85 |
| 8.75 | 2.19 | 95 | 90 |
| 17.5 | 2.19 | 85 | 90 |
| 4.38 | 4.38 | 100 | 85 |
| 8.75 | 4.38 | 100 | 90 |
| 17.5 | 4.38 | 100 | 90 |

TABLE 26

Synergistic Activity of Foliar-Applied Compound A Benzyl Ester and Sulfometuron-methyl Herbicidal Compositions on Control of Weeds Common to Rice Cropping Systems.

| Compound A Benzyl Ester | Sulfometuron-methyl | Visual Weed Control (%) - 22 DAA DIGSA | |
|---|---|---|---|
| gae/ha | gai/ha | Obs | Exp |
| 8 | 0 | 20 | — |
| 16 | 0 | 20 | — |
| 32 | 0 | 35 | — |
| 0 | 35 | 85 | — |
| 8 | 35 | 95 | 88 |
| 16 | 35 | 100 | 88 |
| 32 | 35 | 90 | 90 |

TABLE 27

Synergistic Activity of Foliar-Applied Compound A Benzyl Ester and Trifloxysulfuron-sodium Herbicidal Compositions on Control of Weeds Common to Rice Cropping Systems.

| Compound A Benzyl Ester | Trifloxysulfuron-sodium | Visual Weed Control (%) - 21 DAA DIGSA | |
|---|---|---|---|
| gae/ha | gai/ha | Obs | Exp |
| 8 | 0 | 25 | — |
| 16 | 0 | 30 | — |
| 32 | 0 | 50 | — |
| 0 | 24 | 65 | — |
| 8 | 24 | 85 | 74 |
| 16 | 24 | 99 | 76 |
| 32 | 24 | 95 | 83 |

| | | |
|---|---|---|
| BRAPP | *Brachiaria platyphylla* (Griseb.) Nash | signalgrass, broadleaf |
| CYPDI | *Cyperus difformis* L. | sedge, smallflower umbrella |
| CYPES | *Cyperus esculentus* L. | nutsedge, yellow |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| ISCRU | *Ischaemum rugosum* Salisb. | saramollagrass |
| LEFCH | *Leptochloa chinensis* (L.) Nees | sprangletop, Chinese |
| SCPJU | *Schoenoplectus juncoides* (Roxb.) Palla | bulrush, Japanese | gae/ha = grams acid equivalent per hectare
gai/ha = grams active ingredient per hectare
Obs = observed value
Exp = expected value as calculated by Colby's equation
DAA = days after application Table 25-continued values (top of column 82):

| Compound A Benzyl Ester | Rimsulfuron | Obs | Exp |
|---|---|---|---|
| 8.75 | 4.38 | 100 | 90 |
| 17.5 | 4.38 | 100 | 90 |

Example II

Evaluation of in-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters (cm$^2$) leaving a headspace of 3 centimeters (cm) in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 cm$^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29'C during the day and 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC and various herbicidal components alone and in combination. Forms of compound A were applied on an acid equivalent basis.

Forms of compound A (compound of formula I) tested include:

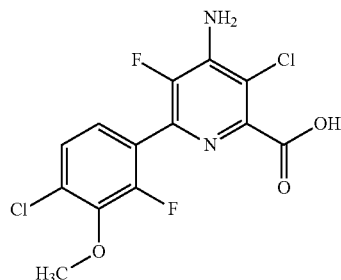

Compound A Acid

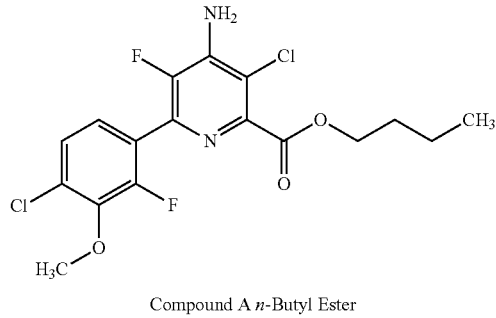

Compound A n-Butyl Ester

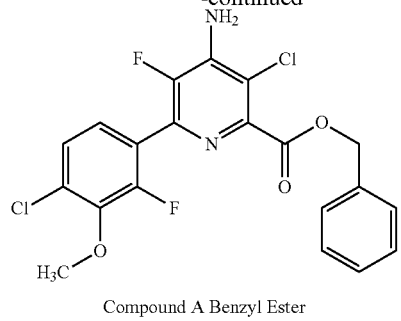

Compound A Benzyl Ester

Other herbicidal components were applied on an active ingredient basis and included acetolactate synthase (ALS)-inhibiting herbicides (sulfonylurea chemical class), azimsulfuron formulated as Gulliver®, bensulfuron-methyl formulated as Londax® 60DF, cyclosulfamuron (technical grade materail), ethoxysulfuron formulated as Sunrice® 15 WDG, flucetosulfuron formulated as Sukedachi® 1KG G, imazosulfuron formulated as Brazzos®, metsulfuron-methyl formulated as Lorate®, nicosulfuron formulated as Accent®, orthosulfamuron formulated as Strada® WG, propyrisulfuron formulated as Zeta One®, and rimsulfuron formulated as Matrix® WG.

Treatment requirements for each compound or herbicidal component were calculated based upon the rates being tested, the concentration of active ingredient or acid equivalent in the formulation, an application volume of 2 mL per component per pot, and an application area of 86.59 cm$^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 28-50.

TABLE 28

Synergistic Activity of In-Water Applications of Compound A Acid and Azimsulfuron Herbicidal Compositions on Weed Control in a Rice Cropping System.

| Compound A Acid | Azimsulfuron | Visual Weed Control (%) - 20 DAA | | | |
|---|---|---|---|---|---|
| | | ECHOR | | SCPMA | |
| gae/ha | gai/ha | Obs | Exp | Obs | Exp |
| 8.75 | 0 | 20 | — | 40 | — |
| 17.5 | 0 | 30 | — | 20 | — |
| 35 | 0 | 40 | — | 20 | — |
| 0 | 2.5 | 0 | — | 70 | — |
| 8.75 | 2.5 | 40 | 20 | 95 | 82 |
| 17.5 | 2.5 | 60 | 30 | 100 | 76 |
| 35 | 2.5 | 60 | 40 | 100 | 76 |
| 35 | 0 | 25 | — | 0 | — |
| 70 | 0 | 35 | — | 0 | — |
| 0 | 25 | 60 | — | 85 | — |
| 35 | 25 | 80 | 70 | 98 | 85 |
| 70 | 25 | 100 | 74 | 98 | 85 |

TABLE 29

Synergistic Activity of In-Water Applications of Compound A Benzyl Ester and Azimsulfuron Herbicidal Compositions on Weed Control in a Rice Cropping System.

| Compound A Benzyl Ester | Azimsulfuron | Visual Weed Control (%) - 20 DAA | |
|---|---|---|---|
| gae/ha | gai/ha | Obs | Exp |
| | | ECHOR | |
| 4.38 | 0 | 10 | — |
| 8.75 | 0 | 20 | — |
| 17.5 | 0 | 30 | — |
| 0 | 2.5 | 0 | — |
| 0 | 5 | 20 | — |
| 4.38 | 2.5 | 40 | 10 |
| 8.75 | 2.5 | 40 | 20 |
| 17.5 | 2.5 | 60 | 30 |
| 4.38 | 5 | 30 | 28 |
| 8.75 | 5 | 40 | 36 |
| 17.5 | 5 | 70 | 44 |
| | | SCPMA | |
| 4.38 | 0 | 10 | — |
| 8.75 | 0 | 0 | — |
| 17.5 | 0 | 20 | — |
| 0 | 2.5 | 70 | — |
| 4.38 | 2.5 | 80 | 73 |
| 8.75 | 2.5 | 80 | 70 |
| 17.5 | 2.5 | 90 | 76 |

TABLE 29-continued

Synergistic Activity of In-Water Applications of Compound A Benzyl Ester and Azimsulfuron Herbicidal Compositions on Weed Control in a Rice Cropping System.

| Compound A Benzyl Ester | Azimsulfuron | Visual Weed Control (%) - 20 DAA | | | |
|---|---|---|---|---|---|
| | | ECHOR | | SCPMA | |
| gae/ha | gai/ha | Obs | Exp | Obs | Exp |
| 35 | 0 | 53 | — | 0 | — |
| 70 | 0 | 73 | — | 0 | — |
| 0 | 25 | 60 | — | 85 | — |
| 35 | 25 | 88 | 81 | 90 | 85 |
| 70 | 25 | 100 | 89 | 100 | 85 |

TABLE 30

Synergistic Activity of In-Water Applications of Compound A n-Butyl Ester and Azimsulfuron Herbicidal Compositions on Weed Control in a Rice Cropping System.

| Compound A n-Butyl Ester | Azimsulfuron | Visual Weed Control (%) - 20 DAA ECHOR | |
|---|---|---|---|
| gae/ha | gai/ha | Obs | Exp |
| 35 | 0 | 28 | — |
| 70 | 0 | 45 | — |
| 0 | 25 | 60 | — |
| 35 | 25 | 75 | 71 |
| 70 | 25 | 93 | 78 |

TABLE 31

Synergistic Activity of In-Water Applications of Compound A Acid and Bensulfuron-Methyl Herbicidal Compositions on Weed Control in a Rice Cropping System.

| Compound A Acid | Bensulfuron-methyl | Visual Weed Control (%) - 25 DAA ECHOR | |
|---|---|---|---|
| gae/ha | gai/ha | Obs | Exp |
| 8.75 | 0 | 0 | — |
| 17.5 | 0 | 0 | — |
| 35 | 0 | 40 | — |
| 0 | 35 | 80 | — |
| 0 | 70 | 85 | — |
| 8.75 | 35 | 95 | 80 |
| 17.5 | 35 | 95 | 80 |
| 35 | 35 | 100 | 88 |
| 8.75 | 70 | 100 | 85 |
| 17.5 | 70 | 100 | 85 |
| 35 | 70 | 95 | 91 |

| Compound A Acid | Bensulfuron-methyl | Visual Weed Control (%) - 19 DAA | | | |
|---|---|---|---|---|---|
| | | ECHOR | | LEFCH | |
| gae/ha | gai/ha | Obs | Exp | Obs | Exp |
| 42 | 0 | 15 | — | 10 | — |
| 0 | 70 | 78 | — | 23 | — |
| 42 | 70 | 99 | 81 | 43 | 30 |

TABLE 32

Synergistic Activity of In-Water Applications of Compound A Benzyl Ester and Bensulfuron-Methyl Herbicidal Compositions on Weed Control in a Rice Cropping System.

| Compound A Benzyl Ester | Bensulfuron-methyl | Visual Weed Control (%) - 21 DAA | |
|---|---|---|---|
| gae/ha | gai/ha | Obs | Exp |
| ECHOR | | | |
| 8 | 0 | 8 | — |
| 16 | 0 | 5 | — |
| 0 | 35 | 0 | — |
| 0 | 70 | 15 | — |
| 8 | 35 | 30 | 8 |
| 16 | 35 | 20 | 5 |
| 8 | 70 | 35 | 21 |
| 16 | 70 | 20 | 19 |
| SCPMA | | | |
| 48 | 0 | 0 | — |
| 96 | 0 | 0 | — |
| 0 | 17.5 | 45 | — |
| 0 | 35 | 90 | — |
| 48 | 17.5 | 85 | 45 |
| 96 | 17.5 | 100 | 45 |
| 48 | 35 | 99 | 90 |
| 96 | 35 | 95 | 90 |

TABLE 33

Synergistic Activity of In-Water Applications of Compound A Benzyl Ester and Cyclosulfamuron Herbicidal Compositions on Weed Control in a Rice Cropping System.

| Compound A Benzyl Ester | Cyclosulfamuron | Visual Weed Control (%) - 21 DAA SCPMA | |
|---|---|---|---|
| gae/ha | gai/ha | Obs | Exp |
| 8 | 0 | 0 | — |
| 16 | 0 | 0 | — |
| 32 | 0 | 0 | — |
| 0 | 12.5 | 75 | — |
| 8 | 12.5 | 85 | 75 |
| 16 | 12.5 | 90 | 75 |
| 32 | 12.5 | 90 | 75 |

TABLE 34

Synergistic Activity of In-Water Applications of Compound A Acid and Ethoxysulfuron Herbicidal Compositions on Weed Control in a Rice Cropping System.

| Compound A Acid | Ethoxysulfuron | Visual Weed Control (%) - 22 DAA | |
|---|---|---|---|
| gae/ha | gai/ha | Obs | Exp |
| ECHOR | | | |
| 10.6 | 0 | 15 | — |
| 21.2 | 0 | 30 | — |
| 42.4 | 0 | 40 | — |
| 0 | 7.5 | 10 | — |
| 10.6 | 7.5 | 55 | 24 |
| 21.2 | 7.5 | 40 | 37 |
| 42.4 | 7.5 | 85 | 46 |
| LEFCH | | | |
| 10.6 | 0 | 20 | — |
| 21.2 | 0 | 40 | — |
| 42.4 | 0 | 60 | — |
| 0 | 15 | 0 | — |
| 10.6 | 15 | 20 | 20 |
| 21.2 | 15 | 50 | 40 |
| 42.4 | 15 | 100 | 60 |

TABLE 35

Synergistic Activity of In-Water Applications of Compound A Benzyl Ester and Ethoxysulfuron Herbicidal Compositions on Weed Control in a Rice Cropping System.

| Compound A Benzyl Ester | Ethoxysulfuron | Visual Weed Control (%) - 22 DAA | |
|---|---|---|---|
| gae/ha | gai/ha | Obs | Exp |
| ECHOR | | | |
| 17.5 | 0 | 30 | — |
| 0 | 7.5 | 10 | — |
| 0 | 15 | 20 | — |
| 17.5 | 7.5 | 99 | 37 |
| 17.5 | 15 | 85 | 44 |
| LEFCH | | | |
| 4.38 | 0 | 20 | — |
| 0 | 7.5 | 0 | — |
| 0 | 15 | 0 | — |
| 4.38 | 7.5 | 30 | 20 |
| 4.38 | 15 | 70 | 20 |

TABLE 36

Synergistic Activity of In-Water Applications of Compound A Acid and Flucetosulfuron Herbicidal Compositions on Weed Control in a Rice Cropping System.

| Compound A Acid | Flucetosulfuron | Visual Weed Control (%) - 21 DAA | |
|---|---|---|---|
| gae/ha | gai/ha | Obs | Exp |
| ECHOR | | | |
| 8.75 | 0 | 10 | — |
| 17.5 | 0 | 10 | — |
| 35 | 0 | 15 | — |
| 0 | 0.1 | 0 | — |
| 0 | 0.2 | 0 | — |
| 8.75 | 0.1 | 20 | 10 |
| 17.5 | 0.1 | 25 | 10 |
| 35 | 0.1 | 40 | 15 |
| 8.75 | 0.2 | 30 | 10 |
| 17.5 | 0.2 | 40 | 10 |
| 35 | 0.2 | 40 | 15 |
| LEFCH | | | |
| 17.5 | 0 | 20 | — |
| 0 | 0.1 | 0 | — |
| 0 | 0.2 | 0 | — |
| 17.5 | 0.1 | 50 | 20 |
| 17.5 | 0.2 | 50 | 20 |

TABLE 37

Synergistic Activity of In-Water Applications of Compound A Benzyl Ester and Flucetosulfuron Herbicidal Compositions on Weed Control in a Rice Cropping System.

| Compound A Benzyl Ester gae/ha | Flucetosulfuron gai/ha | Visual Weed Control (%) - 21 DAA ECHOR | |
|---|---|---|---|
| | | Obs | Exp |
| 8.75 | 0 | 25 | — |
| 17.5 | 0 | 25 | — |
| 0 | 0.1 | 0 | — |
| 0 | 0.2 | 0 | — |
| 8.75 | 0.1 | 70 | 25 |
| 17.5 | 0.1 | 95 | 25 |
| 8.75 | 0.2 | 30 | 25 |
| 17.5 | 0.2 | 95 | 25 |

TABLE 38

Synergistic Activity of In-Water Applications of Compound A Acid and Imazosulfuron Herbicidal Compositions on Weed Control in a Rice Cropping System.

| Compound A Acid gae/ha | Imazosulfuron gai/ha | Obs | Exp |
|---|---|---|---|
| | | Visual Weed Control (%) - 21 DAA ECHCO | |
| 8.75 | 0 | 0 | — |
| 17.5 | 0 | 20 | — |
| 0 | 22.5 | 20 | — |
| 0 | 45 | 20 | — |
| 8.75 | 22.5 | 30 | 20 |
| 17.5 | 22.5 | 65 | 36 |
| 8.75 | 45 | 55 | 20 |
| 17.5 | 45 | 50 | 36 |
| | | Visual Weed Control (%) - 20 DAA SCPMA | |
| 35 | 0 | 0 | — |
| 70 | 0 | 0 | — |
| 0 | 168 | 65 | — |
| 35 | 168 | 90 | 65 |
| 70 | 168 | 100 | 65 |

TABLE 39

Synergistic Activity of In-Water Applications of Compound A Benzyl Ester and Imazosulfuron Herbicidal Compositions on Weed Control in a Rice Cropping System.

| Compound A Benzyl Ester gae/ha | Imazosulfuron gai/ha | Obs | Exp |
|---|---|---|---|
| | | Visual Weed Control (%) - 21 DAA ECHCO | |
| 4.38 | 0 | 45 | — |
| 8.75 | 0 | 30 | — |
| 17.5 | 0 | 95 | — |
| 0 | 45 | 20 | — |
| 4.38 | 45 | 70 | 56 |
| 8.75 | 45 | 70 | 44 |
| 17.5 | 45 | 95 | 96 |

TABLE 39-continued

Synergistic Activity of In-Water Applications of Compound A Benzyl Ester and Imazosulfuron Herbicidal Compositions on Weed Control in a Rice Cropping System.

| Compound A Benzyl Ester gae/ha | Imazosulfuron gai/ha | Obs | Exp |
|---|---|---|---|
| | | Visual Weed Control (%) - 20 DAA SCPMA | |
| 35 | 0 | 0 | — |
| 70 | 0 | 0 | — |
| 0 | 168 | 65 | — |
| 35 | 168 | 95 | 65 |
| 70 | 168 | 100 | 65 |

TABLE 40

Synergistic Activity of In-Water Applications of Compound A n-Butyl Ester and Imazosulfuron Herbicidal Compositions on Weed Control in a Rice Cropping System.

| Compound A n-Butyl Ester gae/ha | Imazosulfuron gai/ha | Visual Weed Control (%) - 20 DAA SCPMA | |
|---|---|---|---|
| | | Obs | Exp |
| 35 | 0 | 0 | — |
| 70 | 0 | 0 | — |
| 0 | 168 | 65 | — |
| 35 | 168 | 95 | 65 |
| 70 | 168 | 95 | 65 |

TABLE 41

Synergistic Activity of In-Water Applications of Compound A Acid and Metsulfuron-methyl Herbicidal Compositions on Weed Control in a Rice Cropping System.

| Compound A Acid gae/ha | Metsulfuron-methyl gai/ha | Visual Weed Control (%) - 21 DAA ECHOR | |
|---|---|---|---|
| | | Obs | Exp |
| 10.6 | 0 | 0 | — |
| 21.2 | 0 | 15 | — |
| 42.4 | 0 | 15 | — |
| 0 | 7.5 | 50 | — |
| 0 | 15 | 65 | — |
| 10.6 | 7.5 | 85 | 50 |
| 21.2 | 7.5 | 80 | 58 |
| 42.4 | 7.5 | 85 | 58 |
| 10.6 | 15 | 90 | 65 |
| 21.2 | 15 | 85 | 70 |
| 42.4 | 15 | 99 | 70 |

TABLE 42

Synergistic Activity of In-Water Applications of Compound A Benzyl Ester and Metsulfuron-methyl Herbicidal Compositions on Weed Control in a Rice Cropping System.

| Compound A Benzyl Ester gae/ha | Metsulfuron-methyl gai/ha | Visual Weed Control (%) - 21 DAA ECHOR | |
|---|---|---|---|
| | | Obs | Exp |
| 4.38 | 0 | 15 | — |
| 8.75 | 0 | 15 | — |

TABLE 42-continued

Synergistic Activity of In-Water Applications of Compound A Benzyl Ester and Metsulfuron-methyl Herbicidal Compositions on Weed Control in a Rice Cropping System.

| Compound A Benzyl Ester | Metsulfuron-methyl | Visual Weed Control (%) - 21 DAA ECHOR | |
|---|---|---|---|
| gae/ha | gai/ha | Obs | Exp |
| 17.5 | 0 | 20 | — |
| 0 | 7.5 | 50 | — |
| 0 | 15 | 65 | — |
| 4.38 | 7.5 | 80 | 58 |
| 8.75 | 7.5 | 90 | 58 |
| 17.5 | 7.5 | 85 | 60 |
| 4.38 | 15 | 90 | 70 |
| 8.75 | 15 | 99 | 70 |
| 17.5 | 15 | 100 | 72 |

TABLE 43

Synergistic Activity of In-Water Applications of Compound A Acid and Nicosulfuron Herbicidal Compositions on Control of Weeds Common to Rice Cropping Systems.

| Compound A Acid | Nicosulfuron | Visual Weed Control (%) - 20 DAA | | | |
|---|---|---|---|---|---|
| | | ECHOR | | LEFCH | |
| gae/ha | gai/ha | Obs | Exp | Obs | Exp |
| 10.6 | 0 | 10 | — | 30 | — |
| 21.2 | 0 | 30 | — | 20 | — |
| 42.4 | 0 | 45 | — | 75 | — |
| 0 | 17.5 | 0 | — | 60 | — |
| 10.6 | 17.5 | 50 | 10 | 90 | 72 |
| 21.2 | 17.5 | 40 | 30 | 100 | 68 |
| 42.4 | 17.5 | 65 | 45 | 100 | 90 |

| Compound A Acid | Nicosulfuron | Visual Weed Control (%) - 20 DAA CYPRO | |
|---|---|---|---|
| gae/ha | gai/ha | Obs | Exp |
| 10.6 | 0 | 10 | — |
| 21.2 | 0 | 20 | — |
| 0 | 17.5 | 30 | — |
| 0 | 35 | 70 | — |
| 10.6 | 17.5 | 50 | 37 |
| 21.2 | 17.5 | 70 | 44 |
| 10.6 | 35 | 99 | 73 |
| 21.2 | 35 | 95 | 76 |

TABLE 44

Synergistic Activity of In-Water Applications of Compound A Benzyl Ester and Nicosulfuron Herbicidal Compositions on Control of Weeds Common to Rice Cropping Systems.

| Compound A Benzyl Ester | Nicosulfuron | Visual Weed Control (%) - 20 DAA ECHOR | |
|---|---|---|---|
| gae/ha | gai/ha | Obs | Exp |
| 8.75 | 0 | 20 | — |
| 17.5 | 0 | 30 | — |
| 0 | 17.5 | 0 | — |
| 0 | 35 | 50 | — |
| 8.75 | 17.5 | 30 | 20 |
| 17.5 | 17.5 | 85 | 30 |
| 8.75 | 35 | 90 | 60 |
| 17.5 | 35 | 85 | 65 |

TABLE 45

Synergistic Activity of In-Water Applications of Compound A Acid and Orthosulfamuron Herbicidal Compositions on Weed Control in a Rice Cropping System.

| Compound A Acid | Orthosulfamuron | Visual Weed Control (%) - 20 DAA SCPMA | |
|---|---|---|---|
| gae/ha | gai/ha | Obs | Exp |
| 42.4 | 0 | 0 | — |
| 84.8 | 0 | 0 | — |
| 0 | 60 | 85 | — |
| 42.4 | 60 | 95 | 85 |
| 84.8 | 60 | 100 | 85 |

TABLE 46

Synergistic Activity of In-Water Applications of Compound A Benzyl Ester and Orthosulfamuron Herbicidal Compositions on Weed Control in a Rice Cropping System.

| Compound A Benzyl Ester | Orthosulfamuron | Visual Weed Control (%) - 20 DAA SCPMA | |
|---|---|---|---|
| gae/ha | gai/ha | Obs | Exp |
| 35 | 0 | 0 | — |
| 70 | 0 | 0 | — |
| 0 | 60 | 85 | — |
| 35 | 60 | 98 | 85 |
| 70 | 60 | 95 | 85 |

| Compound A Benzyl Ester | Orthosulfamuron | Visual Weed Control (%) - 21 DAA ECHOR | |
|---|---|---|---|
| gae/ha | gai/ha | Obs | Exp |
| 4.38 | 0 | 0 | — |
| 8.75 | 0 | 10 | — |
| 17.5 | 0 | 60 | — |
| 0 | 15 | 10 | — |
| 4.38 | 15 | 25 | 10 |
| 8.75 | 15 | 25 | 19 |
| 17.5 | 15 | 85 | 64 |

TABLE 47

Synergistic Activity of In-Water Applications of Compound A Acid and Propyrisulfuron Herbicidal Compositions on Weed Control in a Rice Cropping System.

| Compound A Acid | Propyrisulfuron | Visual Weed Control (%) - 21 DAA LEFCH | |
|---|---|---|---|
| gae/ha | gai/ha | Obs | Exp |
| 8.75 | 0 | 0 | — |
| 17.5 | 0 | 20 | — |
| 0 | 22.5 | 0 | — |
| 0 | 45 | 0 | — |
| 8.75 | 22.5 | 30 | 0 |
| 17.5 | 22.5 | 50 | 20 |
| 8.75 | 45 | 100 | 0 |
| 17.5 | 45 | 30 | 20 |

TABLE 48

Synergistic Activity of In-Water Applications of Compound A Benzyl Ester and Propyrisulfuron Herbicidal Compositions on Weed Control in a Rice Cropping System.

| Compound A Benzyl Ester | Propyrisulfuron | Visual Weed Control (%) - 21 DAA FIMMI | |
|---|---|---|---|
| gae/ha | gai/ha | Obs | Exp |
| 8 | 0 | 15 | — |
| 16 | 0 | 65 | — |
| 32 | 0 | 75 | — |
| 0 | 11.25 | 85 | — |
| 0 | 22.5 | 88 | — |
| 0 | 45 | 95 | — |
| 8 | 11.25 | 100 | 87 |
| 16 | 11.25 | 100 | 95 |
| 32 | 11.25 | 100 | 96 |
| 8 | 22.5 | 100 | 89 |
| 16 | 22.5 | 100 | 96 |
| 32 | 22.5 | 100 | 97 |
| 8 | 45 | 100 | 96 |
| 16 | 45 | 100 | 98 |
| 32 | 45 | 100 | 99 |

| Compound A Benzyl Ester | Propyrisulfuron | Visual Weed Control (%) - 21 DAA SCPMA | |
|---|---|---|---|
| gae/ha | gai/ha | Obs | Exp |
| 8 | 0 | 0 | — |
| 16 | 0 | 0 | — |
| 32 | 0 | 0 | — |
| 0 | 11.25 | 80 | — |
| 8 | 11.25 | 95 | 80 |
| 16 | 11.25 | 85 | 80 |
| 32 | 11.25 | 100 | 80 |

TABLE 49

Synergistic Activity of In-Water Applications of Compound A Acid and Rimsulfuron Herbicidal Compositions on Control of Weeds Common to Rice Cropping Systems.

| Compound A Acid | Rimsulfuron | Visual Weed Control (%) - 20 DAA | | | |
|---|---|---|---|---|---|
| | | LEFCH | | CYPRO | |
| gae/ha | gai/ha | Obs | Exp | Obs | Exp |
| 10.6 | 0 | 30 | — | 10 | — |
| 21.2 | 0 | 20 | — | 20 | — |
| 42.4 | 0 | 75 | — | 95 | — |
| 0 | 4.38 | 0 | — | 0 | — |
| 10.6 | 4.38 | 50 | 30 | 100 | 10 |
| 21.2 | 4.38 | 50 | 20 | 90 | 20 |
| 42.4 | 4.38 | 90 | 75 | 99 | 95 |

TABLE 50

Synergistic Activity of In-Water Applications of Compound A Benzyl Ester and Rimsulfuron Herbicidal Compositions on Control of Weeds Common to Rice Cropping Systems.

| Compound A Benzyl Ester | Rimsulfuron | Visual Weed Control (%) - 20 DAA ECHCG | |
|---|---|---|---|
| gae/ha | gai/ha | Obs | Exp |
| 4.38 | 0 | 15 | — |
| 8.75 | 0 | 20 | — |
| 17.5 | 0 | 40 | — |
| 0 | 4.38 | 0 | — |
| 0 | 8.75 | 0 | — |
| 4.38 | 4.38 | 20 | 15 |
| 8.75 | 4.38 | 35 | 20 |
| 17.5 | 4.38 | 25 | 40 |
| 4.38 | 8.75 | 30 | 15 |
| 8.75 | 8.75 | 25 | 20 |
| 17.5 | 8.75 | 95 | 40 |

| Compound A Benzyl Ester | Rimsulfuron | Visual Weed Control (%) - 20 DAA LEFCH | |
|---|---|---|---|
| gae/ha | gai/ha | Obs | Exp |
| 4.38 | 0 | 20 | — |
| 0 | 4.38 | 0 | — |
| 0 | 8.75 | 30 | — |
| 4.38 | 4.38 | 70 | 20 |
| 4.38 | 8.75 | 100 | 44 |

| Compound A Benzyl Ester | Rimsulfuron | Visual Weed Control (%) - 20 DAA CYPRO | |
|---|---|---|---|
| gae/ha | gai/ha | Obs | Exp |
| 4.38 | 0 | 50 | — |
| 8.75 | 0 | 0 | — |
| 17.5 | 0 | 90 | — |
| 0 | 4.38 | 0 | — |
| 4.38 | 4.38 | 90 | 50 |
| 8.75 | 4.38 | 90 | 0 |
| 17.5 | 4.38 | 85 | 90 |

| | | |
|---|---|---|
| CYPRO | *Cyperus rotundus* L. | nutsedge, purple |
| ECHCG | *Echinochloa crusgalli* (L.) Beauv. | barnyardgrass |
| ECHCO | *Echinochloa colona* (L.) Link | junglerice |
| ECHOR | *Echinochloa oryzoides* (Ard.) Fritsch | watergrass, early |
| FIMMI | *Fimbristylis miliacea* (L.) Vahl | fringerush, globe |
| LEFCH | *Leptochloa chinensis* (L.) Nees | sprangletop, Chinese |
| SCPMA | *Schoenoplectus maritimus* (L.) Lye | clubrush, sea | gae/ha = grams acid equivalent per hectare
gai/ha = grams active ingredient per hectare
Obs = observed value
Exp = expected value as calculated by Colby's equation
DAA = days after application Example III Evaluation of Post-Emergence Foliar-Applied Herbicidal Mixtures for Weed Control in Cereal Crops in the Greenhouse Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC (suspension concentrate), and a second cereal herbicide alone and in combination.

Forms of compound A (compound of formula I) tested include:

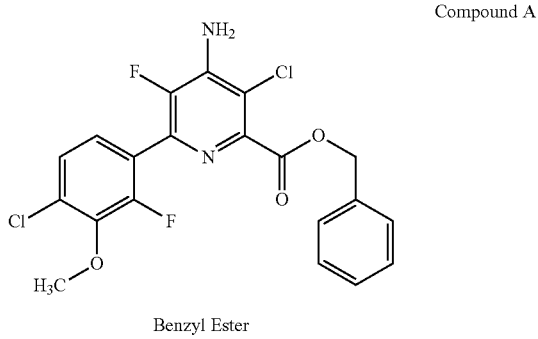 [SMILES: COc1c(Cl)ccc(-c2nc(C(=O)OCc3ccccc3)c(Cl)c(N)c2F)c1F]

Compound A

Benzyl Ester

Measured aliquot of benzyl ester of 4-amino-3-chloro-5-fluoro-6-(4-chloro-2-fluoro-3-methoxy-phenyl)pyridine-2-carboxylic acid (Compound A) was placed in 25 milliliter (mL) glass vials and diluted in a volume of 1.25% (v/v) Agri-dex crop oil concentrated to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters (m²) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 51-57.

TABLE 51

Synergistic Activity of Foliar-Applied Compound A Benzyl Ester and Amidosulfuron Herbicidal Compositions on Weed Control in a Cereal Cropping System.

| Application Rate (gai/ha) | | GALAP | | LAMPU | | VERPE | |
|---|---|---|---|---|---|---|---|
| Compound A Benzyl Ester | Amido-sulfuron | Obs | Exp | Obs | Exp | Obs | Exp |
| 8.75 | 0 | 70 | — | 83 | — | 50 | — |
| 0 | 10 | 48 | — | 0 | — | 0 | — |
| 8.75 | 10 | 93 | 84 | 89 | 83 | 65 | 50 |

TABLE 52

Synergistic Activity of Foliar-Applied Compound A Benzyl Ester and Chlorsulfuron Herbicidal Compositions on Weed Control in a Cereal Cropping System.

| Application Rate (gai/ha) | | VIOTR | | CIRAR | |
|---|---|---|---|---|---|
| Compound A Benzyl Ester | Chlorsulfuron | Obs | Exp | Obs | Exp |
| 8.75 | 0 | 50 | — | 40 | — |
| 0 | 2.2 | 70 | — | 78 | — |
| 8.75 | 2.2 | 89 | 85 | 96 | 87 |

TABLE 53

Synergistic Activity of Foliar-Applied Compound A Benzyl Ester and Flupyrsulfuron-methyl sodium Herbicidal Compositions on Weed Control in a Cereal Cropping System.

| Application Rate (gai/ha) | | VERPE | | CIRAR | |
|---|---|---|---|---|---|
| Compound A Benzyl Ester | Flupyrsulfuron-methyl sodium | Obs | Exp | Obs | Exp |
| 8.75 | 0 | 50 | — | 40 | — |
| 0 | 5 | 0 | — | 75 | — |
| 8.75 | 5 | 63 | 50 | 95 | 85 |

TABLE 54

Synergistic Activity of Foliar-Applied Compound A Benzyl Ester and Iodosulfuron-methyl sodium Herbicidal Compositions on Weed Control in a Cereal Cropping System.

| Application Rate (gai/ha) | | VIOTR | | MATCH | | CIRAR | |
|---|---|---|---|---|---|---|---|
| Compound A Benzyl Ester | Iodosulfuron-methyl sodium | Obs | Exp | Obs | Exp | Obs | Exp |
| 8.75 | 0 | 50 | — | 20 | — | 40 | — |
| 0 | 2.5 | 82 | — | 94 | — | 60 | — |
| 8.75 | 2.5 | 94 | 91 | 100 | 95 | 99 | 76 |

TABLE 55

Synergistic Activity of Foliar-Applied Compound A Benzyl Ester and Mesoulfuron-methyl Herbicidal Compositions on Weed Control in a Cereal Cropping System.

| Application Rate (gai/ha) | | VERPE | | MATCH | | CIRAR | |
|---|---|---|---|---|---|---|---|
| Compound A Benzyl Ester | Mesosulfuron-methyl | Obs | Exp | Obs | Exp | Obs | Exp |
| 8.75 | 0 | 50 | — | 20 | — | 40 | — |
| 0 | 3 | 5 | — | 40 | — | 78 | — |
| 8.75 | 3 | 68 | 53 | 75 | 52 | 96 | 87 |

TABLE 56

Synergistic Activity of Foliar-Applied Compound A Benzyl Ester and Metsulfuron-methyl Herbicidal Compositions on Weed Control in a Cereal Cropping System.

| Application Rate (gai/ha) | | MATCH | | CIRAR | |
|---|---|---|---|---|---|
| Compound A Benzyl Ester | Metsulfuron-methyl | Obs | Exp | Obs | Exp |
| 8.75 | 0 | 20 | — | 40 | — |
| 0 | 1.1 | 89 | — | 65 | — |
| 8.75 | 1.1 | 96 | 91 | 97 | 79 |

TABLE 57

Synergistic Activity of Foliar-Applied Compound A Benzyl Ester and Sulfosulfuron Herbicidal Compositions on Weed Control in a Cereal Cropping System.

| Application Rate (gai/ha) | | LAMPU | | VERPE | | MATCH | | CIRAR | |
|---|---|---|---|---|---|---|---|---|---|
| Compound A Benzyl Ester | Sulfosulfuron | Obs | Exp | Obs | Exp | Obs | Exp | Obs | Exp |
| 8.75 | 0 | 83 | — | 50 | — | 20 | — | 40 | — |
| 0 | 8.75 | 5 | — | 35 | — | 95 | — | 70 | — |
| 8.75 | 8.75 | 94 | 83 | 75 | 68 | 100 | 96 | 85 | 82 |

TABLE 58

Synergistic Activity of Foliar-Applied Compound A Benzyl Ester and Thifensulfuron-methyl Herbicidal Compositions on Weed Control in a Cereal Cropping System.

| Application Rate (gai/ha) | | CIRAR | |
|---|---|---|---|
| Compound A Benzyl Ester | Thifensulfuron-methyl | Obs | Exp |
| 8.75 | 0 | 40 | — |
| 0 | 3.75 | 35 | — |
| 8.75 | 3.75 | 80 | 61 |

TABLE 59

Synergistic Activity of Foliar-Applied Compound A Benzyl Ester and Tribenuron-methyl Herbicidal Compositions on Weed Control in a Cereal Cropping System.

| Application Rate (gai/ha) | | MATCH | | CIRAR | |
|---|---|---|---|---|---|
| Compound A Benzyl Ester | Tribenuron-methyl | Obs | Exp | Obs | Exp |
| 8.75 | 0 | 20 | — | 40 | — |
| 0 | 2.2 | 90 | — | 50 | — |
| 8.75 | 2.2 | 95 | 92 | 80 | 70 |

| | | |
|---|---|---|
| GALAP | *Galium aparine* (L.) | cleavers |
| MATCH | *Chamomilla chamomilla* (L.) Rydb. | mayweed, scented |
| VERPE | *Veronica persica* Poir. | speedwell, bird's-eye |
| VIOTR | *Viola tricolor* (L.) | pansy, wild |
| CIRAR | *Cirsium arvense* (L.) Scop. | thistle, Canada |
| LAMPU | *Lamium purpureum* (L.) | deadnettle, purple |

Example IV

Evaluation of Post-Emergence Herbicidal Activity of Mixtures in Forage Crops in the Greenhouse Seeds or root cuttings of the desired test plant species were planted in Sun Gro MetroMix® 306 planting mixture, which typically has a pH of 6.0 to 6.8 and an organic matter content of about 30 percent, in plastic pots with a surface area of 126.6 square centimeters ($cm^2$). When required to ensure good germination and healthy plants, a fungicide treatment and/or other chemical or physical treatment was applied. The plants were grown for 14-60 days in a greenhouse with an approximate 14 hour photoperiod which was maintained at approximately 28° C. during the day and 24° C. during the night. Nutrients and water were added on a regular basis and supplemental lighting was provided with overhead metal halide 1000-Watt lamps as necessary. The plants were employed for testing when they reached the BBCH13 to BBCH23 leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as a SC, and a second herbicide alone and in combination.

Forms of compound A (compound of formula I) tested include:

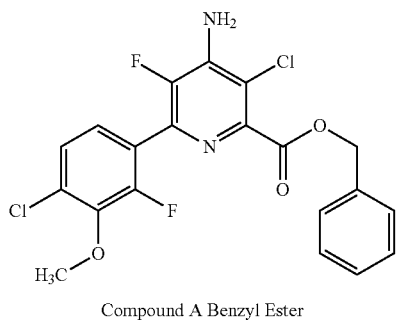 [SMILES: COc1c(Cl)ccc(-c2nc(C(=O)OCc3ccccc3)c(Cl)c(N)c2F)c1F]

Compound A Benzyl Ester

A measured aliquot of Compound A was placed in 25 milliliter (mL) glass vial and diluted in a volume of 1.25% (v/v) Agri-dex crop oil concentrated to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After approximately 21 days, the condition of the test plants, as compared with that of the control plants, was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 58.

TABLE 58

Synergistic Activity of Foliar-Applied Compound A Benzyl Ester and Metsulfuron methyl Ester (ME) Herbicidal Compositions on Weed Control in a Forage System.

| Application Rate (gai/ha) | | SIDSP | | CASOB | | POROL | |
|---|---|---|---|---|---|---|---|
| Compound A Benzyl Ester | Metsulfuron ME | Obs | Exp | Obs | Exp | Obs | Exp |
| 2.2 | 0 | 77 | — | 33 | — | 47 | — |
| 4.4 | 0 | 85 | — | 38 | — | 60 | — |

TABLE 58-continued

Synergistic Activity of Foliar-Applied Compound A Benzyl
Ester and Metsulfuron methyl Ester (ME) Herbicidal Compositions
on Weed Control in a Forage System.

| 0 | 1.1 | 52 | — | 8 | — | 80 | — |
| 2.2 | 1.1 | 96 | 89 | 50 | 39 | 93 | 89 |
| 4.4 | 1.1 | 98 | 93 | 65 | 43 | 95 | 92 |

| CASOB | *Cassia obtusifolia* L. | sicklepod |
| POROL | *Portulaca oleracea* L. | portulaca |
| SIDSP | *Sida spinosa* L. | sida, prickly |

Example V

Evaluation of Pre-Emergence Soil-Applied
Herbicidal Mixtures for Weed Control

Seeds or nutlets of the desired test plant species were planted in a soil matrix prepared by mixing a loam soil (32 percent silt, 23 percent clay, and 45 percent sand, with a pH of about 6.5 and an organic matter content of about 1.9 percent) and calcareous grit in an 80 to 20 ratio. The soil matrix was contained in plastic pots with a volume of 1 quart and a surface area of 83.6 square centimeters ($cm^2$).

Treatments consisted of the benzyl ester of 4-amino-3-chloro-5-fluoro-6-(4-chloro-2-fluoro-3-methoxy-phenyl)pyridine-2-carboxylic acid (compound A) formulated as an SC (suspension concentrate) and various herbicidal components alone and in combination. Forms of compound A were applied on an acid equivalent basis.

Forms of compound A (compound of formula I) tested include:

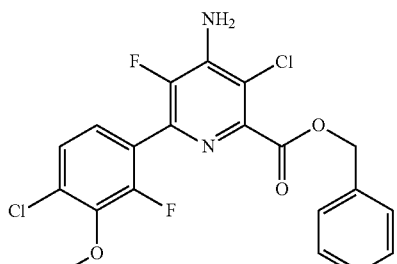

Compound A Benzyl Ester

Other herbicidal components were applied on an acid equivalent or active ingredient basis and included the acetolactate synthase (ALS)-inhibiting herbicide, flazasulfuron, formulated as Katana®.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrate (COC) to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) COC so that the final spray solutions contained 1.25% (v/v) COC.

For treatments comprised of technical compounds, weighed amounts can be placed individually in 25 mL glass vials and dissolved in a volume of 97:3 (v/v) acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) COC so that the final spray solutions contain 1.25% (v/v) COC. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 (v/v) acetone/DMSO to obtain 12× stock solutions, and measured amounts of the formulated compounds can be placed individually in 25 mL glass vials and diluted in a volume of 1.5% (v/v) COC or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) COC so that the final spray solutions contain 1.25% (v/v) COC. As required, additional water and/or 97:3 (v/v) acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the soil with an overhead Mandel track sprayer equipped with a 8002E nozzles calibrated to deliver 187 L/ha over an application area of 0.503 $m^2$ at a spray height of 18 inches (46 cm) above average pot height. Control pots were sprayed in the same manner with the solvent blank.

The treated and control pots were placed in a greenhouse and top watered as needed. When required to ensure good germination and healthy plants, a fungicide treatment and/or other chemical or physical treatment was applied. The pots were maintained in a greenhouse with an approximate 14 hr photoperiod which was maintained at about 29° C. during the day and 26° C. during the night. Nutrients (Peters® Excel 15-5-15 5-Ca 2-Mg) were applied in the irrigation solution as needed and water was added on a regular basis. Supplemental lighting was provided with overhead metal halide 1000-Watt lamps as necessary. After approximately 4 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A\times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 59.

TABLE 59

Synergistic Activity of Soil-applied, Pre-emergence Applications of Compound A Benzyl Ester and Flazasulfuron Herbicidal Compositions on Weed Control

| Compound A Benzyl Ester | Flazasulfuron | Visual Weed Control (%) - 27 DAA SETFA | |
|---|---|---|---|
| gae/ha | gai/ha | Obs | Exp |
| 16 | 0 | 8 | — |
| 32 | 0 | 15 | — |
| 0 | 25 | 62 | — |
| 16 | 25 | 82 | 65 |
| 32 | 25 | 92 | 67 |

| | | | |
|---|---|---|---|
| SETFA | *Setaria faberi* Herrm. | | foxtail, giant |
| gae/ha = grams acid equivalent per hectare | | | |
| gai/ha = grams active ingredient per hectare | | | |
| Obs = observed value | | | |
| Exp = expected value as calculated by Colby's equation | | | |
| DAA = days after application | | | |

What is claimed is:

1. A herbicidal composition comprising a herbicidally effective amount of
   (a) a compound of the formula (I):

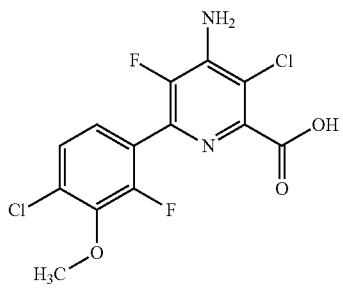

or an agriculturally acceptable salt or ester thereof and
   (b) a compound selected from the group consisting of: amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, rimsulfuron, sulfometuron-methyl, sulfosulfuron, thifensulfuron-methyl, triasulfuron, tribenuron-methyl or trifloxysulfuron-sodium, or a salt or ester thereof, wherein (a) and (b) are present in the composition in a ratio such that the composition exhibits herbicidal synergy.

2. The composition of claim 1, further comprising a herbicide safener.

3. The composition of claim 1, further comprising an agriculturally acceptable adjuvant or carrier.

4. A method of controlling undesirable vegetation comprising the steps of: contacting the vegetation or the locus thereof with, or applying to soil or water to prevent the emergence or growth of vegetation, a herbicidally effective amount of a combination comprising (a) a compound of the formula (I):

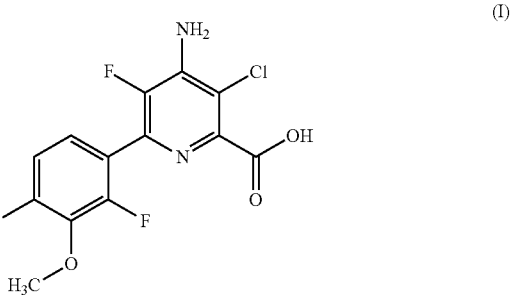

or an agriculturally acceptable salt or ester thereof; and
   (b) a compound selected from the group consisting of: amidosulfuron, azimsulfuron, bensulfuron-methyl, chlorsulfuron, cyclosulfamuron, ethametsulfuron-methyl, ethoxysulfuron, flazasulfuron, flucetosulfuron, flupyrsulfuron-methyl sodium, foramsulfuron, imazosulfuron, iofensulfuron, iodosulfuron-methyl sodium, mesosulfuron-methyl, metsulfuron-methyl, nicosulfuron, orthosulfamuron, primisulfuron-methyl, propyrisulfuron, rimsulfuron, sulfometuron-methyl, sulfosulfuron, thifensulfuron-methyl, triasulfuron, tribenuron-methyl or trifloxysulfuron-sodium, or a salt or ester thereof, wherein (a) and (b) are present in the combination in a ratio such that the combination exhibits herbicidal synergy; wherein the undesirable vegetation is controlled in direct-seeded, water-seeded and transplanted rice, cereals, wheat, barley, oats, rye, sorghum, maize, pastures, grasslands, rangelands and fallowland.

5. The method of claim 4, wherein the undesirable vegetation is immature.

6. The method of claim 4, wherein the (a) and (b) are applied to the water.

7. The method of claim 6, wherein the water is part of a flooded rice paddy.

8. The method of claim 6, wherein the (a) and (b) are applied pre-emergently to the undesirable vegetation or the crop.

9. The method of claim 6, wherein the (a) and (b) are applied post-emergently to the undesirable vegetation or the crop.

10. The method of claim 6, wherein the undesirable vegetation is controlled in glyphosate-, 5-enolpyruvylshikimate-3-phosphate synthase inhibitor-, glufosinate-, glutamine synthetase inhibitor-, dicamba-, phenoxy carboxylic acid auxin-, pyridine carboxylic acid auxin-, synthetic auxin-, auxin transport inhibitor-, aryloxyphenoxypropionates-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, long chain fatty acid inhibitor-, fatty acid and lipid biosynthesis inhibitor-, photosystem I inhibitor-, photosystem II inhibitor-, triazine-, or bromoxynil-tolerant crop.

11. The method of claim 6, wherein the tolerant crop possesses multiple or stacked traits conferring tolerance to multiple herbicides.

12. The method of claim 6 wherein the undesirable vegetation comprises a herbicide resistant or tolerant plant.

13. The method of claim 12, wherein the resistant or tolerant plant is resistant or tolerant to multiple herbicides.

14. The method of claim 12 wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *